United States Patent
Ho

(10) Patent No.: US 6,491,922 B1
(45) Date of Patent: *Dec. 10, 2002

(54) METHODS AND COMPOUNDS FOR TREATING AUTOIMMUNE AND VASCULAR DISEASE

(75) Inventor: John L. Ho, New York, NY (US)

(73) Assignee: Cornell Research Foundation, Inc., Ithaca, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/794,500

(22) Filed: Feb. 4, 1997

Related U.S. Application Data

(60) Provisional application No. 60/011,406, filed on Feb. 9, 1996.

(51) Int. Cl.[7] ...................... A61K 39/385; A61K 39/00; A61K 39/002; A61K 38/00
(52) U.S. Cl. ................ 424/193.1; 424/265.1; 424/269.1; 514/2
(58) Field of Search ............... 424/193.1, 265.1, 424/269.1; 514/2

(56) References Cited

U.S. PATENT DOCUMENTS

| | | | |
|---|---|---|---|
| 4,687,666 A | * | 8/1987 | O'Daly |
| 4,992,273 A | | 2/1991 | Monjour et al. |
| 5,180,812 A | | 1/1993 | Dower et al. |
| 5,231,012 A | | 7/1993 | Mosmann et al. |
| 5,286,847 A | | 2/1994 | Gehrke et al. |
| 5,334,380 A | | 8/1994 | Kilbourn et al. |

FOREIGN PATENT DOCUMENTS

| FR | 2 570 947 A1 | 10/1984 |
|---|---|---|
| FR | 2 577 140 A1 | 2/1985 |

OTHER PUBLICATIONS

Moore et al (J. of Immunology vol. 152, No. 6, Mar. 15, 1994 pp 2930–2937).*
Descoteaux et al (Journal of immunology vol. 146(8) pp 2747–2753), Apr. 15, 1991).*
Brady, Hugh R., "Leukocyte Adhesion Molecules: Potential Targets for Therapeutic Intervention in Kidney Diseases," *Current Science ISSN*, 2:171–182 (1993).
Turco et al., "The Lipophosphoglycan of Leishmania Parasites," *Annu. Rev. Microbiol.*, 46:65–94 (1992).
Morrison et al., "Current Status of Bacterial Endotoxins," *ASM News*, 60(9):479–484 (1994).
Kelleher et al., "Lipophosphoglycan Blocks Attachment of Leishmania major Amastigotes to Macrophages," *Infection and Immunity*, 63(1): 43–50 (1995).
Frankenburg et al., "Effect of Glycolipids of Leishmania Parasites on Human Monocyte Activity," *The Journal of Immunology*, 145(12):4284–4289 (1990).
Easterbrook et al., "Inhibition of HIV–1–Induced Syncytia Formation and Infectivity by Lipophosphoglycan from eishmania," *Journal of Acquired Immune Deficiency and Human Retrovirology* 10:496–505 (1995).
Carrera et al., "Leishmania Promastigotes Selectively Inhibit Interleukin 12 Induction in Bone Marrow–Derived Macrophages From Susceptible and Resistant Mice," *The Journal of Experimental Medicine* 183:515–526 (1996).
Hirata et al., "Endotoxin–Binding Synthetic Peptides with Endotoxin–Neutralizing, Antibacterial and Anticoagulant Activities," *Bacterial Endotoxins: Basic Science to Anti–Sepsis Strategies* 388:147–159 (1994).
van der Logt et al., "Expression of Tissue Factor and Tissue Factor Pathway Inhibitor in Monocytes in Response to Bacterial Lipopolysaccharide and Phorbolester," *Blood Coagulation and Fibrinolysis* 5:211–220 (1994).
Kemp et al., "Production of Interferon–Gamma and Interleukin–4 by Human T Cells Recognizing Leishmania Lipophosphoglycan–Associates Protein," *Immunology Letters* 38:137–144 (1993).
Kotani et al., "Synthetic Lipid A with Endotoxic and Related Biological Activities Comparable to Those of a Natural Lipid A From an *Escherichia coli* Re–Mutant," *Infection and Immunity* 49:225–237 (1985).
Gotoh et al., "Induction of Anticardiolipin Antibody and/or Lupus Anticoagulant in Rabbits by Immunization with Lipoteichoic Acid, Lipopolysaccharide and Lipid A," *Lupus* 5:593–597 (1996).
Del Prete et al., "Inhibition of Mononuclear Cell Procoagulant Activity by Lipophosphoglycan of *Leishmania donovani*," *Journal of Clinical Microbiology and Infection* 1:31–34 (1995).
Hatzigeorgiou et al., "Lipophosphoglycan from Leishmania Suppresses Agonist–Induced Interleukin 1 β Gene Expression in Human Monocytes via a Unique Promoter Sequence," *Proc. Natl. Acad. Sci. USA* 93:14708–14713 (1996).

* cited by examiner

*Primary Examiner*—Mark Navarro
(74) *Attorney, Agent, or Firm*—Nixon Peabody LLP

(57) ABSTRACT

The present invention relates to methods of treating inflammatory diseases, inhibiting production of adhesion molecules on endothelial cells, inhibiting production of nitric oxide synthase by macrophages, inhibiting production of tissue factor by endothelial cells, reversing the inhibitory effects of lipophosphoglycan on endothelial cells or macrophages, and targeting a material to endothelial cells, fibroblasts, or monocytes, by administering lipophosphoglycan or lipophosphoglycan analog. Also disclosed is an isolated DNA molecule suitable for connection to a gene capable of transcription where lipophophoglycan or lipophosphoglycan analogues bind to the DNA molecule and antagonizes transcription of the gene.

14 Claims, 38 Drawing Sheets

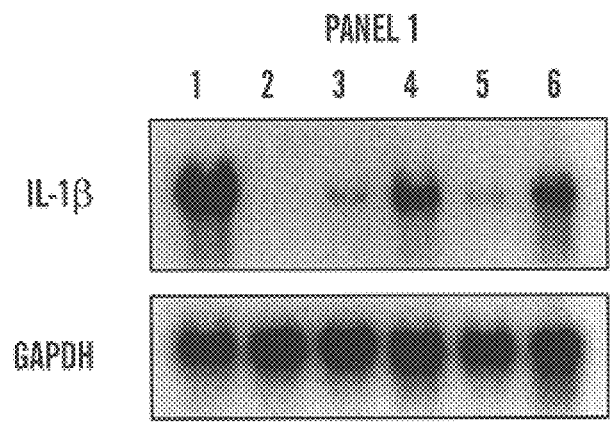
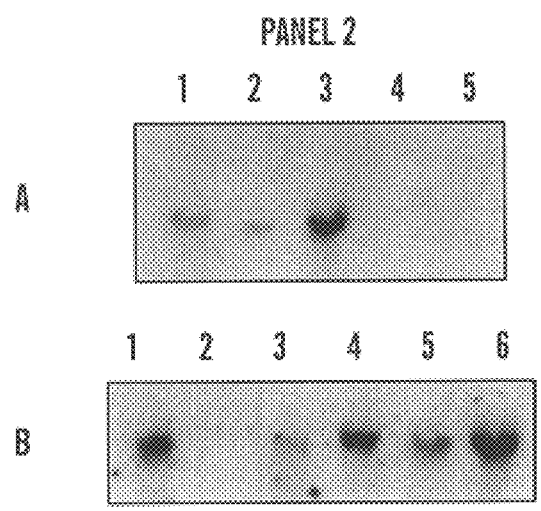
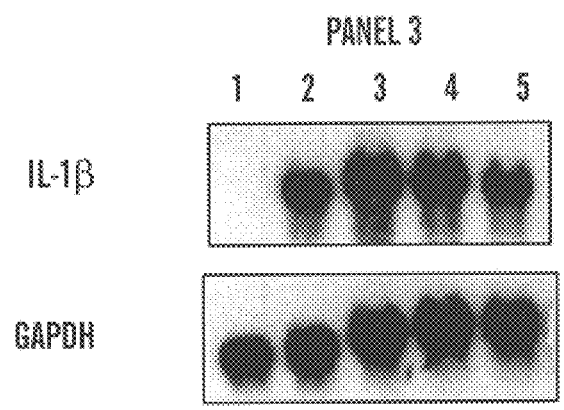
*FIG. 8*

1    2    3
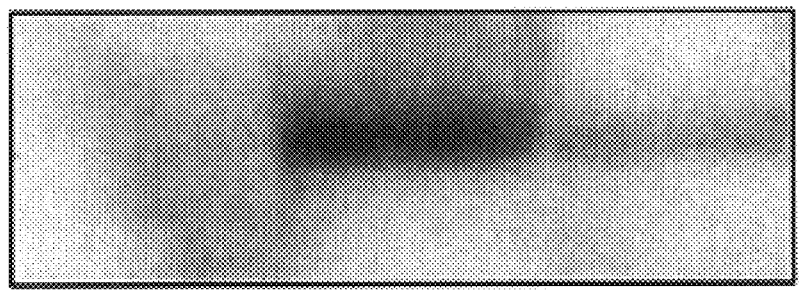
IL-1β
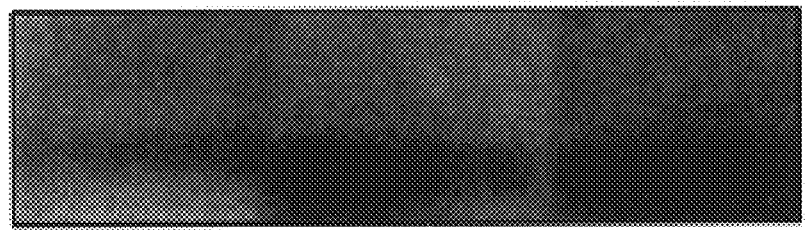
GAPDH
*FIG. 11*

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 327 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
CATTCTTCTA ACGTGGGAAA ATCCAGTATT TTAATGTGGA CATCAACTGC ACAACGATTG      60

TCAGGAAAAC AATGCATATT TGCATGGTGA TACATTTGCA AAATGTGTCA TAGTTTGCTA     120

CTCCTTGCCC TTCCATGAAC CAGAGAATTA TCTCAGTTTA TTAGTCCCCT CCCCTAAAAG     180

CTTCCACCAA TACTCTTTTT CCCCTTTCCT TTAACTTGAT TGTGAAATCA GGTATTCAAC     240

AGAGAAATTT CTCAGCCTCC TACTTCTGCT TTTGAAAGCT ATAAAAACAG CGAGGGAGAA     300

ACTGGCAGAT ACCAAACCTC TCCGAGG                                         327
```

(2) INFORMATION FOR SEQ ID NO:2:

(i) SEQUENCE CHARACTERISTICS:
      (A) LENGTH: 254 base pairs
      (B) TYPE: nucleic acid
      (C) STRANDEDNESS: single
      (D) TOPOLOGY: linear (ii) MOLECULE TYPE: DNA (genomic)

-continued (xi) SEQUENCE DESCRIPTION: SEQ ID NO:2:

```
CATTCTTCTA ACGTGGGAAA ATCCAGTATT TTAATGTGGA CATCAACTGC ACAACGATTG        60

TCAGGAAAAC AATGCATATT TGCATGGTGA TACATTTGCA AAATGTGTCA TAGTTTGCTA       120

CTCCTTGCCC TTCCATGAAC CAGAGAATTA TCTCAGTTTA TTAGTCCCCT CCCCTAAAAG       180

CTTCCACCAA TACTCTTTTT CCCCTTTCCT TTAACTTGAT TGTGAAATCA GGTATTCAAC       240

AGAGAAATTT CTCA                                                        254
```

(2) INFORMATION FOR SEQ ID NO:3:

(i) SEQUENCE CHARACTERISTICS:
  (A) LENGTH: 174 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:3:

```
CATTCTTCTA ACGTGGGAAA ATCCAGTATT TTAATGTGGA CATCAACTGC ACAACGATTG        60

TCAGGAAAAC AATGCATATT TGCATGGTGA TACATTTGCA AAATGTGTCA TAGTTTGCTA       120

CTCCTTGCCC TTCCATGAAC CAGAGAATTA TCTCAGTTTA TTAGTCCCCT CCCC            174
```

METHODS AND COMPOUNDS FOR TREATING AUTOIMMUNE AND VASCULAR DISEASE

This application claims the benefit of U.S. Provisional Patent Application Serial No. 60/011,406, filed Feb. 9, 1996.

This invention was made in part with Government support under Grant Nos. AI-16282 and AI-33322, MO1-00096, and AI-20941 from the National Institutes of Health. The Government has certain rights in the invention.

FIELD OF THE INVENTION

This invention relates to methods and novel compounds for treating autoimmune and vascular disease. In particular, the invention relates to the use of lipophosphoglycan and novel lipophosphoglycan analogs to treat these diseases.

BACKGROUND OF THE INVENTION

Pro-inflammatory cytokines, such as interleukin-1 (IL-1), tumor necrosis factor (TNF-α), and interleukin-6 (IL-6) are important mediators of sepsis, rheumatoid arthritis and reactive arthritis. They are also associated with other conditions such as atherosclerosis, progression of disease in persons infected with the human immunodeficiency virus, and autoimmune disorders. There were 250,000 reported cases of sepsis in the United States in 1987. Rheumatoid arthritis in the adult population is estimated at 1%, with an additional 1% of the population estimated to have reactive arthritis or juvenile rheumatoid arthritis. Therefore, pro-inflammatory cytokines play a direct role in the pathogenesis of conditions in nearly 3 million persons. Current therapeutic methods are not very effective in reducing the morbidity and/or mortality associated with these diseases.

Depressed cellular immunity and IL-1β production are associated with leishmaniasis caused by *Leishmania donovani*. *Leishmania donovani* is an obligate intracellular parasite of the mammalian macrophage. It is worldwide in distribution and annually causes disease in 20 million persons. The life cycle of Leishmania parasites consists of two stages. The flagellated promastigote form propagates in the alimentary tract of its insect vector (the sandfly) and develops into the infectious metacyclic promastigote stage. During the sandfly's blood meal, the metacyclic promastigotes are inoculated into the mammalian host. The promastigotes evade local host defense, disseminate, and enter macrophages throughout the reticuloendothelial system. Within macrophages they transform into the amastigote form which remains for the life of the new host. S. J. Turco and A. Descoteaux, "The Lipophosphoglycan of Leishmania parasites," *Annu. Rev. Microbiol.*, 46:65–94 (1992); J. L. Ho, R. Badaro, D. Hatzigeorgiou, S. G. Reed, and W. D. Johnson, Jr., "Cytokines in the Treatment of Leishmaniasis: From Studies of Immunopathology to Patient Therapy," *Biother.* 7:223–35 (1994).

The two poles of immune responses in patients infected with *L. donovani* are: 1) a delayed type hypersensitivity ("DTH") and CMI to Leishmania antigens which is associated with containment of infection, and 2) B cell activation with absence of DTH, and T-cell reactivity that is associated with visceral leishmaniasis ("VL"). J. L. Ho, R. Badaro, D. Hatzigeorgiou, S. G. Reed, and W. D. Johnson, Jr., "Cytokines in the Treatment of Leishmaniasis: From Studies of Immunopathology to Patient Therapy," Biother. 7:223–35 (1994). Patients with acute VL have both a functional T-cell defect with decreased production of IL-2 and IFN-γ in response to Leishmania antigens or mitogens, and a presumed monocytic defeat with decreased in vitro production of IL-1β and TNF-α in response to Leishmania systate, LPS, or Listeria. E. M. Carvalho, R. Badaro, S. Reed, W. D. Johnson, Jr., and T. Jones, "Absence of IFN-γ and IL-2 Production During Active Visceral Leishmaniasis," *J. Clin. Invest*, 76:2066–9 (1985). These defects are attributed either to Leishmania products, or to a predominance of the T helper-2 ("Th2") type of lymphocytes. S. J. Turco and A. Descoteaux, "The Lipophosphoglycan of Leishmania Parasites," *Annu. Rev. Microbiol.*, 46:65–94 (1992); P. Scott, "IFN-γ Modulates the Early Development of Th1 and Th2 Responses in a Murine Model of Cutaneous Leishmaniasis," *J. Immunmol.*, 147:3149–3155 (1991); K. Varkla, R. Chatelain, L. M. C. C. Leal, and L. Coffman, "Reconstitution of C.B-17 SCID Mice with BALB/c T cells Initiates a T Helper Type-1 Response and Renders Them Capable of Healing Leishmania Major Infection," *Eur. J. Immunol.* 23:262–268 (1992); C. L. Karp, S. H. El-Sagi, T. A. Wynn, M. M. H. Satti, H. M. Kordojani, F. A. Hashim, M. Hag-Ali, F. A. Neva, T. B. Nutman, and D. L. Sacks, "In vivo Cytokine Profiles in Patients with Kala-azar: Marked Elevation of Both Interleukin 10 and Interferon-gamma," *J. Clin. Invest.* 91:1644–8 (1993); H. G. Ghalib, M. R. Piuvezam, Y. A. W. Skeiky, M. Siddig, F. A. Hashim, A. M. El-Hassan, D. M. Russo, and S. G. Reed, "Interleukin 10 Production Correlates with Pathology in Human *Leishmania donovani* Infections," *J. Clin. Invest.* 92:324–9 (1993); L. Morris, A. B. Troutt, E. Handman, and A. Kelso, "Changes in the Precursor Frequencies of IL-4 and IFN-γ Secreting CD4+ Cells Correlate with Resolution of Lesions Inmurin Cutaneous Leishmaniasis," *J. Immunol.* 149:2715–2721 (1992); M. D. Sadick, F. P. Heinzel, B. J. Hodaday, R. T. Pu, R. S. Dawkins, and R. M. Locksley, "Cure of Murine Leishmaniasis with Anti-interleukin 4 Monoclonal Antibody; Evidence for a T cell-Dependent, Interferon-γ-independent Mechanism," *J. Exp. Med.* 171:115–127 (1990); L. M. Leal, D. W. Moss, R. Kuhn, W. Muller, and F. Y. Liew, "Interleukin-4 Transgenic Mice of Resistant Background are Susceptible to Leishmania Major Infection," *Eur. J. Immunol.* 23:566–5690 (1993).

One unique characteristic of Leishmania infection is that the macrophage is unable to kill the parasite. In macrophages infected with Leishmania or treated with lipophosphoglycan (LPG) of promastigotes of *L. donovani*, impaired macrophage functions including production of IL-1β have been reported. S. J. Turco and A. Descoteaux, "The Lipophosphoglycan of Leishmania Parasites," *Annu. Rev. Microbiol.* 46:65–94 (1992); T. B. McNeely and S. Turco, "Requirements of Lipophosphoglycan for Intracellular Survival of *Leishmania donovani* Within Human Monocytes," *J. Immunol.* 144:2745–50 (1992); S. Frankenburg, V. Leibovici, N. Mansbach, S. J. Turco, and G. Rosen, "Effect of Glycolipids of Leishmania Parasites on Human Monocyte Activity," *J. Immunol.* 145:4284–89 (1990); S. Frankenburg, A. Gross, and V. Leibovici, "*Leishmania major* and *Leishmania donovani*: Effect of LPG-containing and LPG-deficient Strains on Monocyte Chemotaxis and Chemiluminescence," *Exp. Parsitol.* 75:442–8 (1992); A. Descoteaux and G. Matlashewski, "C-fos and Tumor Necrosis Factor Gene Expression in *Leishmania donovani*-infected Macrophages," *Molecular Cell Biol.* 9:5223–7 (1989); N. E. Reiner, W. Ng, C. B. Wilson, R. McMaster, and S. K. Burchett, "Modulation of in vitro Monocyte Cytokine Response to *Leishmania donovani*. Interferon-γ Prevents Parasite-induced Inhibition of Interleukin-1 Production and Primes Monocytes to Respond to Leishmania by Producing Both Tumor Necrosis Factor-α and Interleukin-1," *J. Clin.*

Invest. 85:1914–240 (1990). Similarly, diminished macrophage activation and/or IL-1 production have been reported to Th-2 derived cytokines such as, IL-4, IL-6, and IL-10. Essner, R. K. Rhoades, W. H. Mcbride, D. L. Morton, and J. S. Economou, "IL-4 Down-regulates IL-1 and TNF Gene Expression in Human Monocytes," *J. Immunol.* 142:3857–61 (1989); J. L. Ho, S. H. He, M. J. C. Rios, and E. A. Wick, "Interkeukin-4 Inhibits Human Macrophage Activation by Tumor Necrosis Factor, Granulocyte-macrophage Colony Stimulating Factor and Interleukin-3 for Anti-leishmania Activity and Oxidative Burst Capacity," *J. Infect. Dis.* 165.344–51 (1992); D. H., Hatzigeorgiou, S. H. He, J. Sobel, A. Hafner, K. Grabstein, and J. L. Ho, "Interleukin-6 Down-modulates Cytokine-enhanced Antileishmanial Killing," *J. Immunol.* 151:3682–92 (1993); C. Bogdan, J. Paik, Y. Vodovotz, and C. Nathan, "Contrasting Mechanisms for Suppression of Macrophage Cytokine Release by Transforming Growth Factor-γ and Interleukin-10," *J. Biol. Chem.* 267:23301–8 (1992). IL-1β produced by macrophages and other antigen-presenting cells mediates T-cell activation and proliferation and triggers T-cell production of IL-2. M. Luqman, L. Greenbaum, D. Lu, and K. Bottomly, "Differential Effect of Interleukin 1 on Naive and Memory CD4+ T Cells," *Eur. J. Immunol.* 22:95–100 (1992); P. H. Stein and A. Singer, "Similar Co-stimulation Requirements of CD4+ and CD8+ Primary T Helper Cells: Role of IL-1 and IL-6 in Inducing IL-2 Secretion and Subsequent Proliferation," *Int. Immunol.* 3:327–35 (1992). In addition, IL-1 plays an obligate role in the in vivo induction of activated macrophages against intracellular Listeria and activates anti-Leishmania activity in vitro," H. W. Rogers, K. C. F. Sheehan, L. M. Brunt, S. K. Dower, E. R. Unanue, and R. D. Schreiber, "Interleukin 1 Participates in the Development of Anti-Listeria Response in Normal and SCID Mice," *Proc. Natl. Acad. Sci. USA*. 89:1011–15 (1992); D. Hatzigeorgiou, S. G. Reed, and W. D. Johnson, Jr., "Cytokines in the Treatment of Leishmaniasis: From Studies of Immunopathology to Patient Therapy," *Biother.* 7:223–35 (1994), which are hereby incorporated by reference. Therefore, inhibition of IL-1β production may be an important mechanism for evasion of CMI.

LPG, one of the most abundant surface molecules of the promastigotes but not synthesized by the amastigotes of *L. donovani*, plays a critical role for intramacrophage survival of promastigotes. S. J. Turco and A. Descoteaux, "The Lipophosphoglycan of Leishmania Parasites," *Annu. Rev. Microbiol.* 46:65–94 (1992). Although the production of IL-1β in response to LPS in human macrophages treated with LPG has been shown to be depressed, the molecular mechanisms remain undefined. S. Frankenburg, V. Leibovici, N. Mansbach, S. J. Turco, and G. Rosen, "Effect of Glycolipids of Leishmania Parasites on Human Monocyte Activity," *J. Immunol.* 145:4284–9 (1990). Furthermore, the mechanisms reported for *L. donovani*-maastigote-infected human macrophages differ from those reported for murine macrophages. N. E. Reiner, "Parasite Accessory Cell Interaction in Murine Leishmaniasis. Evasion and Stimulus-dependent Suppression of the Macrophage Interleukin 1 Response by *Leishmania donovani*," *J. Immunol.* 138:1919–25 (1987); N. E. Reiner, W. Ng, and W. R. McMaster, "Parasite-accessory Cell Interactions in Murine Leishmaniasis. II. *Leishmania donovani* Suppress Macrophage Expression of Class I and Class II Major Histocompatibility Gene Products," *J. Immunol.* 138:1926–32 (1987); N. E. Reiner, W. Ng, C. B. Wilson, R. McMaster, and S. K. Burchett, "Modulation of in vitro Monocyte Cytokine Response to *Leishmania donovani*. Interferon-γ Prevents Parasite-induced Inhibition of Interleukin-1 Production and Primes Monocytes to Respond to Leishmania by Producing Both Tumor Necrosis Factor-α and Interleukin-1," *J. Clin. Invest.* 85:1914–240 (1990).

SUMMARY OF THE INVENTION

The present invention relates to a method of treating inflammatory diseases in mammals. This process involves administering an effective amount of lipophosphoglycan or a lipophosphoglycan analogue to the mammal.

Another aspect of the present invention relates to a method of inhibiting production of adhesion molecules on endothelial cells. This process involves administering an effective amount of lipophosphoglycan to the endothelial cells.

The present invention also relates to inhibiting production of tissue factor by endothelial cells. This process involves administering an effective amount of lipophosphoglycan or lipophosphoglycan analogue to the endothelial cells.

A method of inhibiting induction of nitric oxide synthase by macrophages is also disclosed. This involves administering an effective amount of lipophosphoglycan or lipophosphoglycan analogue to macrophages.

A method of reversing the inhibitory effects of lipophosphoglycan on endothelial cells or macrophages is also disclosed. Here, an effective amount of lipophosphoglycan analogues are administered to endothelial cells or macrophages which are being contacted with lipophosphoglycan.

The present invention also relates to a method of targeting material to endothelial cells, fibroblasts, or monocytes. This involves administering lipophosphoglycan or lipophosphoglycan analogues to endothelial cells, fibroblasts, or monocytes. A product for such targeting is also disclosed.

Another aspect of the present invention relates to an isolated DNA molecule suitable for connection to a gene capable of transcription. Lipophosphoglycan or lipophosphoglycan analogues bind to the DNA molecule or trigger nuclear protein(s) binding to the DNA molecule.

Such binding antagonizes transcription of the gene. The DNA molecule, when positioned to regulate transcription of the gene, can be used to carry out a method of testing drugs for inhibiting production of tissue factor, nitric oxide synthase, proinflammatory cytokines, or adhesion molecules.

BRIEF DESCRIPTION OF THE DRAWINGS

FIG. 8 shows the specificity of LPG inhibition of induction of IL-1β. Panel 1 illustrates the effect of washing cells treated with LPG. Washing cells after exposure to LPG did not remove the inhibition of LPS-induction of IL-1β mRNA. THP-1 cells ($10^7$ per condition), pretreated or not with 1 or 2 μM LPG for 2 h, were washed twice by centrifugation (200×g, 5 min) and resuspended in medium containing or not containing 2 μg/ml LPS. Total RNA was extracted after 4 h and analyzed as described above for FIGS. 3–5. Representative autoradiography of Northern analysis demonstrating IL-1β and GAPDH and mRNA is illustrated, and treatment conditions are as follows: lane: 2, medium; lanes: 1 and 3 through 6, 2 μg/ml LPS; lanes 3 and 5, 2 μM LPG; lanes 4 and 6, 1 μM LPG; lanes 3 and 4 were not washed; and lanes 5 and 6 were washed after treatment with LPG. Panel 2 in FIG. 8 shows the effect of LPG on IL-1β induction by TNF-α (A) and PMA (B). LPG suppressed the induction of IL-1β mRNA by TNF-α but not by PMA. In row A, THP-1 cells pretreated for 2 h or not pretreated with 2 μM LPG were stimulated either with 50 ng/ml TNF-α for 2 h or with 2 μg/ml LPS for 4 h. Representative Northern analyses from 4 experiments are illustrated: lanes: 1, TNF-α; 2, TNF-α plus LPG; 3, LPS: 4, LPS plus LPG; and 5, LPG 2 μM. IL-1β was not detected in medium condition (data not shown). Representative Northern analyses are illustrated in row B for 3 separate experiments: IL-1β in THP-1 cells pretreated with medium not containing or containing 2 μM LPG for 1 h (lanes 2, 4, and 6) were stimulated either with 2 μg/ml LPS for 4 h (lanes 1 and 2) or with 25 ng/ml PMA (lanes 3 and 4) or 50 ng/ml PMA (lanes 5 and 6) for 4 h. Panel 3 shows the effect of LPG on IL-1β induction by S. epidermidis. LPG suppressed S. epidermidis induction of IL-1β but had no effect on steady state GAPDH mRNA. Illustrated is the autoradiogram of IL-1β or GAPDH mRNA from THP-1 cells after the following treatment conditions: lanes 1 and 4, pre-treatment for 2 h with 2 μM LPG; lane 5, simultaneous treatment with 2 μM LPG and S. epidermidis; lanes 1 and 2, 2 μg/ml LPS for 4 h; and lanes 3, 4, and 5, opsonized heat killed S. epidermidis at 10 particles per THP-1 cell.

FIG. 11 shows the effect of LPG on IL-1β mRNA transcription. LPG inhibited LPS-induced transcription of IL-1β but not GAPDH mRNA as demonstrated by the nuclear run-off assay. THP-1 cells incubated with medium or medium containing 2 μM LPG for 2 h were stimulated or not with 2 μg/ml LPS for 4 h. Nuclei isolated from these cells were used for in vitro transcription and $^{32}$P-labeled mRNA was detected by hybridization with IL-1β or GAPDH cDNA immobilized on nylon. Illustrated is the detection of IL-1β and GAPDH mRNA from one representative of 3 experiments: lanes 1, medium; 2, LPS; 3, LPG plus LPS.

Figure 12:
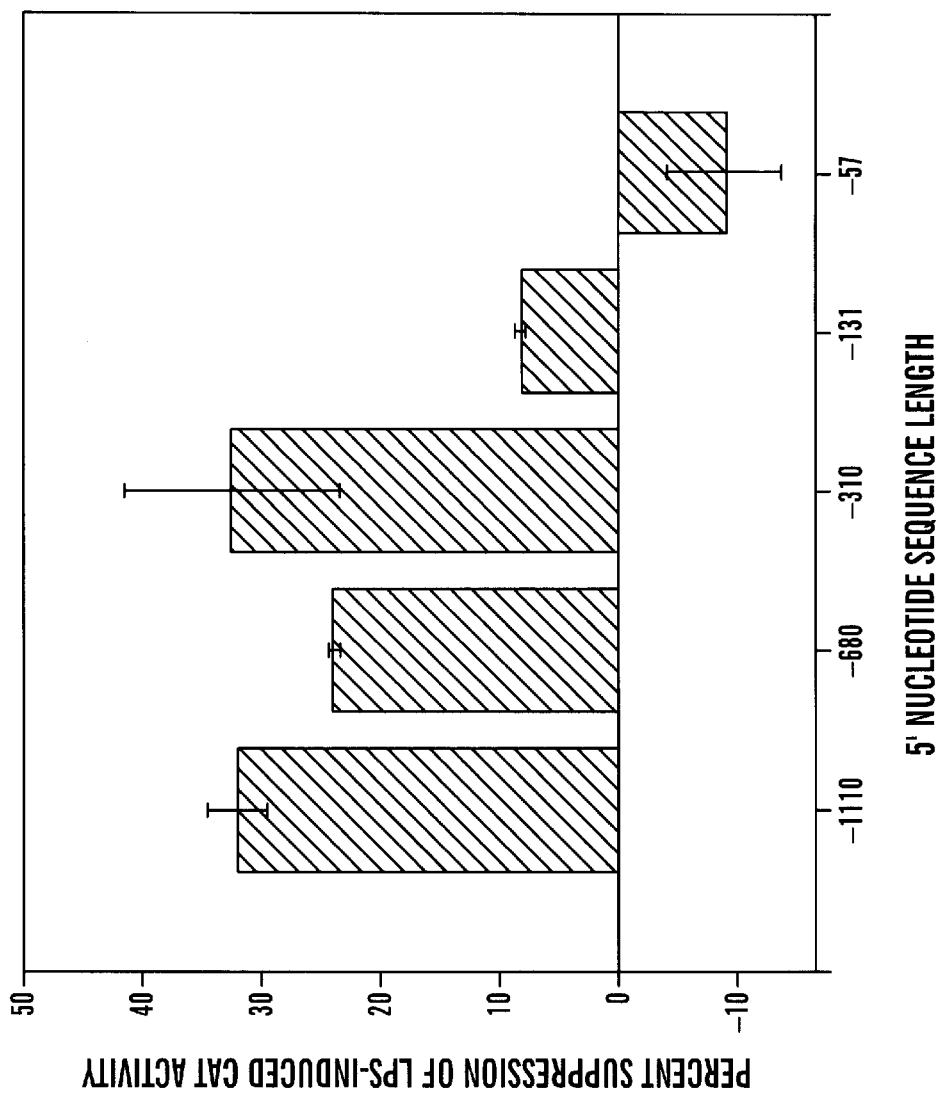

FIG. 12 shows the effect of LPG on promoter sequence regulation of IL-1β transcription. The major DNA element required for LPG suppression of LPS induction of CAT resided in the −310 to −57 nucleotide sequence of the IL-1β promoter region. THP-1 cells ($10^7$ per condition), pooled and sedimented in 50 ml tubes, were transiently transfected using a DEAE-Dextran method with plasmids (2–3 μg DNA per $10^7$ cells) containing the full length promoter sequence (−1110/+15) or plasmids containing the 5' deletion inserts indicted in FIG. 10. Cells were then plated and 36 h later were pretreated or not with 2 μM LPG for 2 h and stimulatd with LPS, 2 μg/ml for 20–24 h. CAT activity was measured in lysates containing equal amounts of protein, usually 100 μg for each condition. Acetylated and non-acetylated forms of $^{14}$C-chloramphenicol were separated using TLC in chloroform:methanol. TLC sheets were exposed to film and Phosphor Imager screen for quantitative analysis. Compared to medium, maximal induction by LPS of CAT activity was calculated based on the results from the Phosphor Imager Analyzer. The illustrated data are the mean of 4 to 6 separate experiments.

Figure 13A:
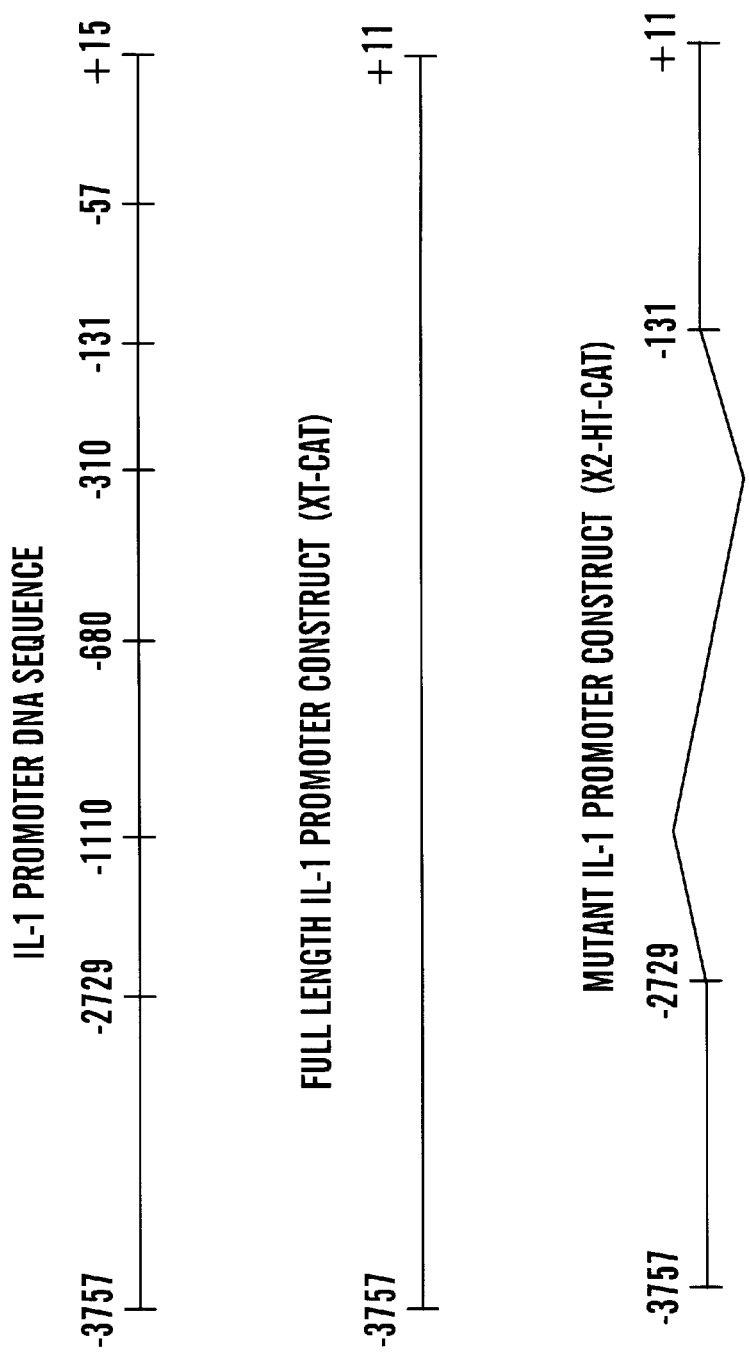
Figure 13B:
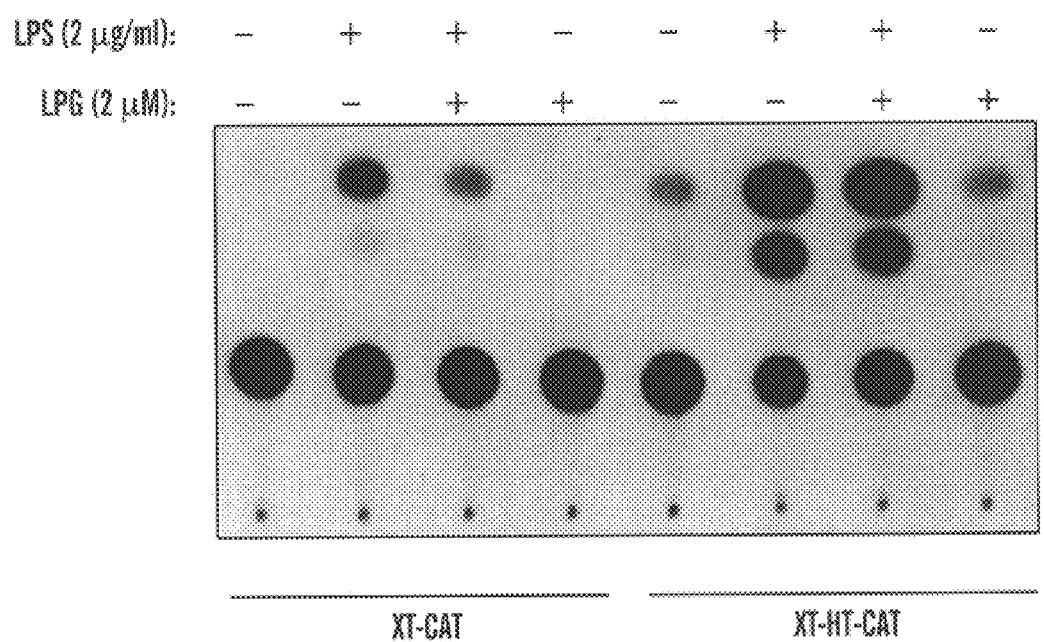

FIGS. 13A–B show the effect of LPG on a full-length IL-1β promoter sequence and the requirement for 310/−57 for LPG's inhibitory activity. LPG's inhibitory activity is observed using a plasmid containing nucleotide sequences −3757 to +11 (full-length) of the IL-1β promoter and is abrogated by deletion of the gene sequence from −2729 to −131 sequence. Illustrated are IL-1β promoter sequences and plasmid constructs (FIG. 13A) and a representative autoradiography of LPG's effect on IL-1β promoter activity (CAT assay) (FIG. 13B). THP-1 cells transiently transfected with plasmid containing the −3757/+11 (XT-CAT) or −3757 to −2729 linked to −131 to +11 (X2-HT-CAT) promoter sequence were treated with LPG (2 μM) for 2 h followed by challenge with 2 μg/ml LPS for 24 h. CAT activity was assayed for each condition and quantified by Phosphor Imager (N=5).

Figure 14:
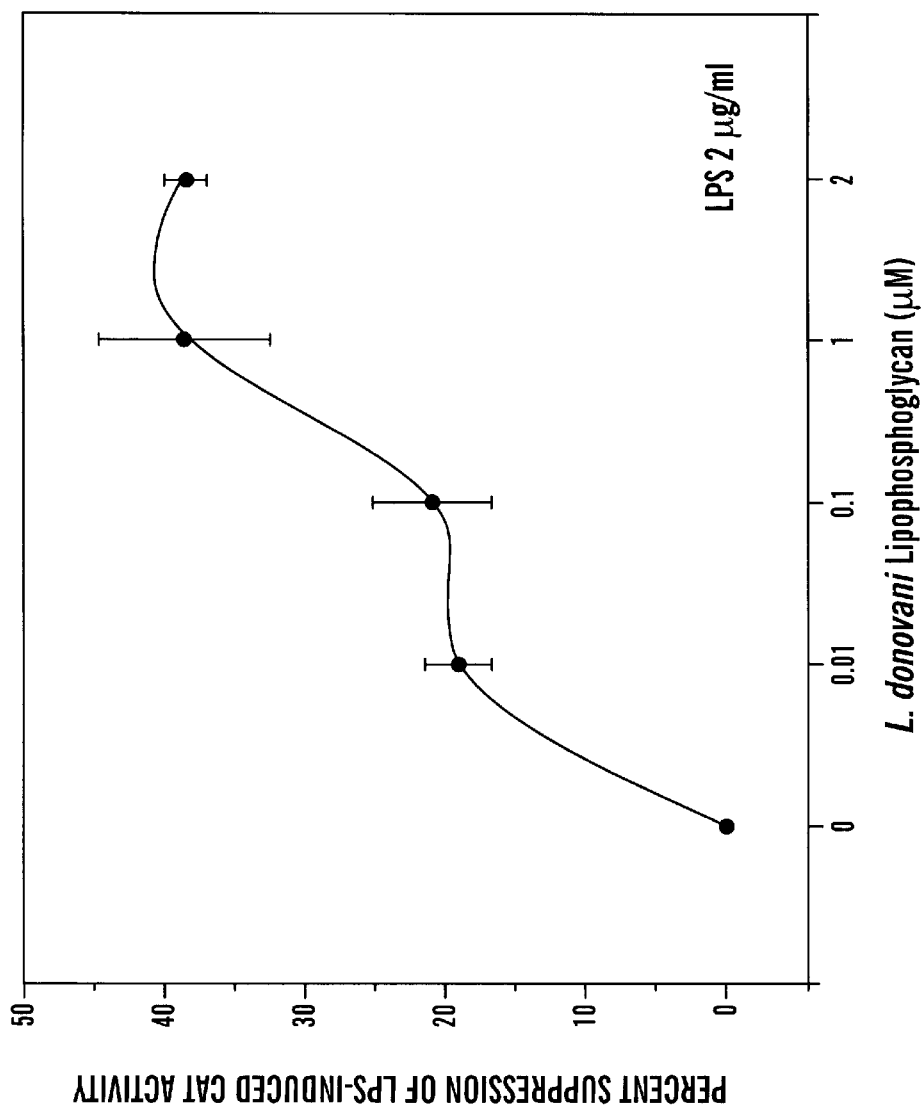

FIG. 14 shows the time- and dose-dependent effect of LPG on IL-1β promoter regulation. The profile of LPG suppression of LPS induction of the activity of CAT linked to IL-1β promoter sequences are similar to the profile of IL-1β mRNA under steady state conditions. To demonstrate the effect of varying dose LPG on LPS induction of CAT activity, THP-1 cells transiently transfected with plasmid containing the −310/+15 promoter sequence was cultured with medium or medium plus varying doses of LPG for 2 h followed by treatment with 2 μg/ml LPS for 24 h. The figure is the sum of 4 to 8 separate experiments for each time point.

Figure 15:
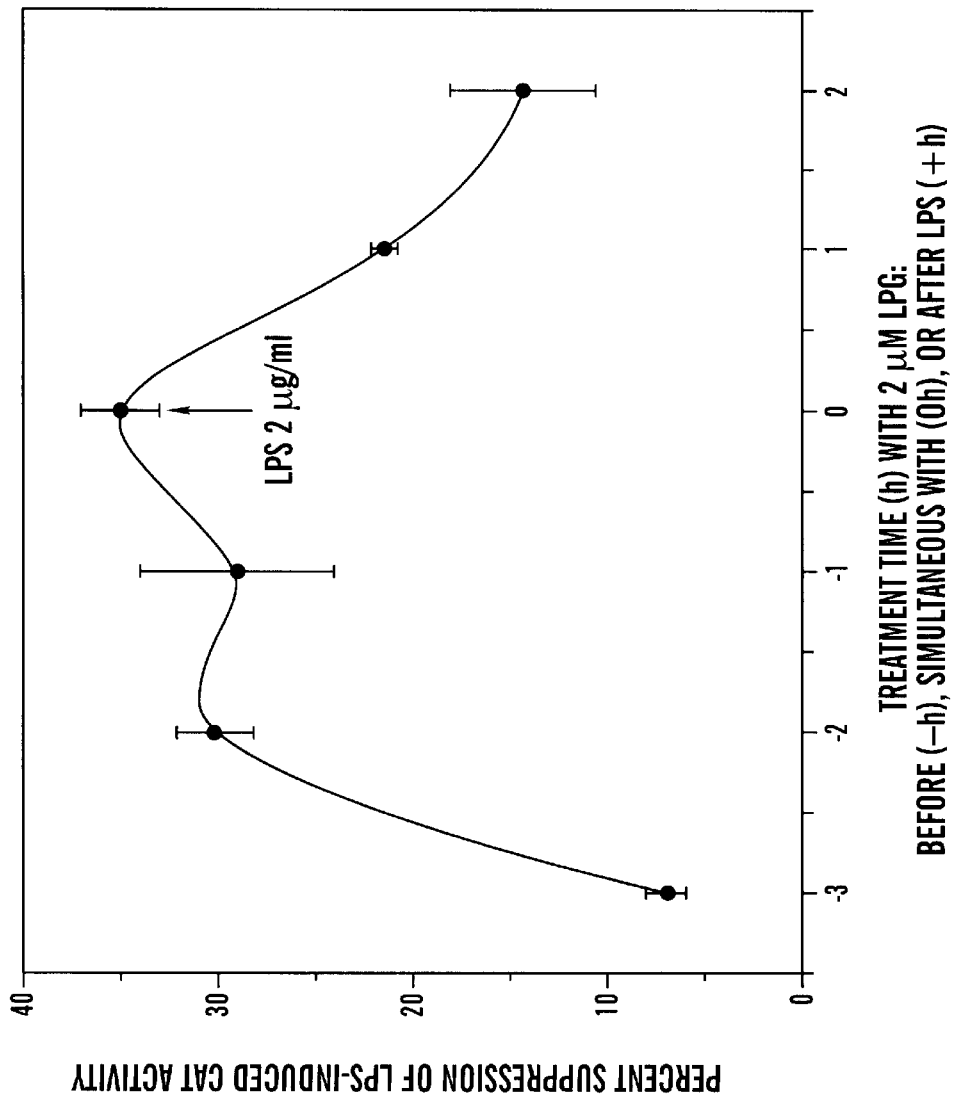

FIG. 15 illustrates the effect of time of LPG treatment on LPS induction of CAT activity. THP-1 cells transiently transfected with plasmid containing the −310/+15 promoter sequence linked to CAT gene were cultured with medium or medium plus 2 μM LPG for varying time before, simultaneous with or after treatment with 2 μg/ml LPS for 24 h. The figure is the sum of 3 to 5 separate experiments, for each time point.

Figure 16A:
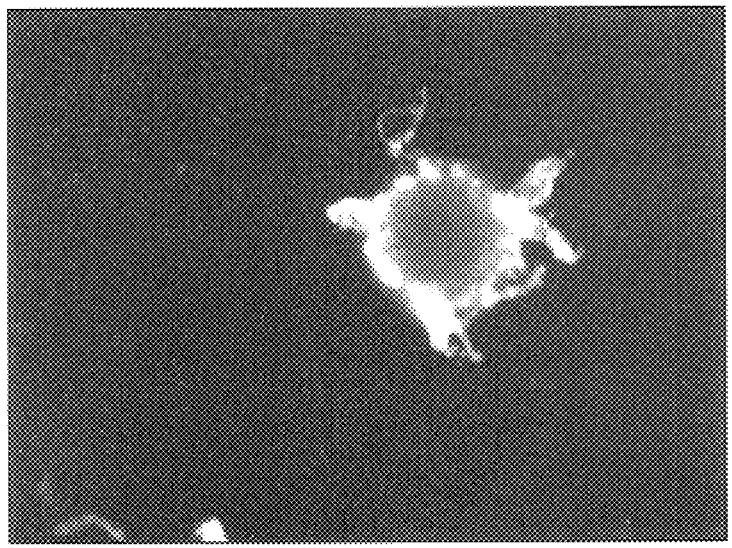
Figure 16B:
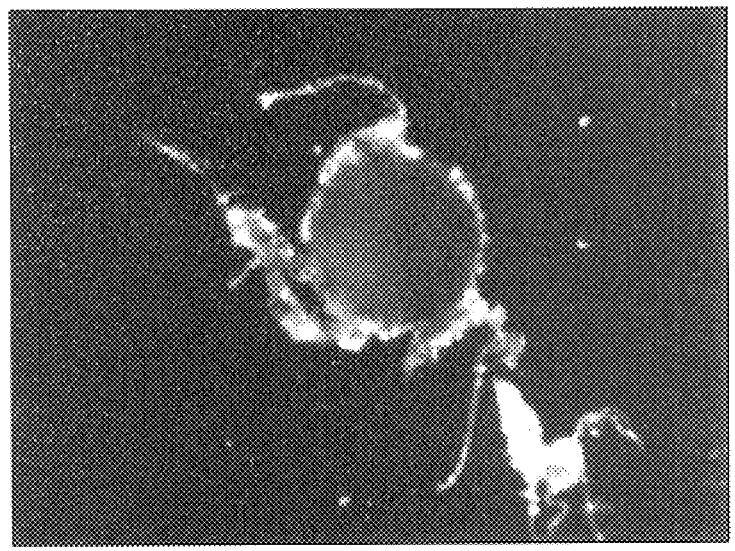
Figure 16C:

FIGS. 16A–C show binding of Leishmania promastigotes to human umbilical vein endothelial cells and THP-1 cells. Note that there was a transfer of LPG from the parasites to the endothelial cells and THP-1 cells (a representative of three separate experiments). FIG. 16A: HUVEC were exposed to Leishmania promastigotes for 2 h; FIGS. 16B and 16C: HUVEC and THP-1 cells were exposed respectively, to Leishmania for 1 h. HUVEC and THP-1 cells were exposed to Leishmania promastigotes at a ratio of 40 parasites to one vascular cell (15 min to 2 h, at 25° C.) followed by 2× washing to remove unbound parasites. Vascular cells with attached promastigotes were fixed, washed, and treated with monoclonal anti-LPG antibody (CA7AE) at 1:2,000 dilution. Following washing, bounded anti-LPG antibody was detected by incubation with FITC-labelled anti-IgM antibody (10 μg/ml) and observation under a fluorescent microscope.

Figure 17:
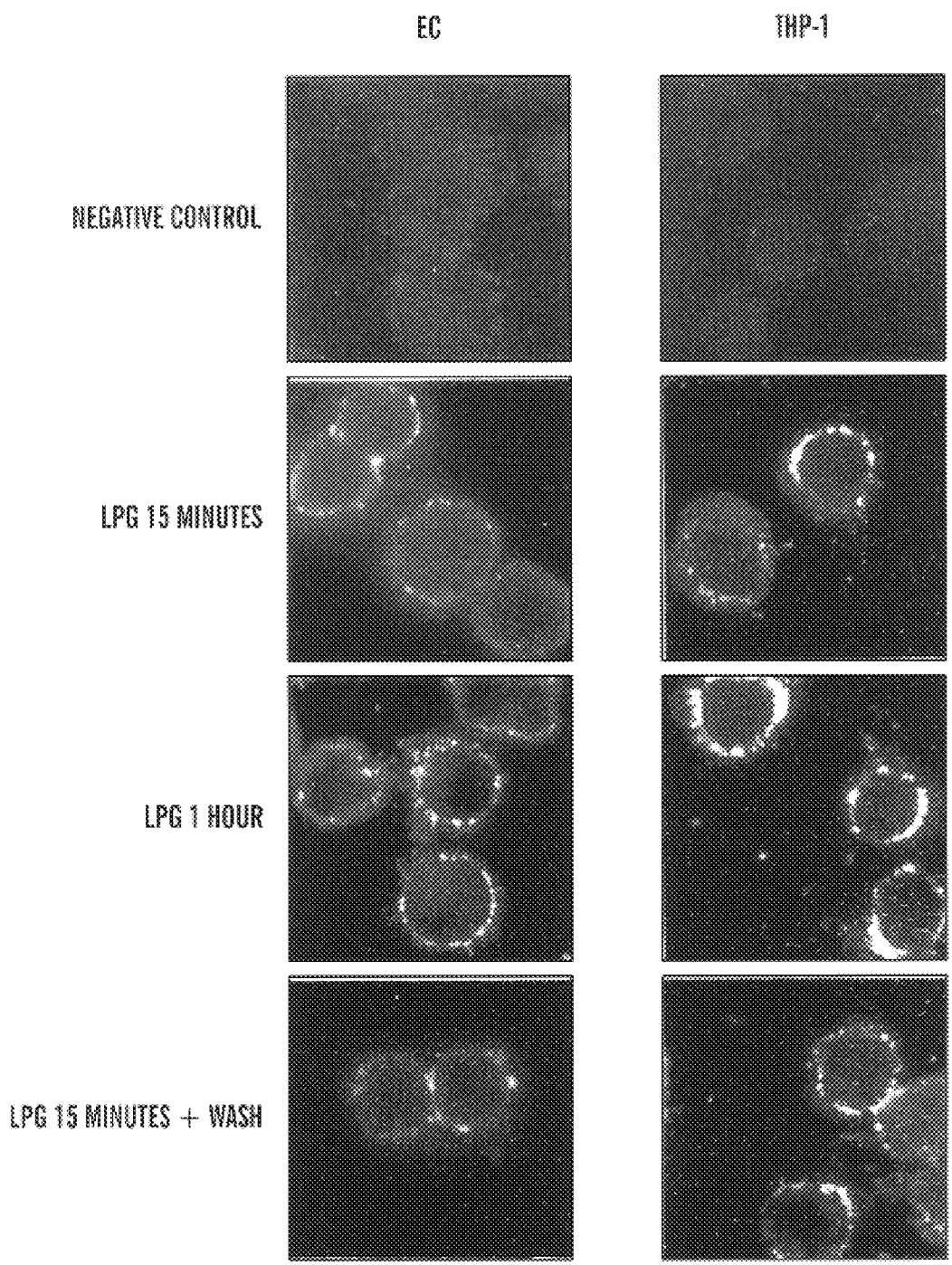

FIG. 17 shows an indirect immunofluorescence analysis of LPG binding to human umbilical vein endothelial cells and THP-1 cells. Cells were exposed to LPG (1 μM) for varying times, washed, and treated with monoclonal anti-LPG antibody (CA7AE) at 1:2,000 dilutions. Following washing, bounded anti-LPG antibody was detected by incubation with FITC-labelled anti-IgM antibody (10 μg/ml) and observation under a fluorescent microscope. Panels are: Negative control, LPG treatment for 15 min, LPG treatment for 1 h, and LPG treatment for 15 min followed by washing and re-incubation for 1 h (a representative of two separate experiments).

Figure 18:
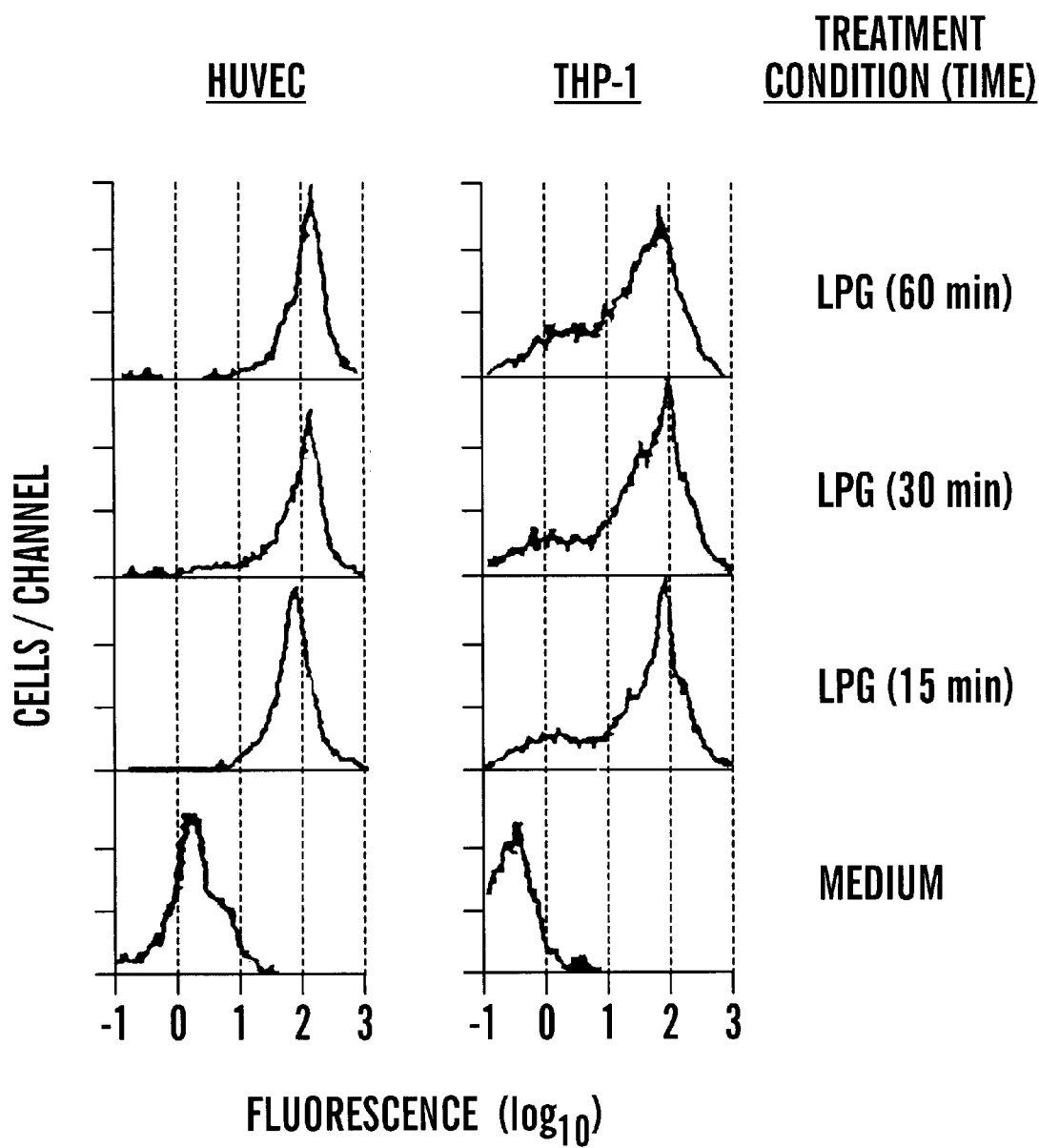

FIG. 18 depicts FACS analysis of LPG binding to endothelial cells and monocytic THP-1 cells. Cells were exposed to LPG (1 μM) for varying times. Washed and bound anti-LPG antibody was detected by incubation with FITC-anti-IgM antibody (10 μg/ml) and analyzed by flow cytometry (a representative of four separate experiments).

Figure 19:
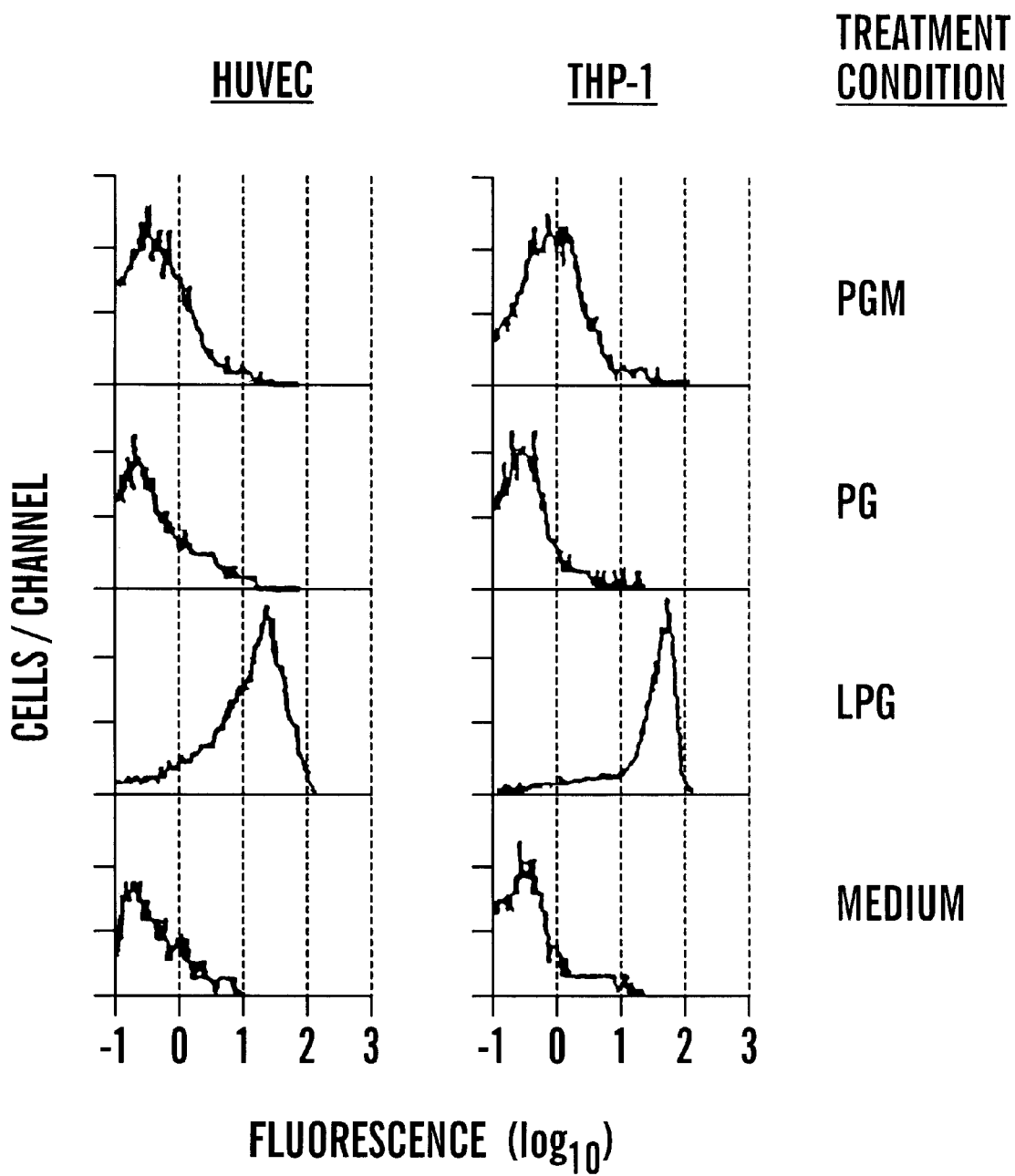

FIG. 19 depicts FACS analysis of LPG fragments binding to endothelial cells and THP-1 cells. Cells were exposed to LPG fragments (1 μM) for 1 h, washed and bound anti-LPG antibody (CA7AE recognizes only the repeating phosphogalactosyl-mannose disaccharide (PGM) domain of LPG) was detected by incubation with FITC-labelled anti-IgM antibody (10 μg/ml) and analyzed by flow cytometry. LPG (1 μM) was used as a positive control. The LPG fragments examined included: PG, consisting of cap-repeating phosphodisaccharides galactosyl-mannose and phosphosaccharide core; PGM, repeating phosphosaccharides galactosyl-mannose; core-PI, phosphosaccharide core-lyso-alkyl-phosphatidylinositol; and lyso-PI, lyso-alkyl-phosphatidylinositol (a representative of three separate experiments).

Figure 20A:
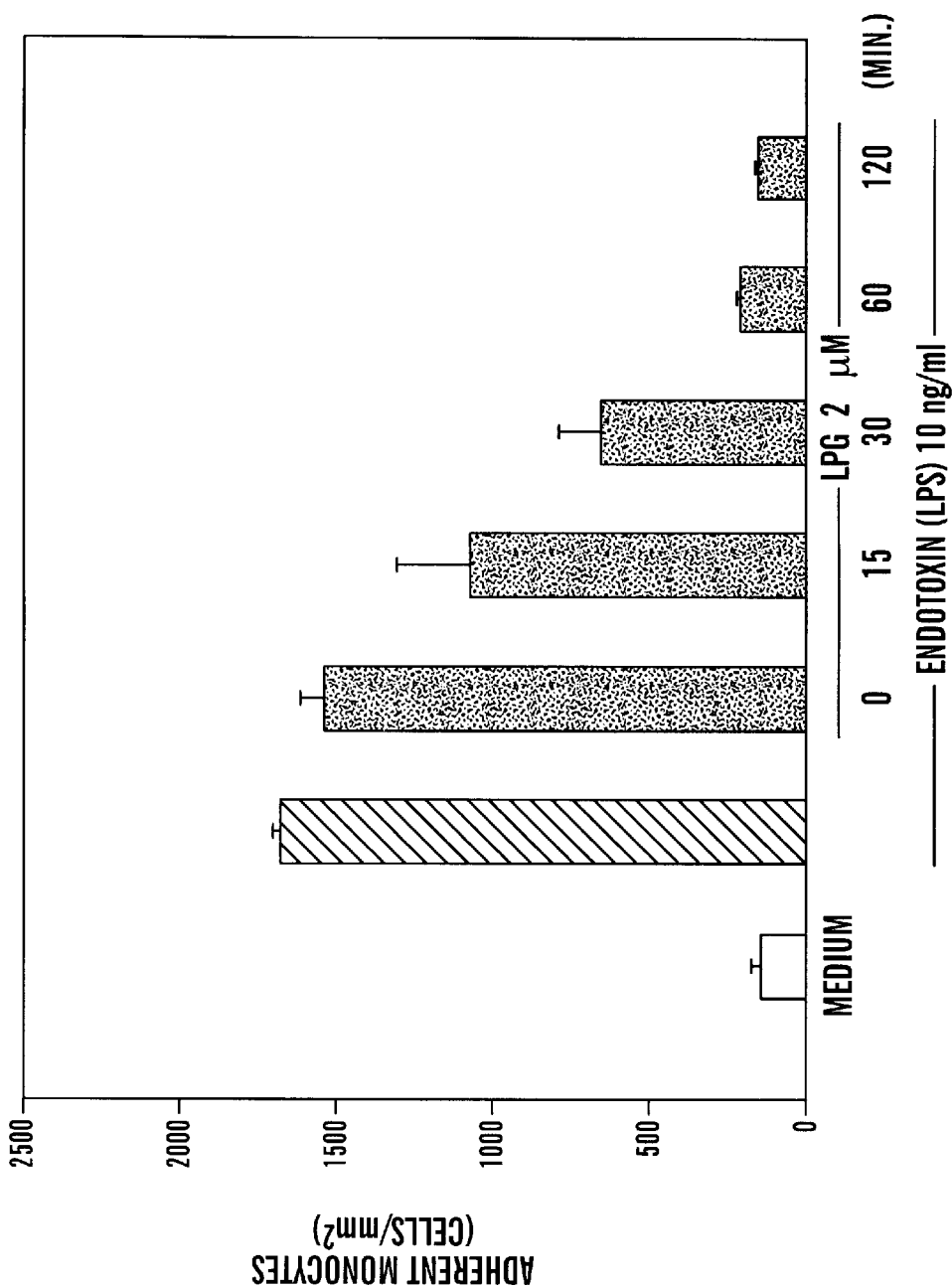
Figure 20B:
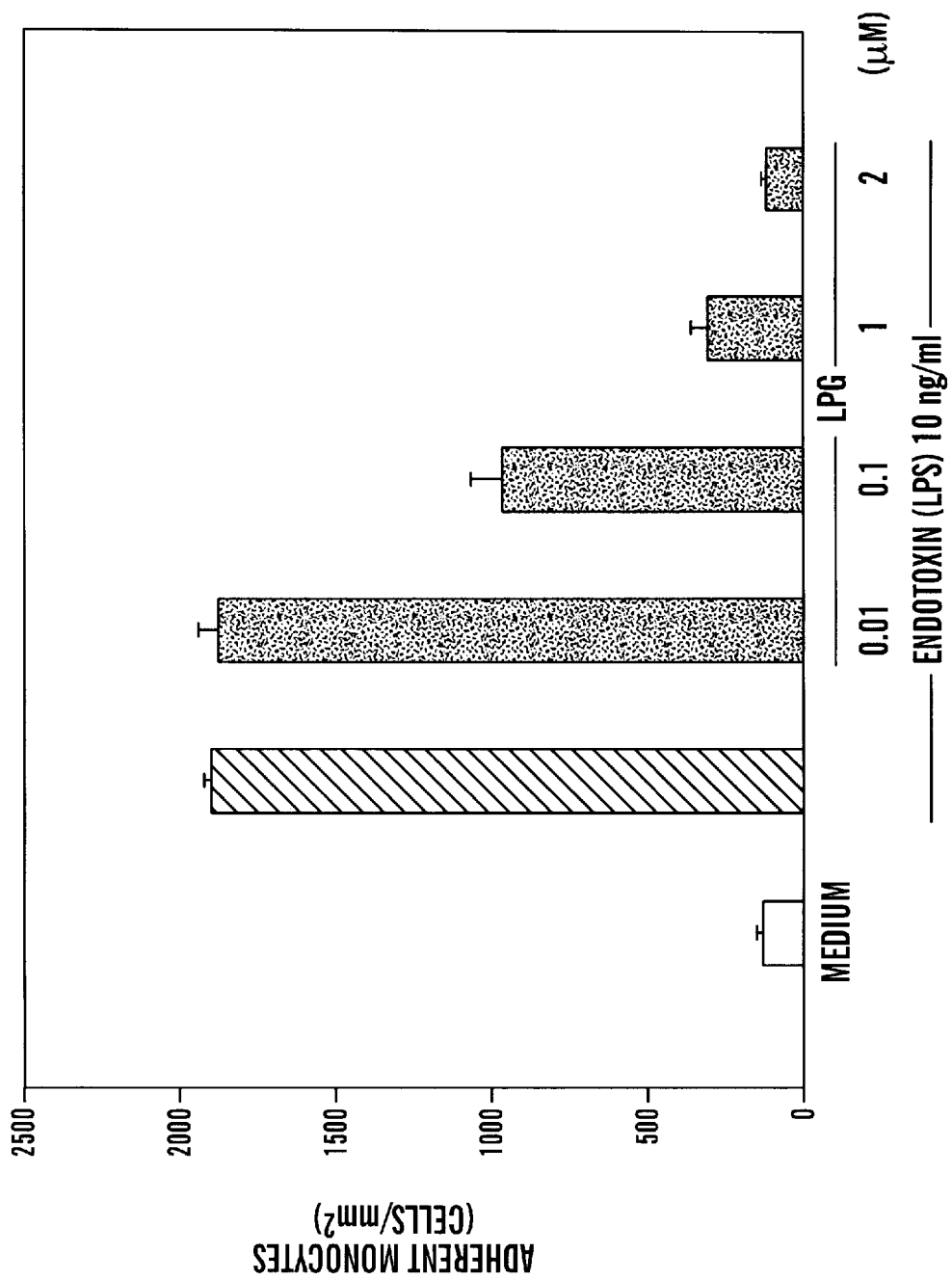
Figure 20C:
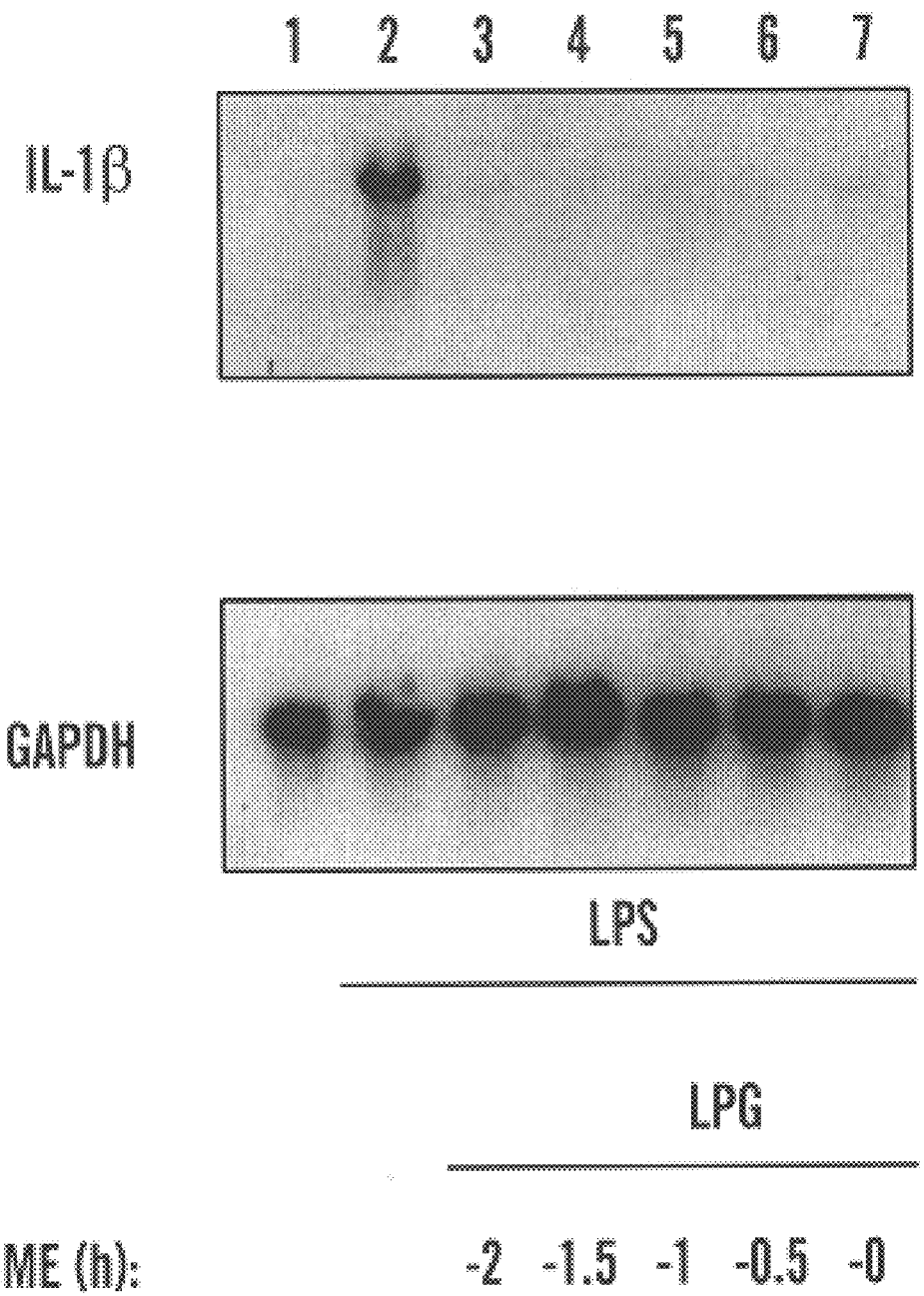

FIGS. 20A–C show the inhibitory effects of LPG on endotoxin-mediated endothelial cell adhesion and expression of IL-1β in THP-1 cells. FIG. 20A: Effect of LPG treatment time, and FIG. 20B: Effect of LPG doses. Endothelial cells were pretreated with LPG (doses and times as indicated in the FIG.) at 37° C., followed by endotoxin (10 ng/ml) challenge for 4 h at 37° C. Cell adhesion was measured by adding monocytic cells (MM6, 1×10$^6$ cells) onto the endothelial monolayer. Adhesion was carried out for 20 min and unbound cells were removed by washing. Bound MM6 cells per mm$^2$ of endothelial cell monolayer were enumerated by counting of 4 to 5 separate areas of the monolayer (means ±SE of 3 separate experiments in triplicates). FIG. 20C: Effect of varying treatment times of LPG (1 μM) on IL-1β steady-state mRNA expression in THP-1 cells as measured by Northern blot analysis. GAPDH was used as a control transcript and positive control includes the use of endotoxin (2 μg/ml, 4 h).

Figure 21:
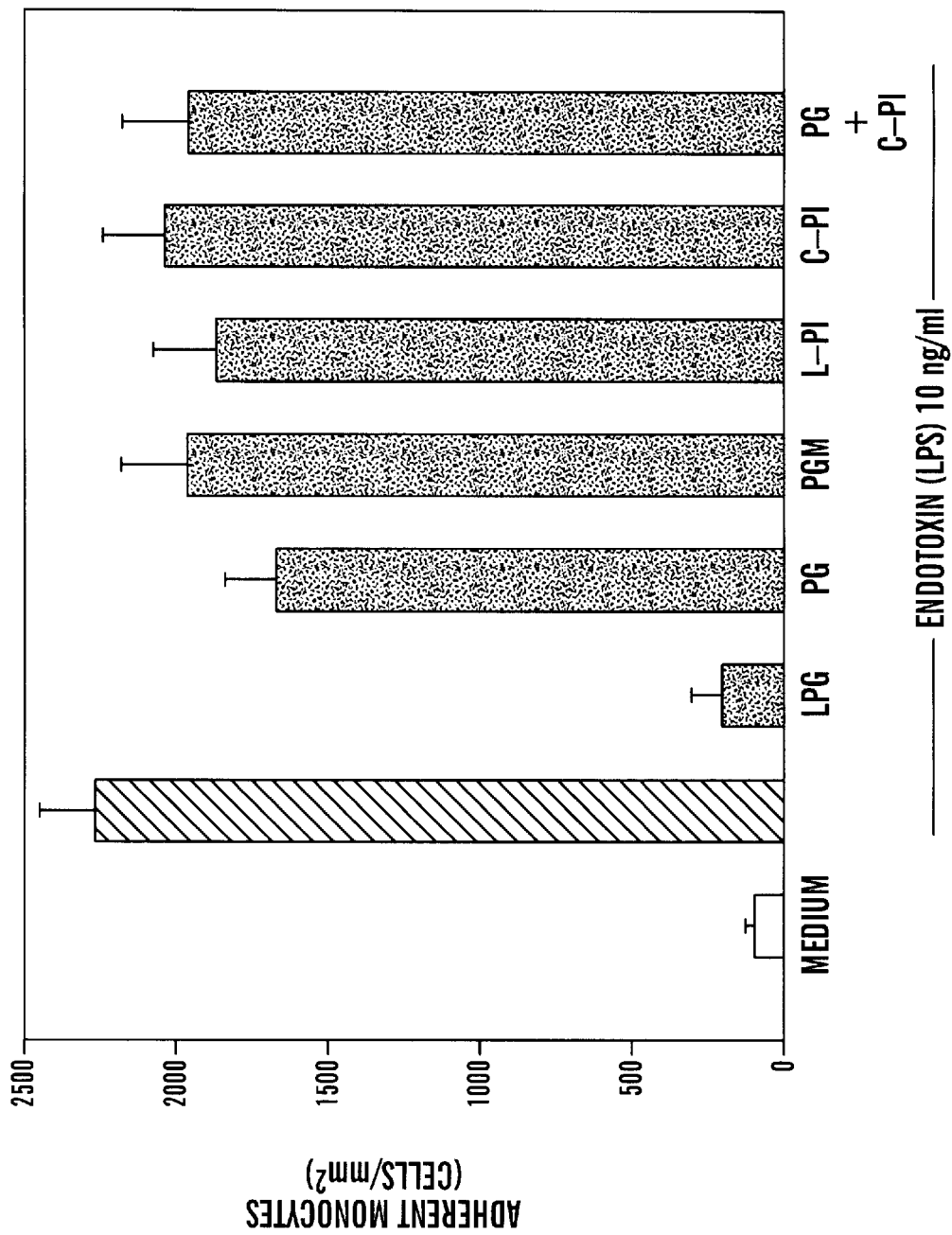

FIG. 21 shows the effects of LPG fragments on endotoxin-mediated endothelial cell adhesion. Human vascular endothelial cells were pretreated with LPG fragments (2 μM) for 1 h prior to the challenge with endotoxin (10 ng/ml) for a subsequent incubation period of 4 h. Endothelial adhesion to monocytic cells was measured as described in Example 16. Note that LPG fragments had no inhibitory activity (means ±SE, three separate experiments).

Figure 22A:
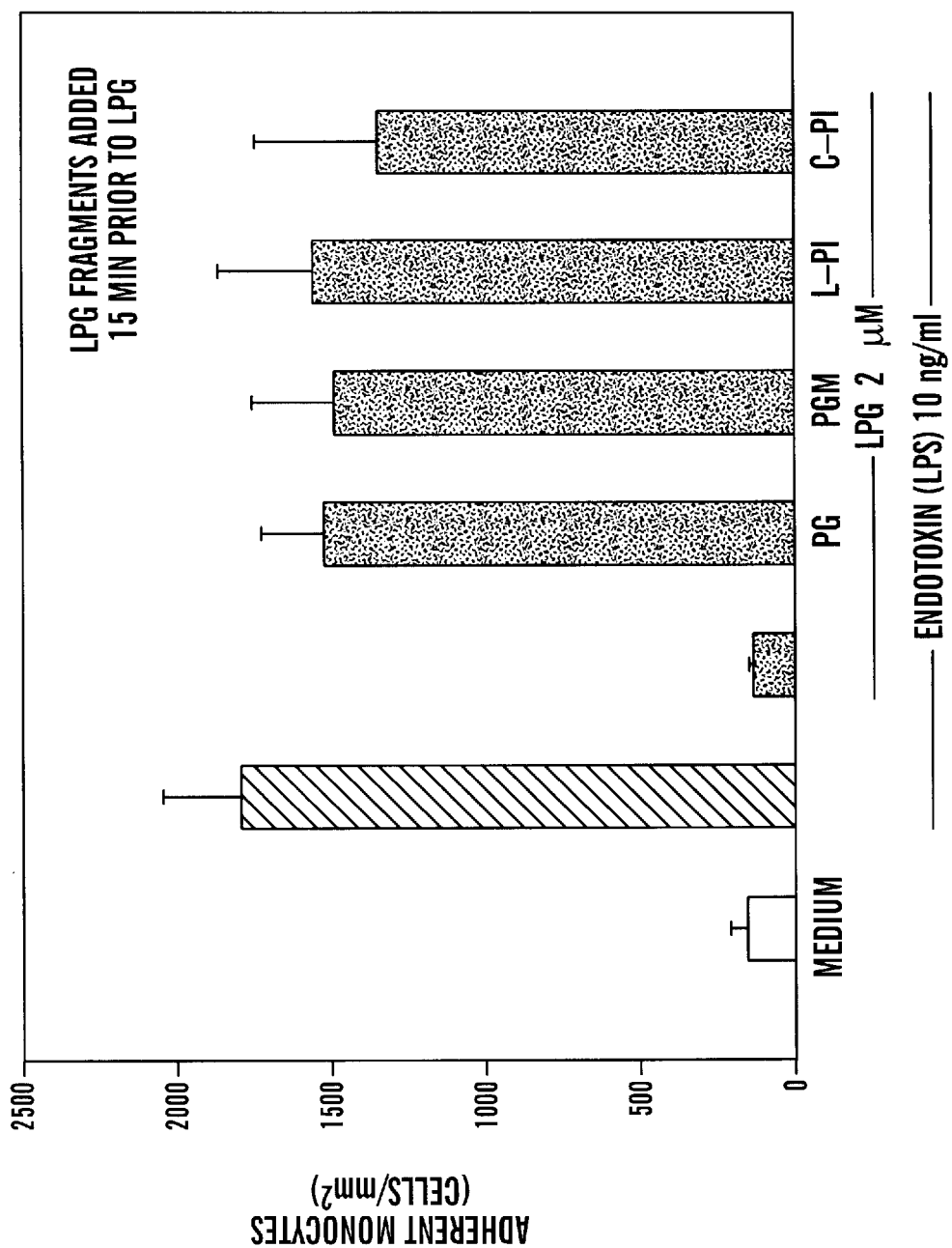
Figure 22B:
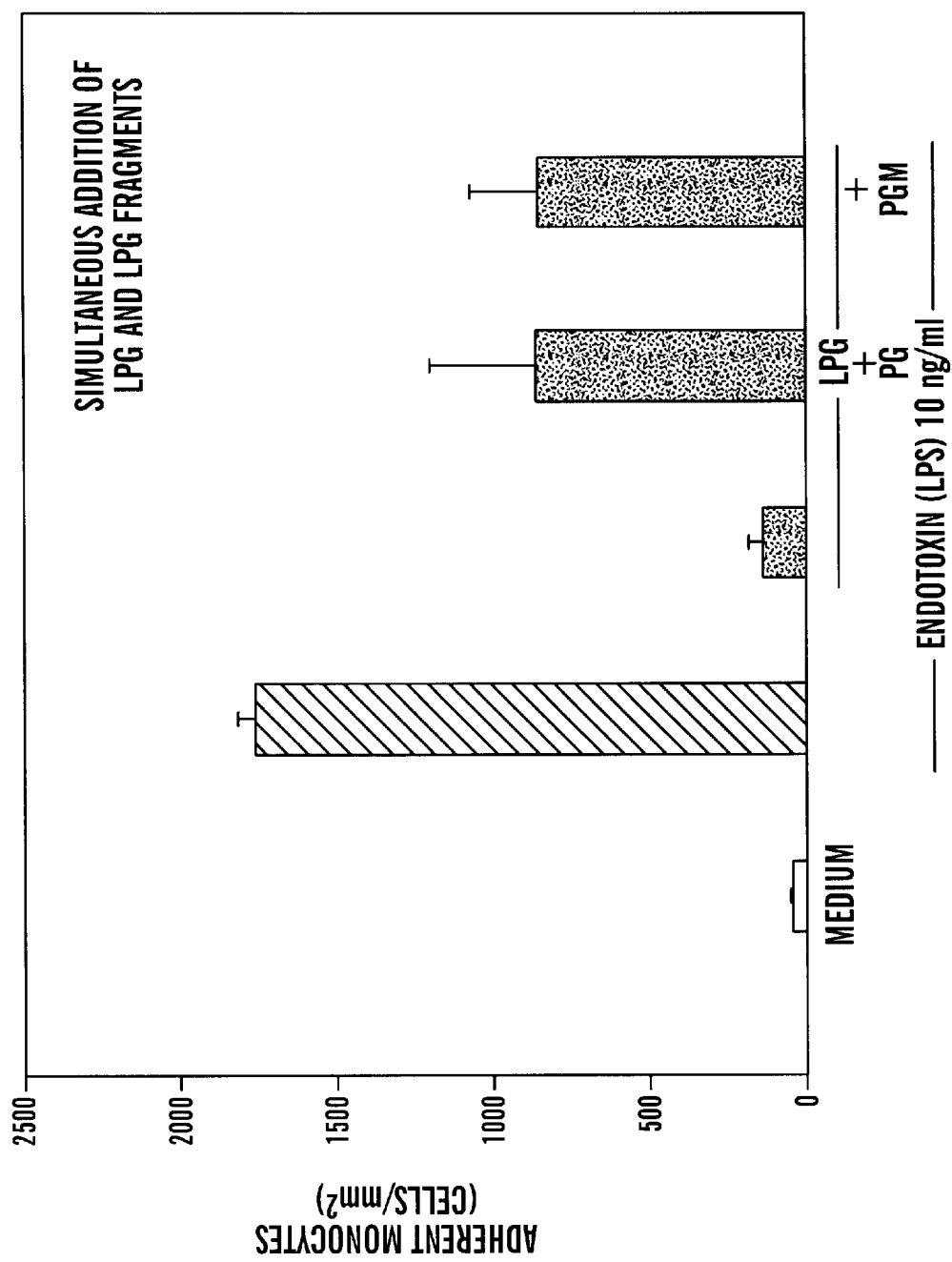
Figure 22C:
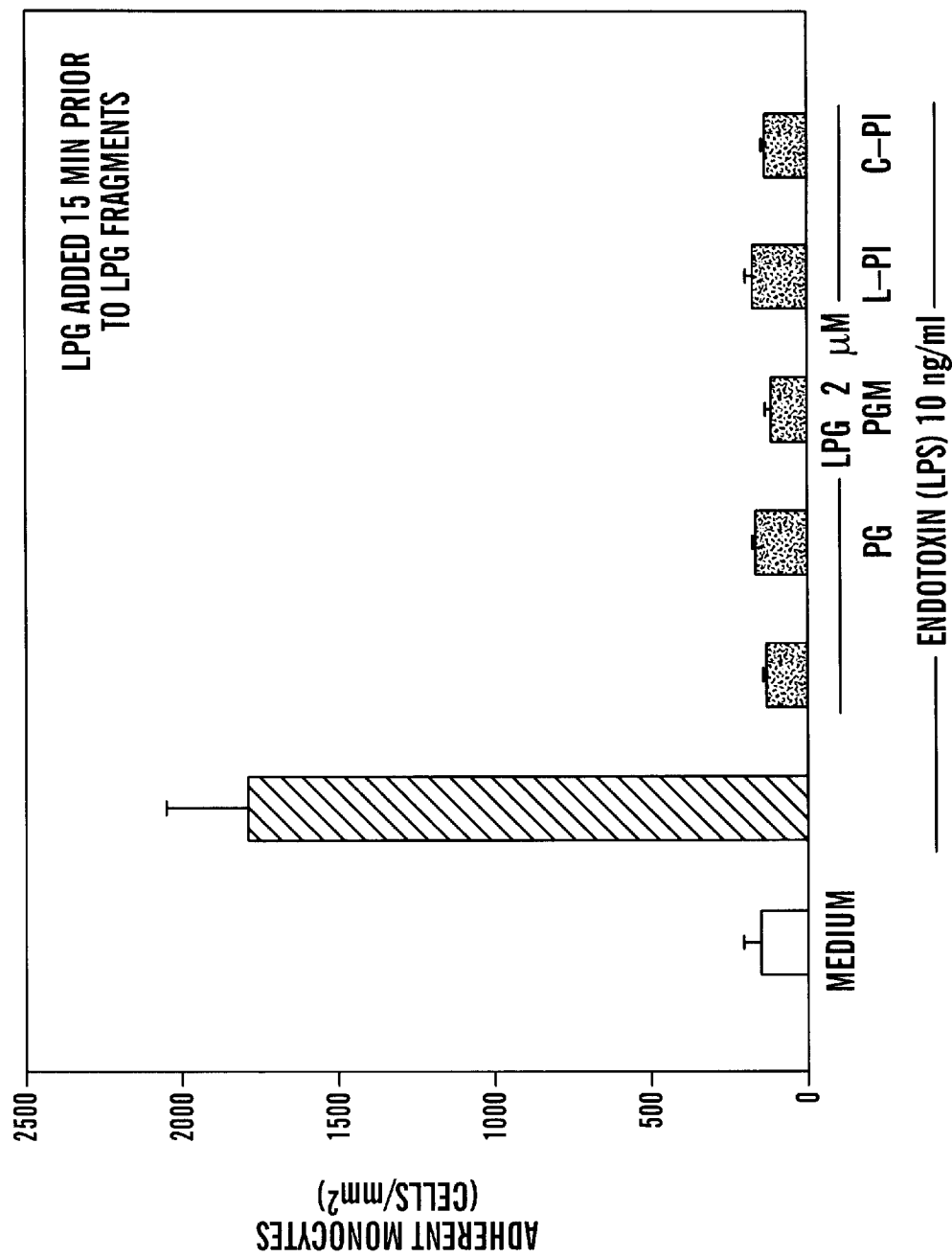

FIGS. 22A–C show the reversal effects of LPG fragments on intact LPG's inhibitory activity in endothelial cells. Endothelial cells were pretreated with intact LPG and LPG fragments in the following three conditions. FIG. 22A: Endothelial cells were pretreated with LPG fragments (10 μM) for 15 min at 37° C. prior to the addition of intact LPG (1 μM); FIG. 22B: LPG fragments (10 μM) were added simultaneously with the intact LPG (1 μM); FIG. 22C: LPG fragments (10 μM) were added 15 min after the addition of intact LPG (1 μM). The ability of LPG fragments to reverse the intact LPG's inhibitory activity in endothelial cells was monitored by endotoxin-mediated endothelial adhesion to monocytic cells (MM6). Results are means ±SE of 3–5 separate experiments.

Figure 23A:
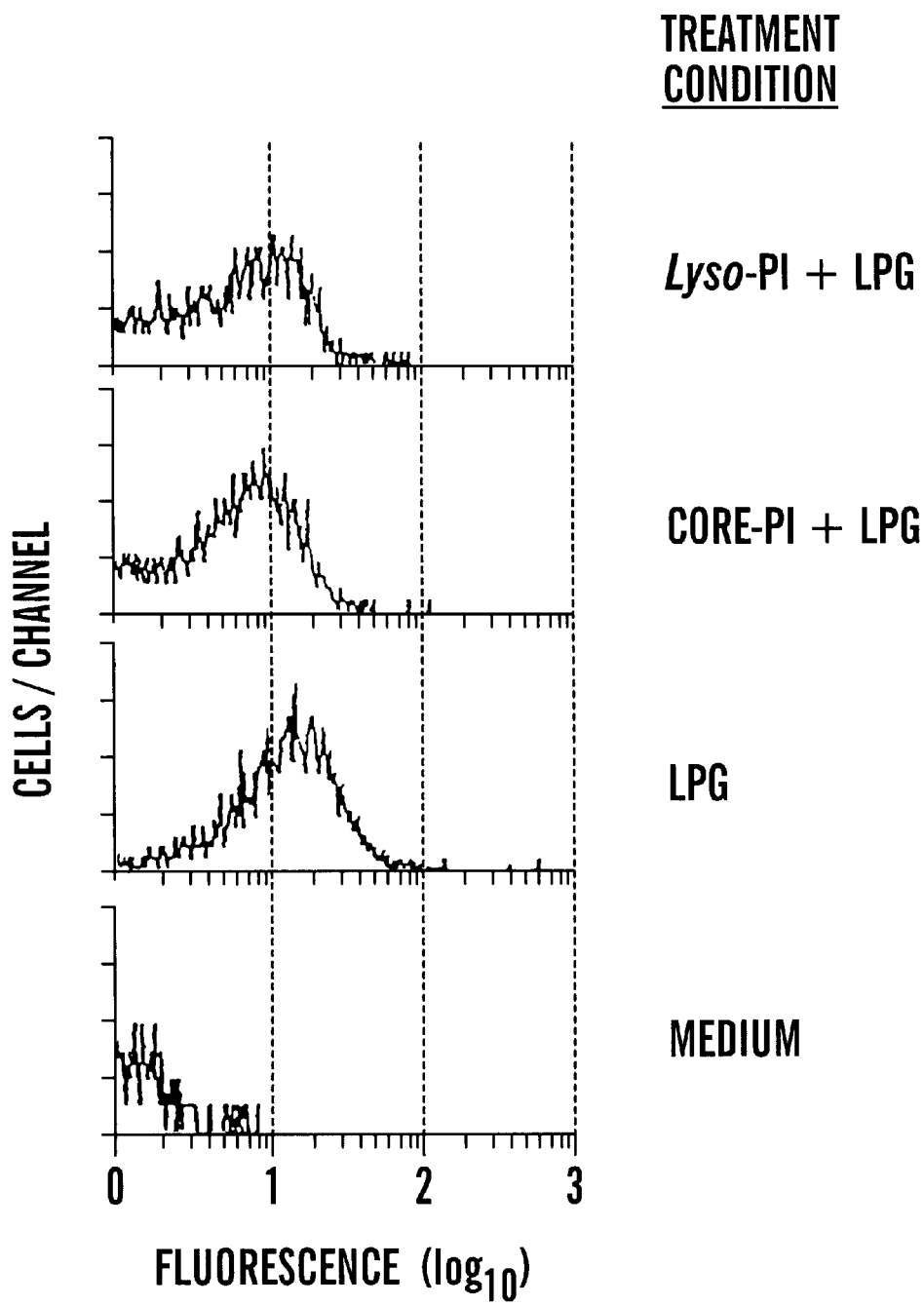
Figure 23B:
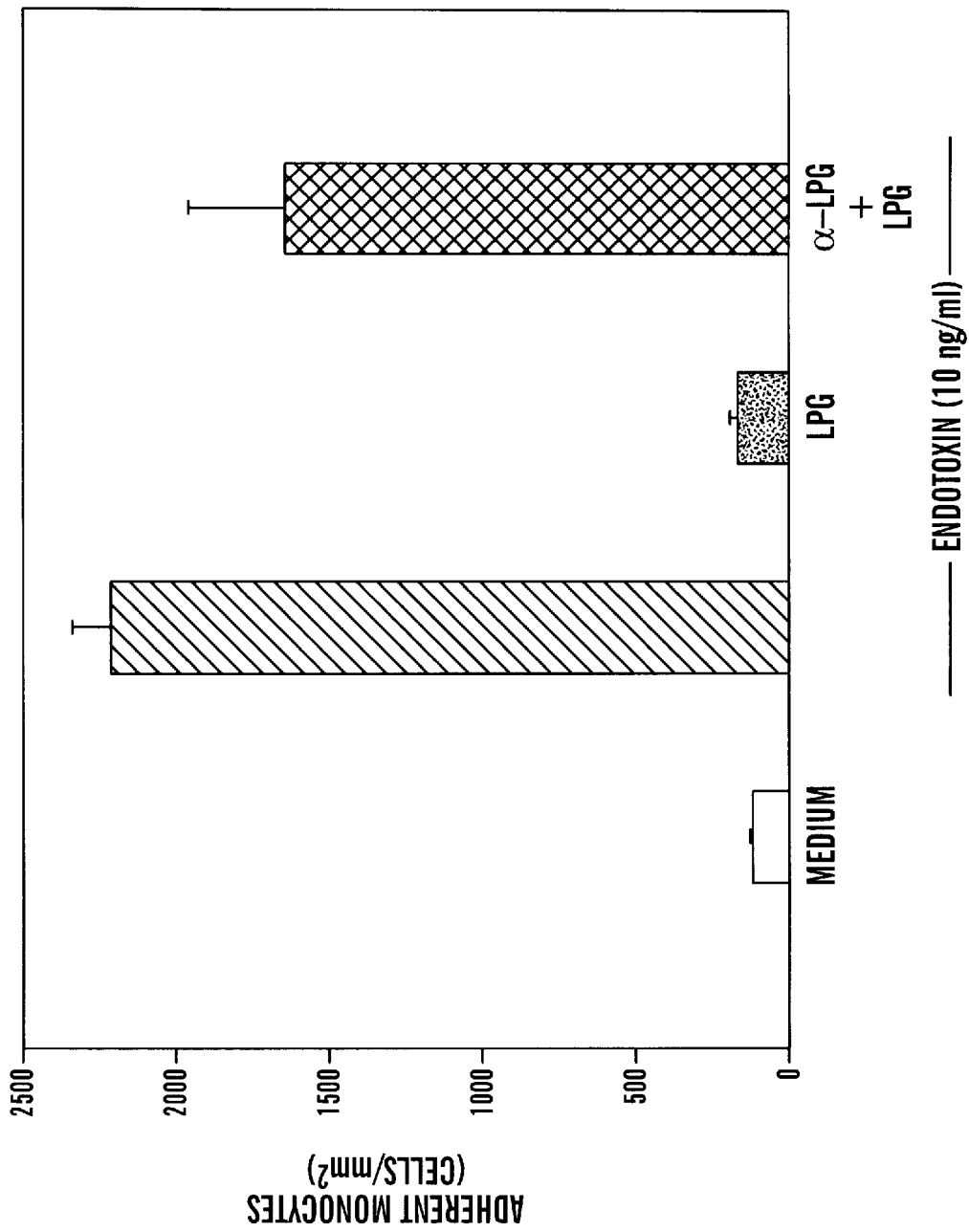

FIGS. 23A–B show Lyso-PI and core-PI competed the LPG binding and anti-LPG mAb reversed the LPG's cell inhibitory effects. FIG. 23A: Competition for LPG binding by lyso-PI and core-PI. Endothelial cells detached by mild collagenase treatment were incubated with lyso-PI and core-PI fragments (10 μM, 15 min, 37° C.) before addition of LPG (1 μM, 15 min., 37° C.). LPG (1 μM, 15 min., 37° C.) treatment alone was used for comparison. Cells were washed, treated with an anti-LPG mAb (CA7AE, 1:2,000 dilution), and prepared for FACS analysis. FIG. 23B: Reversal of LPG's inhibitory activity by anti-LPG mAb. LPG was incubated with an anti-LPG mAb for 15 min at 37° C. prior to the addition onto endothelial cells in the endothelial adhesion assay. An isotypic murine IgM mAb (10 μg/ml) was used as a control.

Figure 24:
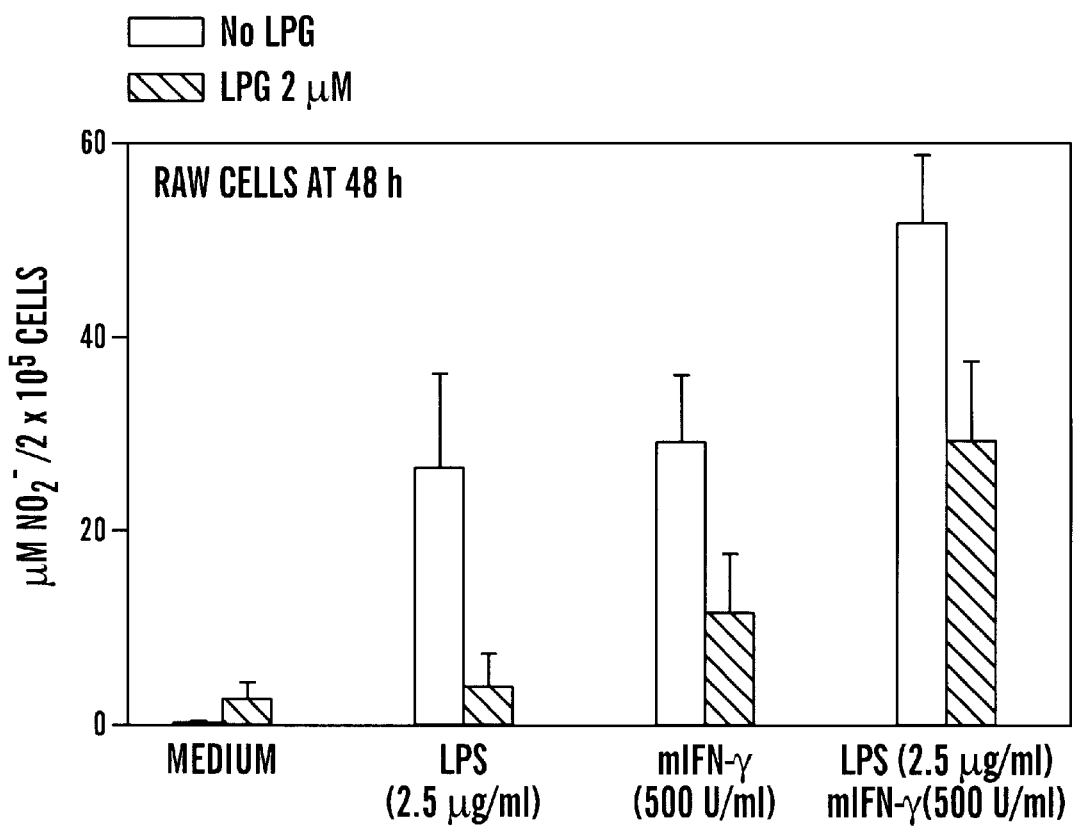

FIG. 24 shows the effect of LPG or Leishmania on induction of murine nitric oxide synthase activity. RAW 264.7 cells were treated with LPG 1 μM and simultaneously stimulated with endotoxin and mIFN-γ. Supernatants from each treatment condition were removed at 24, 48, and 72 hours, and nitrite production was measured by the Griess assay.

Figure 25:
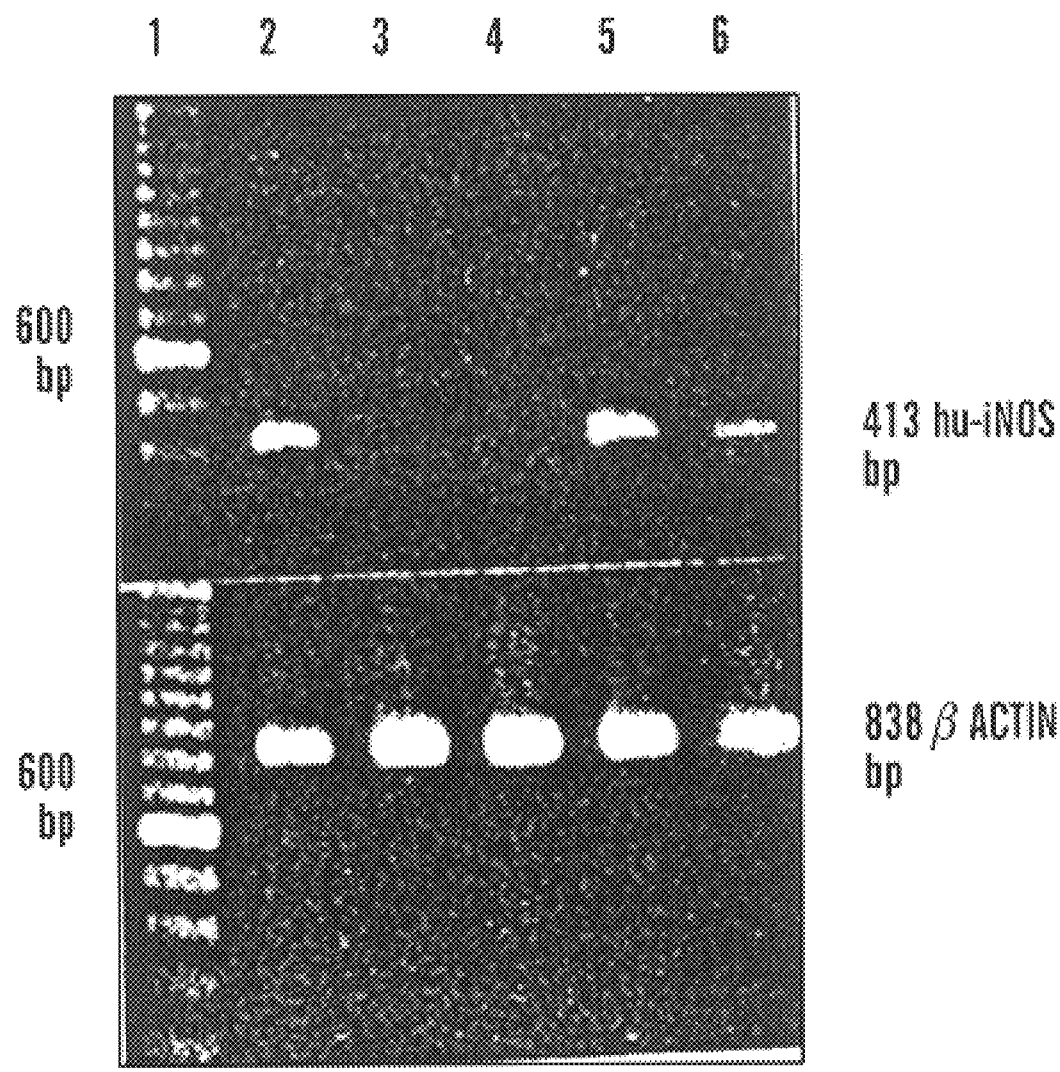

FIG. 25 shows the expression of NOS by human macrophages infected with *M. tuberculosis* and suppression by LPG. Human peripheral blood derived macrophages were primed with IFN-γ-primed autologous mononuclear cells and treated or not with LPG 2 μM. Of the total RNA isolated from each condition, 0.5 μg was used for reverse transcription and 10% of the cDNA was used to perform polymerase chain reaction using primers constructed from exon 1 and exon 5 (or exon 2 and 7) of the hepatic inducible NOS gene. Renal cells (297) stably transfected with pcHCl, a plasmid containing the human hepatic NOS gene (about 10% express NOS), served as positive control. Illustrated in this figure are: lanes: 1, molecular marker (600 bp most intense); 2, NOS-transfectants; 3, macrophages in medium; 4, macrophages in medium; 5, macrophages infected with *M. tuberculosis*; and 6, LPG 2 μM treated-macrophages infected with *M. tuberculosis*.

FIG. 26 shows the effect of LPG on release of tissue factor by endotoxin-stimulated endothelial cells. Endothelial cell monolayers were pretreated with LPG for 1 hour and stimulated with endotoxin. Cultured endothelial cells, when stimulated by endotoxin, expressed high amounts of tissue factor. LPG treatment suppressed endotoxin induction of tissue factor. The production of tissue factor (in culture supernatant) is determined by a one-stage clotting assay. Helin et. al., "Allogeneic Induction of the Human T-cell-instructed Monocyte Procoagulant Response is Rapid and is Elicited by HLA-DR," *J. Exp. Med*. 158: 962–75 (1983), which is hereby incorporated by reference.

FIGS. 27A–D show the effect of LPG on HIV p24 production in HIV-infected mononuclear cells.

Figure 28:
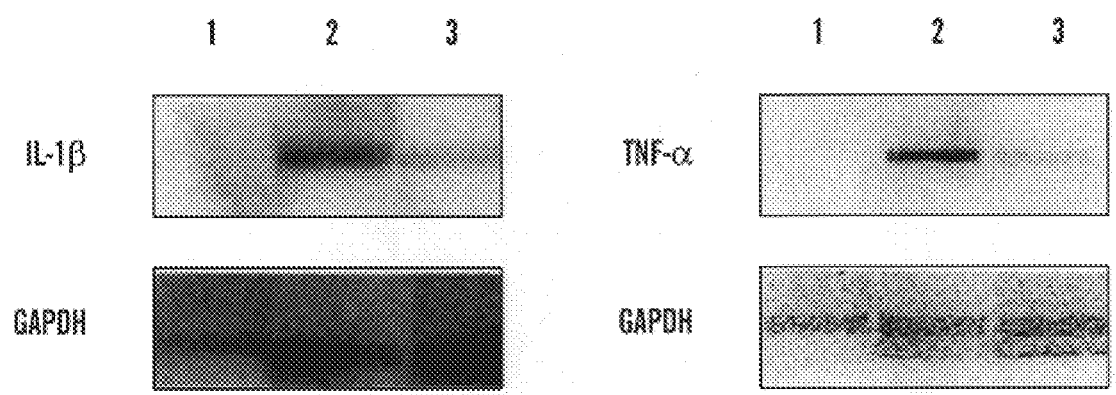

FIG. 28 shows the inhibition of cytokine IL-α and TNF-α gene transcription in a nuclear run-on assay. In vivo transcription of IL-1β, TNF-α, and GAPDH using nuclei isolated from THO-1 monocytes and transcribed $^{32}$P-labelled mRNA captured by either IL-1β, TNF-α, or GAPDH cDNA immobilized on nylon. Lanes: 1, medium; 2, endotoxin ILPS, 1 μg/ml); 3, LPG (1 μM) plus LPS.

Figure 29:
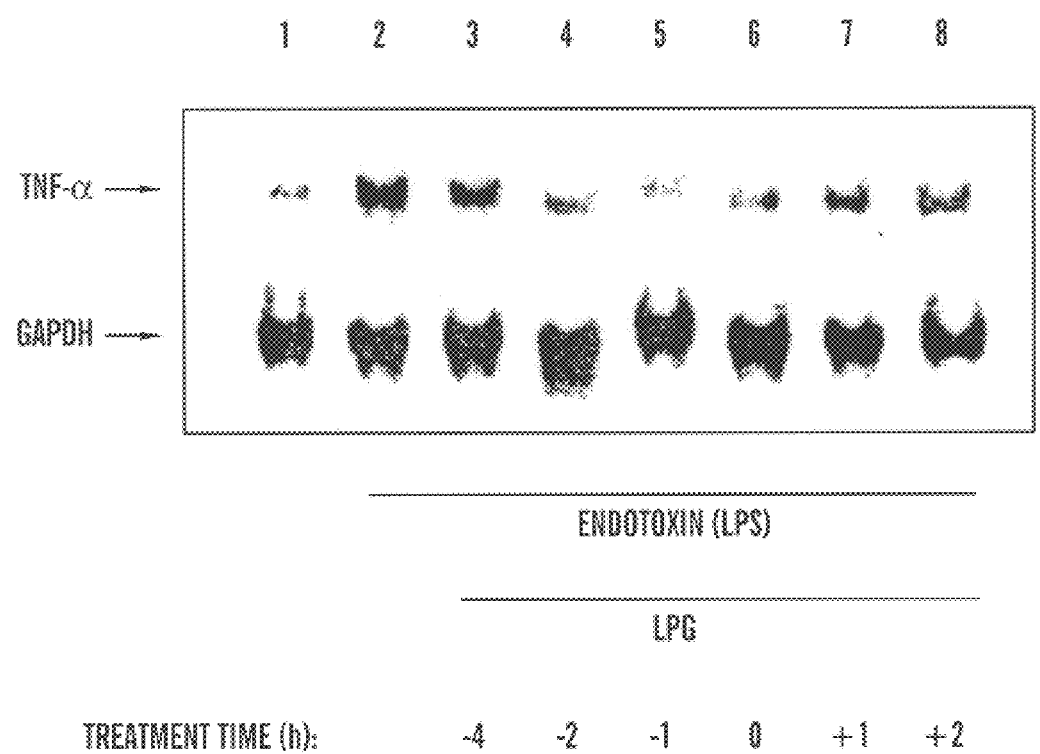

FIG. 29 shows the inhibition of endotoxin induction of TNF-α mRNA and GAPDH mRNA in an autoradiogram with ethidium bromide stain.

Figure 30:
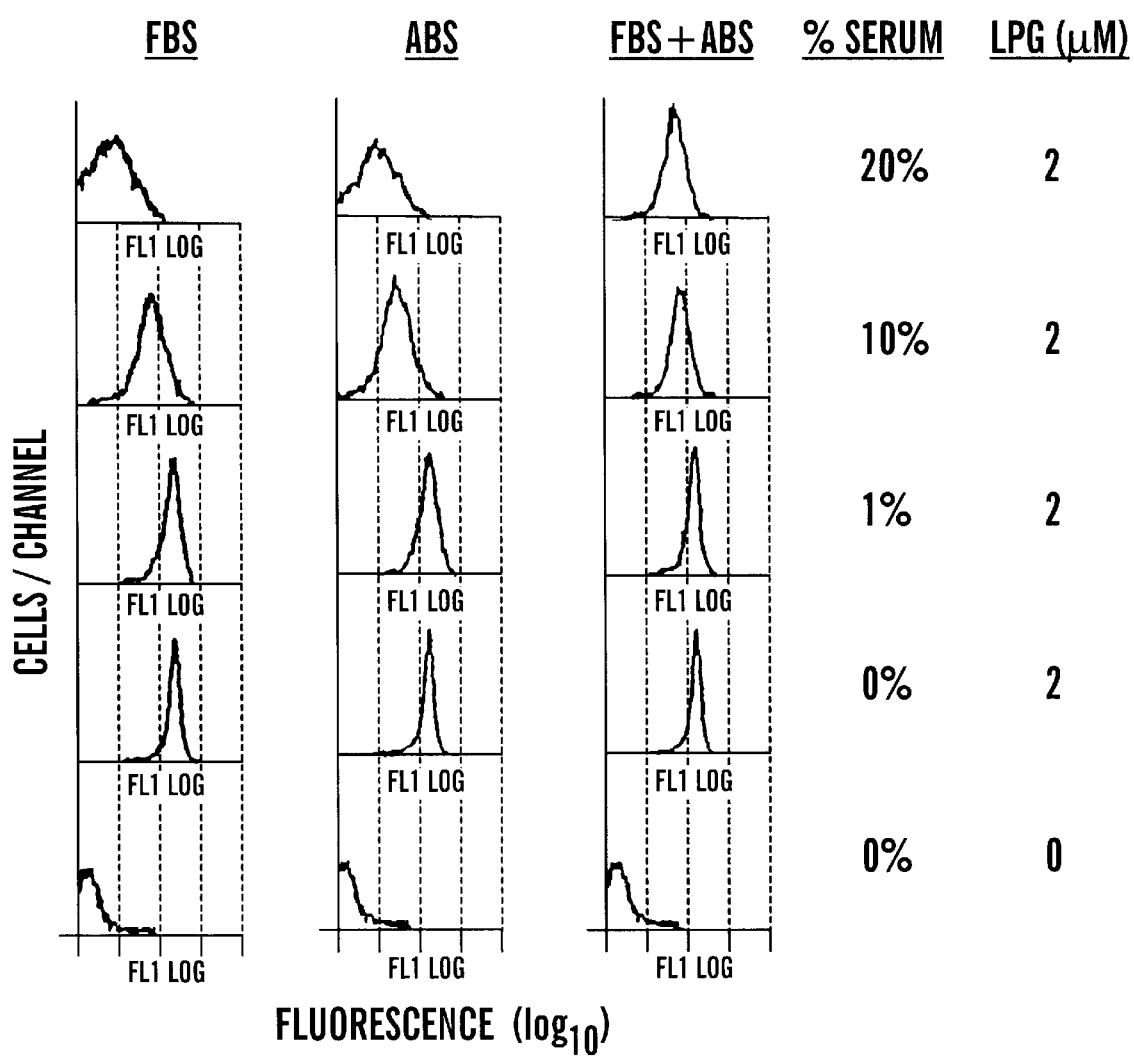

FIG. 30 shows plots of cells per channel versus fluorescence for varying levels of serum and/or LPG which suggests that serum binds to LPG.

Figure 31:
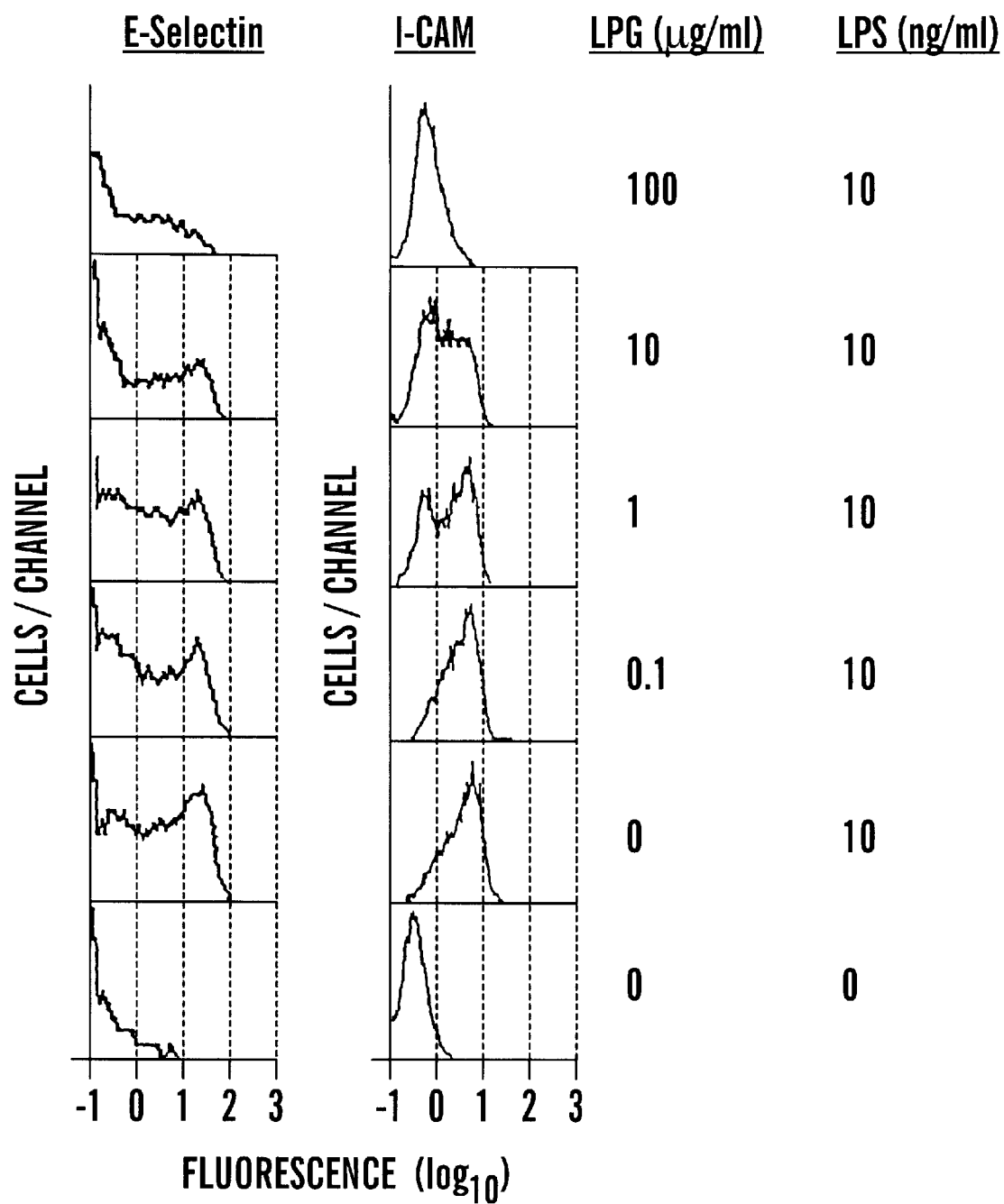

FIG. 31 shows plots of endothelial cells per channel versus fluorescence where the cells are treated with varying levels of LPG and challenged with LPS.

DETAILED DESCRIPTION OF THE INVENTION

The present invention relates to a method of treating inflammatory diseases in mammals. This process involves administering an effective amount of lipophosphoglycan or a lipophosphoglycan analogue to the mammal.

The importance of neutrophils and monocytes, often collectively referred to as phagocytes, in the pathophysiology of inflammation is explained in H. Brady, "Commentary—Leukocyte Adhesion Molecules: Potential Targets for Therapeutic Intervention in Kidney Diseases," 1993 *Current Science ISSN* 1062–4813 (1993), which is hereby incorporated by reference. Migration of phagocytes from blood to extravascular sites of inflammation involves migration of phagocytes from blood to extravascular sites of inflammation by several coordinated steps. Resident tissue macrophages ingest invading microorganisms in their native state or following opsonization with antibody and complement and release of chemoattractants and cytokines into surrounding tissue. Chemoattractants provoke migration of circulating phagocytes toward the site inflammation (i.e. chemotaxis) and phagocyte adhesion to endothelial cells of adjacent blood vessel walls (i.e. margination). Adherent phagocytes diapedese between endothelial cells and carve a path through basement membrane and extravascular tissue to the site of inflammation. They, in turn, phagocytose the antigen.

Adhesion of phagocytes to endothelial cells and other resident cells is mediated, in large part, by 3 families of cell surface molecules—i.e. selectins, integrins, and immunoglobulin-like molecules. Initial attachment of circulating phagocytes to endothelial cells appears to involve the interaction of phagocyte or endothelial selectins with carbohydrate-counter receptors. Selectin-mediated adhesion is relatively resistant to shear stress but insufficient to immobilize phagocytes on endothelium. Engagement of selectins with counter-receptors causes phagocytes to roll on endothelium and facilitates their immobilization by the interaction of phagocytes integrins with immunoglobulin-like molecules on endothelium and subsequent diapedesis.

There are 3 types of selectins—i.e. P-selectin (i.e. platelet selectin), E-selectin (i.e. endothelial cell selectin), and L-selectin (i.e. leukocyte selectin). Selectins have an NH$_2$-terminal lectin domain, an epidermal growth factor-like domain, several repeat sequences that share homology with complement regulatory proteins, a transmembrane domain, and a short COOH-terminal domain.

Integrins are heterodimeric molecules composed of α and β subunits, where the β subunit is common in each class of integrin and the α subunit is distinct. Examples of integrins include VLA-4, CD11a/CD18 β2, CD11b/CD18 β2, and CD11c/CD18 β2.

The immunoglobulin-like molecules are ICAM-1, ICAM-2, and VCAM-1.

The types of inflammatory disease treated according to this aspect of the present invention include transplantation rejection (e.g., renal allograft rejection, a cardiac allograft rejection, and transplantation-associated vasculopathy), nephritis (e.g., acute glomerulonephritis, lupus nephritis and tubulointerstitial nephritis), asthma (e.g., allergic asthma), respiratory distress syndrome, gastritis (e.g.,indomethacin-induced gastritis), rheumatoid diseases (e.g., arthritis or lupus), autoimmune diseases (e.g., vasculitis, diabetes, and HIV), sepsis, thrombosis, and coronary artery disease (e.g., restenosis after angioplasty or by-pass surgery and ischemia).

Lipophosphoglycans are fully discussed in S. J. Turco, et. al., "The Lipophosphoglycan of Leishmania Parasites," *Annu. Rev. Microbiol.* 46: 65–94 (1992) and the references cited therein, which are hereby incorporated by reference. These glycoconjugates are macromolecules found on the surface of protozoan parasites of the genus Leishmania. In the promastigote form of Leishmania, lipophosphoglycan has the structure shown in FIG. 1 which includes the following 4 domains: a phosphatidylinositol lipid anchor, a phosphosaccharide core, a repeating phosphorylated saccharide region, and a small oligosaccharide cap structure. Structural analyses of lipophosphoglycans from several Leishmania species indicates complete conservation of the lipid anchor, extensive conservation of the phosphosaccharide core, and variability of sugar composition and sequence in the repeating phosphorylated saccharide units and the cap structure.

The polysaccharide portion of the lipophosphoglycan is anchored by the unusual phospholipid derivative 1-O-alkyl-2-lyso-phosphatidyl(myo)inositol. Generally, all species of Leishmania have an aliphatic chain consisting of either a $C_{24}$ or $C_{26}$ saturated, unbranched hydrocarbon.

The phosphosaccharide core of lipophosphoglycans is attached to the inositol of the lipid anchor. In *Leishmania donovani*, *Leishmania major*, and *Leishmania mexicana*, the glycan core includes an unacetylated glucosamine, two mannoses, a galactose-6-phosphophate, a galactopyranose, and a galactofuranose.

As in all reported glycosylphosphatidylinositol-anchored proteins, lipophosphoglycan possess the Man(α1,4)GlcN (α1,6)myo-inositol-1-$PO_4$ motif. The lipophosphoglycan cores of *Leishmania donovani* and *Leishmania mexicana* possess a glucosyl-α1-phosphate attached in phosphodiester linkage to the C6 hydroxyl of the proximal mannose residue. A substantial percentage of the *Leishmania major* lipophosphoglycan also contains the identical glucosyl-α1-phosphate substitution, while the remainder does not.

The repeating unit of lipophosphoglycans is their repeating phosphorylated saccharide region which contains multiple units of backbone structure of $PO_4$–6Gal(β1,4)Man (α1,4). The 4-O-substituted mannose residue in the backbone is not found in any other eukaryotic glycoconjugate. The *Leishmania donovani* lipophosphoglycan contains no other substitutions of the backbone sequence, while lipophosphoglycan from *Leishmania mexicana* has about 25% of the galactose residues substituted at the C3 hydroxyl with βGlc residues. The repeating units of the Leishmania major lipophosphoglycan have approximately 87% of the galactose residues further substituted with small saccharide side chains containing one to four residues of galactose, glucose, or pentose arabinose.

Lipophosphoglycans are terminated at the nonreducing end with one of several small neutral oligosaccharides containing galactose or mannose. For *Leishmania major*, capping is carried out with Man(α1,2)(Manα1). The terminal oligosaccharide of the *Leishmania donovani* and Leishmania lipophosphoglycan is the branched trisaccharide Gal (β1,4)[Man(α1,2)]Man(α1).

During promastigote metacyclogenesis, lipophosphoglycans undergo a number structural modifications. In *Leishmania major*, lipophosphoglycan at various growth stages revealed conservation of lyso-1-O-alkylphosphatidylinositol lipid anchor and the phosphosaccharide core. In addition, in this species, as well as *Leishmania donovani*, there is a 2 fold increase in the length of the metacyclic form of lipophosphoglycan due to an approximate doubling in the number of repeating phosphorylated saccharide units. These repeat units contain β-galactose residues that branch off the disaccharide backbone as side chains. Upon differentiation to metacyclic promastigotes, the repeat units terminate predominately with α-arabinose and β-glucose residues. In *Leishmania donovani*, elongation occurs; however, alterations of the cap oligosaccharides emerge in the metacyclic form. The sole terminal galactose residue present in the cap oligosaccharide of lipophosphoglycan from noninfectious parasites is absent in the metacyclic form.

Although lipophosphoglycan is not present in amastigotes of *Leishmania donovani*, *Leishmania major* amastigotes do synthesize this compound in a form which is biochemically and antigenically distinct from that produced by promastigotes. This is due to minor distinctions in their carbohydrates.

All of these forms of lipophosphoglycans can be used in accordance with the present invention. Also useful are lipophosphoglycan analogs in the form of the above-discussed component parts of lipophosphoglycans and extracellular lipophosphoglycan-like glycoconjugates.

The above-discussed component parts of lipophosphoglycans can exist as distinct entities. For example glycosylphosphatidylinositol antigens and glycosylinositolphospholipids, which are present in *Leishmania donovani* and *Leishmania major*, closely resemble the phosphosaccharide core-phosphatidylinositol region of lipophosphoglycan. Fragments of lipophosphoglycan can be prepared and purified from whole lipophosphoglycan by, for example, the procedures described in M. J. McConville, et al., "A Family of Glycoinositolphospholipids from *Leishmania major* Isolation, Characterization and Antigenicity," *J. Biol. Chem.* 264:757–66 (1987); McConville, et al., "Lipophosphoglycan of *Leishmania major* that Vaccinates Against Cutaneous Leishmaniasis Contains an Alkylglycerophosphoinositol Lipid Anchor," *Proc. Natl. Acad. Sci. USA* 84:8941–43 (1987), and M. J. McConville, et al., "Structure of the Lipophosphoglycan from *Leishmania major*," *J. Biol. Chem.* 32:19611–23 (1990), which are hereby incorporated by reference.

Lipophosphoglycan-like glycoconjugate compounds, collectively referred to as excreted factor, are found in conditioned medium from Leishmania parasites in 3 forms. One form is a very tight complex of lipophosphoglycan with albumin and is essentially identical to cell-associated lipophosphoglycan. The second category of compounds are the repeating phosphorylated saccharide units of lipophosphoglycan in the form of a carbohydrate chain of an acid phosphatase secreted by *Leishmania donovani, Leishmania tropical,* and *Leishmania mexicana.* The third category of lipophosphoglycan-like compounds is an extracellular phosphoglycan. This material has been analyzed and found to have the following structure: (CAP)→[PO$_4$-6Gal(β1,4)Man (α1)]. The cap was found to be one of several small neutral oligosaccharides, mainly with the branched trisaccharide Gal(β1,4)[Man(α1,2)]Man(α1). This compound is thus identical to cell-derived lipophosphoglycan except that it lacks a lipid anchor, the phosphosaccharide core, and several repeating units.

Figure 2:
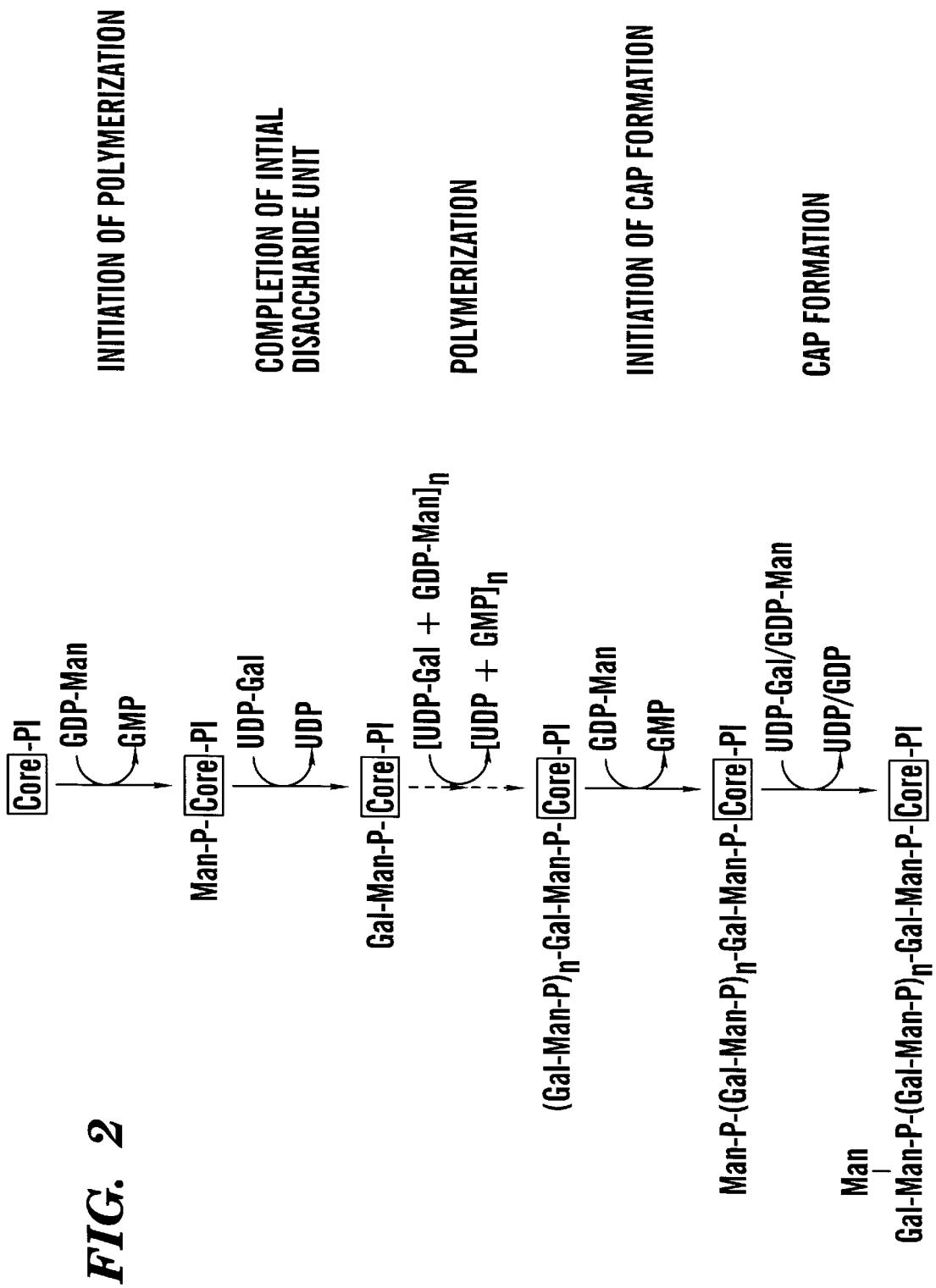
FIG. 2 shows a schematic pathway for assembly of the three repeating units and capping oligosaccharides of *Leishmania donovani* lipophosphoglycan. The core structure is Gal(α1,6)Gal(α1,3)Gal(β1,3)Man(α1,3)Man(α1,4)GlcN (α1,6), and PI is lyso-1-O-alkylphosphatidylinositol.

Lipophosphoglycans can be isolated from Leishmania bacteria by known procedures. See e.g., M. J. McConville, et al., "The Structure Biosynthesis and Function of Glycosylated-Phosphatidylinositols in the Parasitic Protozoa and Higher Eukaryotes," *Biochem. J.* 294:305–24 (1993) and S. F. Moody, et al., "The Structure of *Leishmania major* Amastigote Lipophosphoglycan," *J. Biol. Chem.* 268:18457–66 (1993), which are hereby incorporated by reference. Lipophosphoglycans are biosynthesized region by region in Leishmania protozoa. This process is shown schematically in FIG. 2 and is described in the following paragraphs.

The phosphatidylinositol anchor of lipophosphoglycan can biosynthetically assembled by acylation of the C1 glycolytic intermediate dihydroxyacetone phosphate. The acyl group can then be replaced with a fatty alcohol, and the resulting alkyl dihydroxyacetonephosphate is reduced with NADPH and acylated at the sn-2 position, forming 1-O-alkyl-2-acyl phosphatidic acid. This acid is activated to the CDP-derivative by CTP and condensed with myo-inositol to form 1-O-alkyl-2-acyl-PI.

The core-PI region is biosynthetically produced by transferring N-acetylglucosamine from UDP-GlcNAc to PI forming GlcNAc-PI which, in turn, is deacetylated to produce GlcN-PI. Mannose residues are then added by using mannosylphosphoryldolichol as the mannose donor. Addition of one mannose would form Man(α1,4)GlcN-PI, while addition of a second mannose would yield Man(α1,3)Man(α1,4)GlcN-PI. Three galactose residues are then added.

The repeat units are formed by polymerization which involves sequential addition of galactose and mannose residues to lipophosphoglycan from their respective nucleotide-sugar donors. Guanosine diphosphate-Man donates mannose-1-phosphate, so the alternating addition of mannose-1-phosphate and galactose residues can be used.

Various leishmanial lipophosphoglycans contain a Man(α1,2)Man(α1) at the reducing end. It is believed that a Man(α1,2)mannosyltransferase causes cessation of lipophosphoglycan elongation with formation of a chain-terminating Man(α1,2)Man(α1) containing cap oligosaccharide.

The lipophosphoglycan or lipophosphoglycan analog of this invention can be administered orally, parenterally, for example, subcutaneously, intravenously, intramuscularly, intraperitoneally, by intranasal instillation, or by application to mucous membranes, such as, that of the nose, throat, bronchial tubes, and vagina (which is particularly useful in blocking heterosexual HIV transmission), or by instillation into hollow organ walls or newly vascularized blood vessels. They may be administered alone or with suitable pharmaceutical carriers, and can be in solid or liquid form such as, tablets, capsules, powders, solutions, suspensions, or emulsions.

The solid unit dosage forms can be of the conventional type. The solid form can be a capsule, such as an ordinary gelatin type containing the lipophosphoglycan or lipophosphoglycan analog of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

The lipophosphoglycan or lipophosphoglycan analog of this invention may also be administered in injectable dosages by solution or suspension of these materials in a physiologically acceptable diluent with a pharmaceutical carrier. Such carriers include sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

For use as aerosols, the lipophosphoglycan or lipophosphoglycan analog of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Another aspect of the present invention relates to a method of inhibiting production of adhesion molecules on endothelial cells. This process involves administering an effective amount of lipophosphoglycan to the endothelial cells.

In this aspect of the present invention, the lipophosphoglycan can be administered to endothelial cells in culture or to mammals. Administration to mammals is in the dose forms and modes described above.

The present invention also relates to inhibiting production of tissue factor by endothelial cells. This process involves administering an effective amount of lipophosphoglycan or lipophosphoglycan analogue to the endothelial cells.

Here, the lipophosphoglycan or lipophosphoglycan analogue can be administered to endothelial cells in culture or to mammals. *µ*gain, administration to mammals is in the dose forms and modes described above.

A method of inhibiting induction of nitric oxide synthase by macrophages is also disclosed. This involves administering an effective amount of lipophosphoglycan or lipophosphoglycan analogue to macrophages.

This aspect of the present invention involves administration to macrophages in culture or to mammals. Administration to mammals involves the dose forms and modes disclosed previously.

A method of reversing the inhibitory effects of lipophosphoglycan on endothelial cells or macrophages is also disclosed. Here, an effective amount of lipophosphoglycan analogues are administered to endothelial cells or macrophages which are being contacted with lipophosphoglycan. Administration of the analogues cannot be after administration of lipophosphoglycan.

In this aspect of the present invention, administration can be to endothelial cells or macrophages in culture or to mammals. Administration to mammals is described above.

The present invention also relates to a method of targeting material to endothelial cells, fibroblasts, or monocytes. This involves associating lipophosphoglycan or lipophosphoglycan analogues with the material to be targeted to form a complex. The complex is then administered to endothelial cells, fibroblasts, or monocytes. A product for such targeting is also disclosed.

Suitable lipophosphoglycan analogues include phosphatidylinositol lipid anchor of lipophosphoglycan, polyphosphosaccharide core of lipophosphoglycan, or extracellular lipophosphoglycan-like glycoconjugates.

In this aspect of the present invention, the endothelial cells, fibroblasts, or monocytes can be in culture. Alternatively, administration can be to a mammal in the dose forms and modes described above.

Another aspect of the present invention relates to an isolated DNA molecule suitable for connection to a gene capable of transcription. Lipophosphoglycan or lipophosphoglycan analogues bind to the DNA molecule or trigger nuclear protein(s) binding to the DNA molecule. Such binding antagonizes transcription of the gene. The NA molecule, when positioned to regulate transcription of the gene, can be used to carry out a method of testing drugs for inhibiting production of tissue factor, nitric oxide synthase, proinflammatory cytokines, or adhesion molecules.

The DNA molecule is found within the IL-1 promoter region. The IL-1 promoter region and its nucleotide sequence is described in DNASIS, File Name IL1PROM.DNA, which is hereby incorporated by reference. The IL-β promoter containing LPG response sequence and proximal endotoxin response elements have the following nucleotide sequence (SEQ. ID. No. 1):

The present invention is illustrated by the following Examples.

EXAMPLES

Examples 1 to 15 relate to studies using lipophosphoglycan from Leishmania to suppress agonist induced IL-1β gene expression in human monocytes by a unique promoter sequence.

Example 1

Human Monocytes and Their Isolation, Cell Line and Reagents

Human peripheral blood cells from the New York Blood Center (New York, N.Y.) obtained by Hypaque-Ficoll density centrifugation and adherence to plastic are 99% monocytes. J. L. Ho, B. X. Zhu, S. H. He, B. H. Du, and R. Rothman, "Interleukin-4 Receptor Signaling Involves Activation of Phosphatidylcholine Specific Phospholipase C. Comparison with Chemotactic Peptide, FMLP and Sphingomyelinase," *J. Exp. Med.*, 180:1457–69 (1994), which is hereby incorporated by reference. Human monocytic cells THP-1 (TIB-202) and plasmid containing glyceraldehyde-3-phosphate dehydrogenase [GAPDH] cDNA (cat. #57090) were obtained from American Type

```
CATTCTTCTA ACGTGGGAAA ATCCAGTATT TTAATGTGGA CATCAACTGC ACAACGATTG    60

TCAGGAAAAC AATGCATATT TGCATGGTGA TACATTTGCA AAATGTGTCA TAGTTTGCTA   120

CTCCTTGCCC TTCCATGAAC CAGAGAATTA TCTCAGTTTA TTAGTCCCCT CCCCTAAAAG   180

CTTCCACCAA TACTCTTTTT CCCCTTTCCT TTAACTTGAT TGTGAAATCA GGTATTCAAC   240

AGAGAAATTT CTCAGCCTCC TACTTCTGCT TTTGAAAGCT ATAAAAACAG CGAGGGAGAA   300

ACTGGCAGAT ACCAAACCTC TCCGAGG                                       327
```

More particularly, the DNA molecule of the present invention corresponds to nucleotides –310 to –57 of the IL-1 promoter region and has the following nucleotide sequence (SEQ. ID. No. 2):

Culture Collection (ATCC), Rockville, MdD. Plasmids containing IL-1β cDNA were obtained from Dr. Steve Gillis, Immunex Corp., Seattle, Wash. or from ATCC (cat. #39925). C. J. March, B. Mosley, A. Larsen, D. P. Cerretti, G. Braedt,

```
CATTCTTCTA ACGTGGGAAA ATCCAGTATT TTAATGTGGA CATCAACTGC ACAACGATTG    60

TCAGGAAAAC AATGCATATT TGCATGGTGA TACATTTGCA AAATGTGTCA TAGTTTGCTA   120

CTCCTTGCCC TTCCATGAAC CAGAGAATTA TCTCAGTTTA TTAGTCCCCT CCCCTAAAAG   180

CTTCCACCAA TACTCTTTTT CCCCTTTCCT TTAACTTGAT TGTGAAATCA GGTATTCAAC   240

AGAGAAATTT CTCA                                                     254
```

More preferably, the DNA molecule of the present invention corresponds to nucleotides –310 to –137 of the IL-1 promoter region and has the following nucleotide sequence (SEQ. ID. No. 3):

V. Price, S. Gillis, C. S. Henney, S. R. Kronheim, K. Grabstein, P. Conlon, T. P. Hopp, and D. Cosman, "Cloning, Sequencing and Expression of Two Distinct Human Interleukin-1 Complementary DNAs," *Nature*, 315:641–47.

```
CATTCTTCTA ACGTGGGAAA ATCCAGTATT TTAATGTGGA CATCAACTGC ACAACGATTG    60

TCAGGAAAAC AATGCATATT TGCATGGTGA TACATTTGCA AAATGTGTCA TAGTTTGCTA   120

CTCCTTGCCC TTCCATGAAC CAGAGAATTA TCTCAGTTTA TTAGTCCCCT CCCC         174
```

(1985), which is hereby incorporated by reference. RPMI-1640, fetal bovine serum, L-glutamine, and penicillin-streptomycin (Gibco, Grand Island, N.Y.); β-mercaptoethanol, phorbol 12-myristate 13-acetate (PMA) and LPS from *Escherichia coli* serotype 055: B5 were purchased from the Sigma Chemical Co., St. Louis, Miss. 24-well plates were purchased from Corning, Corning, N.Y., and tumor necrosis factor (TNF)-α was a gift from Genentech, South San Francisco, Calif.

Example 2

Isolation and Purification of LPG

LPG was isolated and purified from *Leishmania donovani* promastigotes as previously described. P. A. Orlandi and S. J. Turco, "Structure of the Lipid Moiety of the *Leishmania donovani* Lipophosphoglycan," *J. Biol. Chem.*, 262:10384–91 (1987), which is hereby incorporated by reference. The LPG from *L. donovani* used in these experiments was free of protein and with a LPS content of <10 pg per 100 μg as determined by the Limmulus amebocyte assay. P. A. Orlandi and S. J. Turco, "Structure of the Lipid Moiety of the *Leishmania donovani* Lipophosphoglycan," *J. Biol. Chem.*, 262:10384–91 (1987), which is hereby incorporated by reference. The $M_r$ of LPG was taken as taken as $9.5 \times 10^{16}$ and 10 μg/ml is equal to 1 μM.

Example 3

Cell Culture and Treatment with LPG and Stimuli

Human monocytes were cultured in endotoxin free complete medium as previously described. J. L. Ho, R. Badaro, D. Hatzigeorgiou, S. G. Reed, and W. D. Johnson Jr., "Cytokines in the Treatment of Leishmaniasis: From Studies of Immunopathology to Patient Therapy," *Biother.*, 7:223–35 (1994), which is hereby incorporated by reference. THP-1 cells were maintained in RPMI-1640 supplemented with 2 mM L-glutamine, 100 U/ml penicillin-streptomycin, $5 \times 10^{-5}$ M β-mercaptoethanol, and 10% heat-inactivated fetal bovine serum (FBS). For experiments to determine the effect of LPG, THP-1 cells ($10 \times 10^6$ per condition) were washed with RPMI 1640 and resuspended in complete medium composed of RPMI-1640 supplemented with 2 mM L-glutamine, 100 U/ml penicillin and 100 μg/ml streptomycin. These cells were cultured in 24-well plates with or without 0.01 to 2 μM LPG (0.1 to 20 μg/ml) for different times either before (-h), simultaneously with (0 h) or after (+h) the addition of inducers of IL-1β (eg., LPS, TNF-α, or *S. epidermidis*). Peripheral blood monocytes enumerated after detachment using a rubber policeman were similarly treated or not with LPG and cultured with stimuli. Cell were stimulated with 0.1 to 3 μg/ml LPS, TNF-α (50 ng/ml), 25 to 50 ng/ml PMA for 4 to 24 h, or opsonized heat-killed *S. epiderimidis* at ratio of 10 particles per cell. Single colony of *S. epidermidis* grown overnight in tryptocase soy broth was picked, washed, diluted to $3 \times 10^8$ organisms/ml in normal saline was heated at 65° C. for 1 h. irradiated with 3,000 Rads, and stored at -70° C. Bacteria were opsonized by addition of 0.9 ml of a 10-fold dilution of the stock to 0.1 ml of serus, for 2 h by tumbling rotation. This material was diluted in medium and added to THP-1 cells at a ratio of 10 particles to THP-1 cell.

Example 4

Northern Analysis with CDNA Probes of IL-1β and GAPDH

Cells treated with or without LPG and/or inducers of IL-1β were harvested by gentle scrapping using a rubber policeman and sedimented by centrifugation at 500 g for 5 minutes in a microfuge. Total RNA was extracted using RNA STAT-60 solution (TEL-TEST "B" Inc., Friendswood, Tex.), based on a single step method for RNA isolation (P. Chomczynski and N. Sacchi, "Single-step Method of RNA Isolation by Acid Guanidinium Thiocyanate-phenol-chloroform Extraction," *Anal. Biochem.*, 162:156–59 (1987), hereby incorporated by reference), and quantitated by spectrophotometry. Equal amount of total RNA (15–20 μg per sample) was denatured, loaded onto 1.2% agarose-formaldehyde gel, run for 4 h at 30 volts and subsequently transferred by capillary action onto nylon membrane (0.45 μm pore size, NYTRAN, S&S, Keene, N.H.). Membranes were prehybridized at 42° C. for 4 h in prehybridization buffer (50% formamide, 6×SSPE, and 0.5% SDS), and hybridized in hybridization buffer (50% formamide, 6×SSPE, and 5 SDS) containing $10-15 \times 10^6$ cpm of random-priming $^{32}$p-labeled IL-1β cDNA (Boehringer Mannheim GmbH, Mannheim, Germany). IL-1β cDNA fragment was excised by digestion with restriction enzymes and purified using standard techniques. Sambrook, J., et al., *Molecular Cloning: A Laboratory Manual* (Cold Spring Harbor Laboratory Press 1989), hereby incorporated by reference. Purified IL-1 or GAPDH cDNAs (0.1 μg) was labeled with $[\beta^{32}P]$ dCTP using random-priming method. Washed membranes were exposed to KODAK X-OMAT AR films for 24 to 72 h and to phosphor screens (Molecular Dynamics Ltd., Kent, Tenn.) for 24–28 h. Quantitative analysis of the specific bands was performed using Phosphor Imager Analyzer. In experiments using *S. epidermidis* to induce IL-1β, cells were washed twice with ice cold medium and centrifugation at 160×g and 250×g, each for 5 min to remove excess *S. epidermidis* that would interfere with RNA extraction. All percent suppression of IL-1β mRNA values were normalized by the amount of GAPDH present in each condition which varied less than 10% between conditions because equivalent amounts of total RNA were loaded for electrophoresis.

Example 5

IL-1β mRNA Stability

THP-1 cells ($10^7$ cells/condition) were stimulated with 2 μg/ml LPS or 2 μg/ml LPS with 2 μM LPG at time 0 h. Actinomycin D (6 μg/ml) was added to all conditions 2 h later and cells were harvested by gentle scraping for extraction of total RNA at the designated time. The 2 h time point after LPS or LPS plus LPG treatment was used as the respective reference for comparison with residual IL-1β mRNA at the later time points. For each condition and time, the total RNA separated on agarose gel, transferred and immobilized on nylon membrane were probed with $^{32}$P-labeled IL-1β cDNA or GAPDH cDNA.

Example 6

In vitro Transcription by the Nuclear Run-off Assay

Nuclei isolation. Procedures for isolating nuclei have been described in Ausubel, F. M. et al., *Current Protocols in Molecular Biology* 1(4.9):4.9.1–4.9.14 and 1(4.10):4.10.1–4.10.11 (1993), hereby incorporated by reference. THP-1 cells ($5 \times 10^7$ cells) treated with medium or medium containing 2 μM LPG for 2 h were stimulated or not stimulated with 2 μg/ml LPS for 4 h, at 37° C. in 5% $CO_2$. Cells were harvested by gentle scraping, washed twice with 5 ml ice cold PBS and centrifugation at 350×g for 5 min. After removal of supernatant, cells were gently loosen by 5 sec vortex and 4 ml NP-40 buffer was added by continuous vortex. The NP-40 buffer is composed of 10 mM Tris HCl (pH 7.4), 10 mM NaCl, 3 mM $MgCl_2$, and 0.5% noridet P-40 (NP-40). The cell suspension was further vortexed at half maximal speed for 10 sec and placed on ice for 5 min. Cells were visually inspected to ascertain the separation of nuclei from cytophasmic material. Nuclei were wash once more with 4 ml NP-40 buffer by centrifugation at 350×g, 5 min. The pelleted nuclei were resuspended with 200 µl glycerol buffer and stored in liquid nitrogen until nuclear run-off assay. Glycerol buffer is composed of 50 mM Tris Hcl (pH 8.3), 40% (v/v) glycerol, 5 mM $MgCl_2$, 0.1 mM ethylenediaminetetraacetic acid (EDTA).

In vitro transcription. The nuclear run-off assay for in vitro transcription was performed as described in Ausubel, F. M. et al., *Current Protocols in Molecular Biology* 1(4.9):4.9.1–4.9.14 and 1(4.10):4.10.1–4.10.11 (1993). Nuclei previously treated were thawed at room temperature after removal from storage in liquid nitrogen. In vitro transcription is initiated by the addition of 200 µl 2×reaction buffer with nucleotides and 100 µCi [$\alpha^{32}$P]UTP (10 µl 10 mCi/ml) to the nuclei, and incubation for 30 min at 30° C. in a shaking waterbath. To the nuclear run-off reaction, 600 µl HSB buffer containing 40 µg/ml of DNase I was added and the mixture incubated for 5 min at 30° C. The reaction was stopped with the addition of 200 µl SDS/Tris buffer and 200 µg of proteinase K. Proteins in the nuclear run-off reaction mixture were digested with an incubation of 42° C. for 30 min.

Extraction and precipitation of $^{32}$P-labeled RNA. To the nuclear run-off mixture was added 1 ml of phenol/chloroform/isoamyl alcohol (v:v:v, 25:24:1); this was centrifuged at 550×g for phase separation. The aqueous phase was transferred to a 15 ml tube to which the following were added 2 ml doubld distilled water, 3 ml 10% trichloroacetic acid (TCA)/60 mM sodium pyrophosphate, 100 µg tRNA (from *E. coli*), and incubated for 30 min on ice. The material precipitated by TCA was captured onto 0.45 µm HA filter by vacuum (Millipore Corp., Bedford Mass.). The filters were washed 3 times with 10 ml 5% TCA/30 mM sodium pyrophosphate solution. The filters transferred to glass scintillation vials were incubated with 1.5 ml DNase I buffer with 37.5 µg/ml DNase I (free of RNase) for 30 min at 37° C. The reaction was quenched by the addition of 45 µl 0.5 M EDTA, 68 µl 20% SDS and heating for 10 min. at 65° C. to elute RNA. The supernatant (approximately 1.5 ml) from the filter after DNaseI digestion was transferred to a 15 ml polypropylene tube, and the filters containing newly transcribed total RNA were incubated for 10 min at 65° C. with 1.5 ml elution buffer. The supernatant from the filter after DNase digestion and elution were pooled and treated with 90 µg proteinase K for 30 min at 37° C. From this mixture, total RNA was extracted by the addition of 3 ml phenol/chloroform/isoamyl alcohol (v:v:v, 25:24:1) and centrifuged at 550×g for 5 min. To the supernatant, after transfer to siliconized 30 ml Corex glass tubes, 0.75 ml of 1 M NaOH was added and incubated on ice for 10 min followed by the addition of 1.5 ml 1 M HEPES, 0.53 ml 3 M sodium acetate, and 14.5 ml of 100% ethanol. The mixture was kept at −20° C. overnight. Total RNA was precipitated by centrifugation 10,000×g (9,400 rpm, Sorval hi-speed centrifugre). After discarding the supernantant, the precipitated RNA is resuspended in 1 ml TES solution by gentle shaking at room temperature for 30 min.

Hybridization of in vitro transcribed RNA to plasmid containing the cDNA. 10 µg of each plasmic containing IL-1β or GAPDH cDNA previously denatured by 1 M NaOH were added and immobilized onto nylon membrane strips using a slot blot apparatus and UV cross-linked (Stratalinker-1800, Stratagene, La Jolla, Calif.). The strips containing immobilized plasmid DNA were placed into 4 ml plastic scintillation vials to which the recovered $^{32}$P-UTP labeled RNA (>5×10$^6$ cpm/ml) in 1 ml TES solution mixed with 1 ml TES/NaCl solution was added. Hybridization was performed in a shaking water bath at 65° C. for 48 h. After hybridization, the filters were transferred int 50 ml tubes and washed twice each time with 25 ml of 2×SSC at 65° C. for 1 h. The filters were transferred into glass scintillation vials containing 2×SSC and 10 µg/ml RNase and incubated to remove non hybridized RNA for 30 min at 37° C. The filter were washed once more with 25 ml 2×SSC for 1 h at 37° C. The filter strips were blot dried on Whatman 3 MM filter paper. The amount of hybridized newly synthesized $^{32}$P-labeled RNA was visualized by autoradiography and the amount of radioactivity quantitated using a Phospho Imager.

The constituents of the respective buffers were, for the 2×reaction buffer with nucleotides: 10 mM Tris CHl (pH 8.0), 5 mM $MgCl_2$, 0.3 M KCl, 1 mM ATP, 1 mM CTP, 1 mM GTP and 5 mM dithiotreitol; for HSB buffer: 0.5 M NaCl, 50 mM $MgCl_2$, 2 mM $CaCl_2$, 10 mM Tris HCl (pH 7.4); for SDS/Tris buffer: 5% sodium dodecyl sulfate (SDS), 0.5 M Tris HCl (pH 7.4), 0.125 mM EDTA; DNase 1 buffer: 20 mM HEPES (pH 7.5), 5 mM $MgCl_2$, 1 mM $CaCl_2$; for elution buffer: 1% (w/v) SDS, 10 mM Tris HCl (pH 7.5), 5 mM EDTA; and DNase I (RNase free, Boehringer Mannheim, Indiana, Ind.) suspended at 1 mg/ml in 0.1 M iodoacetic acid and 0.15 M sodium acetate (pH 5.3) was heated to 55° C. for 40 min. and allowed to cool to room temperature; 5 mM $CaCl_2$ was then added.

Example 7

Plasmid Constructs

The original plasmid vector was pTK.CAT (4.5 kb), containing the thymidine kinase ("TK") promoter, a promoterless chloramphenicol acetyltransferase ("CAT") gene, the SV40 polyadenylated site and parts of the pUC plasmid including Amp$^R$ gene. TK promoter was removed and the isolated IL-1β genomic sequence (−1110/+15) was linked upstream to CAT gene (Xhol/Hindlll). Y. Zhang, M. Doerflier, T. C. Lee, B. Guillemin, and W. N. Rom, "Mechanisms of Stimulation of Interleukin-1β and Tumor Necrosis Factor-α by *Mycobacterium tuberculosis* Components," *J. Clin. Investig.* 91:2076–83 (1993), which is hereby incorporated by reference. Mechanisms of stimulation of interleukin-1β and tumor necrosis factor-α by *Mycobacterium tuberculosis* components. Y. Zhang, and W. N. Rom, "Regulation of the Interleukin-1β Gene by Mycobacterial Components and Lipopolysaccharide is Mediated by Two Nuclear Factor-IL-6 Motifs," *Molec. & Cell. Biol.*, 13:3831–7 (1993), which is hereby incorporated by reference. 5' truncations (deletion mutants) were created by restriction enzyme digestion of the isolated IL-1β sequence. The deletion mutants are: −1110 (Xbal), −680 (Sau3Al), −310(Dral), −131(Hindlll) and −57 (Ddel), with numbers indicating base-pairs upstream relative to the transcription start site. In addition, human IL-1β genomic DNA fragments derived from lamdaBDC-454 were inserted into CAT gene plasmid vector pA10CAT (3M). Shirakawa, F., et al., "The Human proIL-1β Gene Requires Sequences Both Proximal and Distal to the Transcription Start Site For Tissue-Specific Induction," *Molec. Cell. Biol.* 13:1332–44 (1993) and Buras, J. A., et al., "The NF-βA (PU.1)-binding Element, Not An Overlapping NF-IL-6-binding Element, Is Required For Maximal IL-1β Gene Expression," *J. Immunol.* 152:4444–54 (1994). Specifically, the constructs containing −3757 to +11 full-length (XT-CAT) and a deletion mutant, −3757 to −2729 linked to −131 to +11 were used. Buras, J. A., et al., "The NF-βA (PU.1)-binding Element, Not An Overlapping NF-IL-6-binding Element, Is Required For Maximal IL-1β Gene Expression," *J. Immunol.* 152:4444–54 (1994).

Example 8

Transfection and Chloramphenicol Acetyltransferase Assay

THP-1 cells, washed twice with plain medium, were transiently transfected by a modified DEAE-Dextran method, as previously described in Y. Zhang and W. N. Rom, "Regulation of the Interleukin-1β Gene by Mycobacterial Components and Lipopolysaccharide is Mediated by Two Nuclear Factor-IL-6 Motifs," *Molec. & Cell. Biol.*, 13:3831–7 (1993), which is hereby incorporated by reference. 10 to 20×10$^6$ cells per condition were pooled, pelleted, mixed with plasmid DNA (3–5 μg per 10×10$^6$ cells) and 400 μg/ml DEAD-Dextran (Pharmacia LKB, Uppsala, Sweden) in 1 ml total volume S-TBS buffer containing 6×10$^7$ cells and, incubated at 37° C., 5% $CO_2$, for 75 min. S-TBS solution is composed of 137 mM NaCl, 5 mM KCl, 1 mM $Na_2HPO_4$, 25 mM Tris (pH 7.5), 1.4 mM $CaCl_2$. Cells exposed to DMSO (7%) for 5 min were washed, resuspended in RPMI-1640 supplemented with L-glutamine and 2.5% heat-inactivated FBS, and plated as 10$^7$ cells per well in 6-well plates. These transfected cells were incubated for 48 h at 37° C., 5% $CO_2$. Cells were then treated with medium or medium containing LPG at indicated time points and stimulated or not with LPS for 20 h more, at 37° C., 5% $CO_2$. Cells were harvested and disrupted in 150 μl of 0.25 M Tris.Cl, by three freezed-thawed cycles. Supernatants separated by centrifuge (15,000×g, 5 min), were collected and 100 μg of protein extracts (measured by coumassie blue assay, Bio-Rad, Richmond, Calif.), were mixed with $^{14}$C-chloramphenicol (stock 58.6 mCi/mM, DuPont NEN, Boston, Mass.) and acetyl-CoA (Sigma), and incubated at 37° C. for 4 to 12 h, with 5 or 6 h having the greatest induction of CAT activity by LPS compared to unstimulated cells. The organic phase was then extracted using 800 μl ethyl acetate, evaporated in Speed Vacuum, resuspended in 20 μl ethyl acetate and loaded onto a silica gel sheet (Baker-Flex, #IB2-F, Germany). Acetylated $^{14}$C-chloramphenicol forms were separated from non-acetylated forms by thin layer chromatography in chloroform:methanol (95:5) solent system. The dried TLC sheet was exposed to KODAK X-OMAT AR film for 12 to 48 h and quantitated by PhosphoImager for 8 to 24 h. Basal CAT activity in medium condition was subtracted and the percent inhibition was expressed as [1−(relative units from LPG plus inducer/relative units from inducer)]×100. THP-1 monocytes transiently transfected with −1110/+15 constructs responded to endotoxin with an average of 8-fold increase in CAT activity (6 to 18-folds above basal) while that of the −3757/+11 and −3757/−2729 linked to −131/+11 responded to endotoxin with an average of 20-fold and over 30-fold increase in CAT activity, respectively. Zhang, Y., et al., "Mechanisms of Stimulation of Interleukin-1β and Tumor Necrosis Factor-α by *Mycobacterium tuberculosis* Components," *J. Clin. Investig.* 91:2076–83 (1993); Zhang, Y., et al., "Regulation of the Interleukin-1β Gene By Mycobacterial Components and Lipopolysaccharide is Mediated By Two Nuclear Factor-IL-6 Motifs," *Molec. & Cell. Biol.* 13:3831–7 (1993); Shirakawa, F., et al., "The Human proIL-1β Gene Requires Sequences Both Proximal and Distal to the Transcription Start Site For Tissue-Specific Induction," *Molec. Cell. Biol.* 13:1332–44 (1993); and Buras, J. A., et al., "The NF-βA (PU.1)-binding Element, Not An Overlapping NF-IL-6-binding Element, Is Required For Maximal IL-1β Gene Expression," *J. Immunol.* 152:4444–54 (1994).

Example 9

Effect of LPG on IL-1β Induction by LPS

Figure 3:
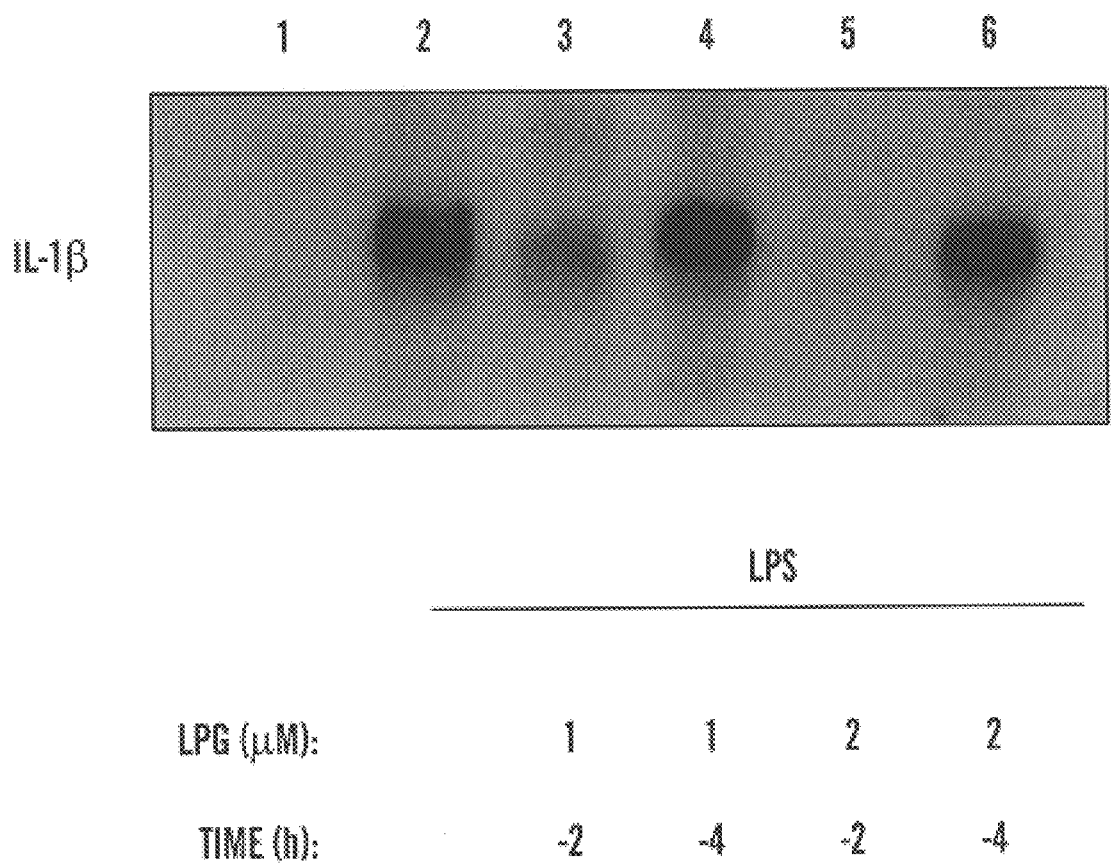
FIG. 3 shows the effect of LPG on IL-1β induction by LPS. THP-1 cells ($10^7$ per condition) pretreated or not with 1 or 2 μM LPG for 2 or 4 h were stimulated or not with 2 μg/ml LPS for 4 h. Total RNA was extracted, 20 μg from each condition was fractionated by electrophoresis on 1.2% agarose-formaldehyde gel and after capillary transfer on nylon membrane was hybridized with a $^{32}$P-labeled cDNA probe of IL-1β. Autoradiographs demonstrating the 1.7 kb IL-1β mRNA are as follows: lane 1, medium; lanes 2 through 6, LPS 2 μg/ml; lanes 3 and 6, pre-treatment for 2 h with LPG 1 μM and 2 μM, respectively; lanes 4 and 6, pretreatment for 4 h with LPG 1 μM and 2 μM, respectively (N=2).

PBMC from patients with VL have depressed in vitro production of IL-1 and TNF-α in response to LPS and heat killed-Listeria. J. L. Ho, R. Badaro, A. Schwartz, C. A. Dinarello, J. A. Gelfand, J. Sobel, A. Barral, M. Barral-Netto, E. M. Carvalho, S. G. Reed, and W. D. Johnson "Diminished Production of Interleukin-1 and Tumor Necrosis Factor-α During Acute Visceral Leishmaniasis and Recovery After Therapy," *J. Infect. Dis.* 165: 094–1102 (1992), which is hereby incorporated by reference. Furthermore, macrophages infected with amastigotes or treated with LPG of promastigotes of L. donovani produced lower amounts of IL-1β in response to LPS. N. E. Reiner, "Parasite Accessory Cell Interaction in Murine Leishmaniasis. Evasion and Stimulus-Dependent Suppression of the Macrophage Interleukin 1 Response by *Leishmania donovani*," *J. Immunol.* 138: 1919–25 (1987); N. E. Reiner, W. Ng, C. B. Wilson, R. McMaster, and S. K. Burchett, "Modulation of in vitro Monocyte Cytokine Response to *Leishmania donovani*. Interferon-γ Prevents Parasite-induced Inhibition of Interleukin-1 Production and Primes Monocytes to Respond to Leishmania by Producing both Tumor Necrosis Factor-α and Interleukin-1," *J. Clin. Invest.* 85: 1914–240 (1990); S. Frankenburg, V. Leibovici, N. Mansbach, S. J. Turco, and G. Rosen, "Effect of Glycolipids of Leishmania Parasites on Human Monocyte Activity," *J. Immunol.* 145: 4284–9 (1990), each of which is hereby incorporated by reference. To define this phenomenon, the effect of LPG on IL-1β mRNA induction was examined. THP-1 cells were pretreated with either 1 or 2 μM LPG for either 2 or 4 h and then stimulated by LPS. As shown in FIG. 3, LPG from *L. donovani* suppressed the induction of IL-1β mRNA by LPS. Compared to cells stimulated with LPS alone, cells pretreated for 2 h with 1 μM LPG had lower amounts of IL-1β mRNA, while cells pretreated with 2 μM LPG had little or no IL-1β mRNA detected in response to LPS. In contrast, the inhibitory activity of LPG at either 1 or 2 μM was lost when LPG was added 4 h before LPS.

Example 10

Time-dependent Effect of LPG Added with LPS on Induction of IL-1β

Figure 4:
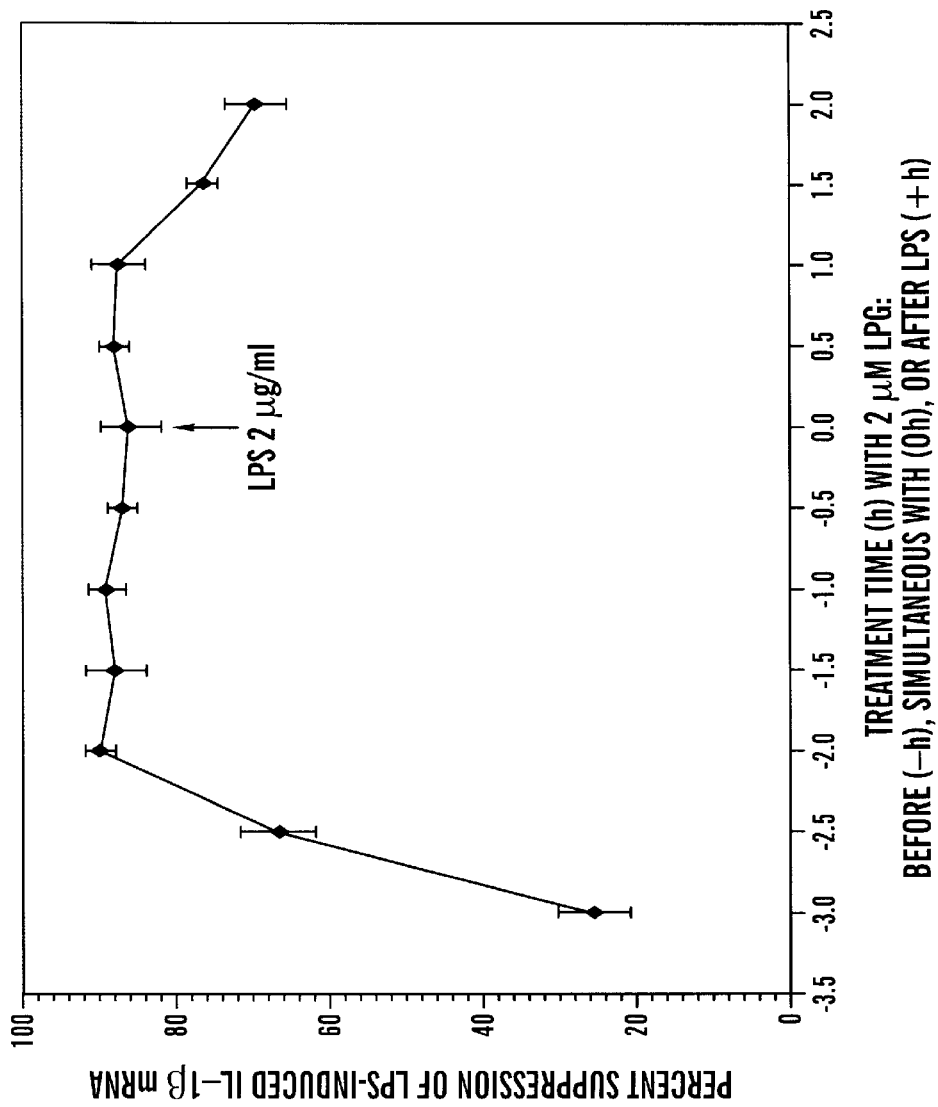
FIG. 4 shows the time-dependent effect of LPG added with LPS on induction of IL-1β. Maximal suppression by LPG of LPS induction of IL-1β mRNA was observed between −2 h and +1 h. Increasing pre-treatment or delaying time of LPG treatment after LPS stimulation resulted in lower inhibition by LPG. THP-1 cells ($10^7$ per condition) were treated with 2 μM LPG at various times in relations to LPS. At zero time cells were stimulated with 2 μg/ml LPS. After 4 h, total RNA was extracted resolved by electrophoresis and IL-1β and GAPDH mRNA were detected and quantitated as described in the legend to FIGS. 3, 4, and 5. Each data point is the mean (±SD) of 3 to 6 separate experiments (FIG. 5). Illustration of one representative experiment's autoradiogram of Northern analysis and photograph of ethidium bromide stained total mRNA. Treatment conditions are as follows: lane 1, medium; lanes 2 through 11, LPS 2 μg/ml; lanes 3 through 11, LPG at designated times before (+h), simultaneous with (0 h), and after (+h) LPS induction.
Figure 5:
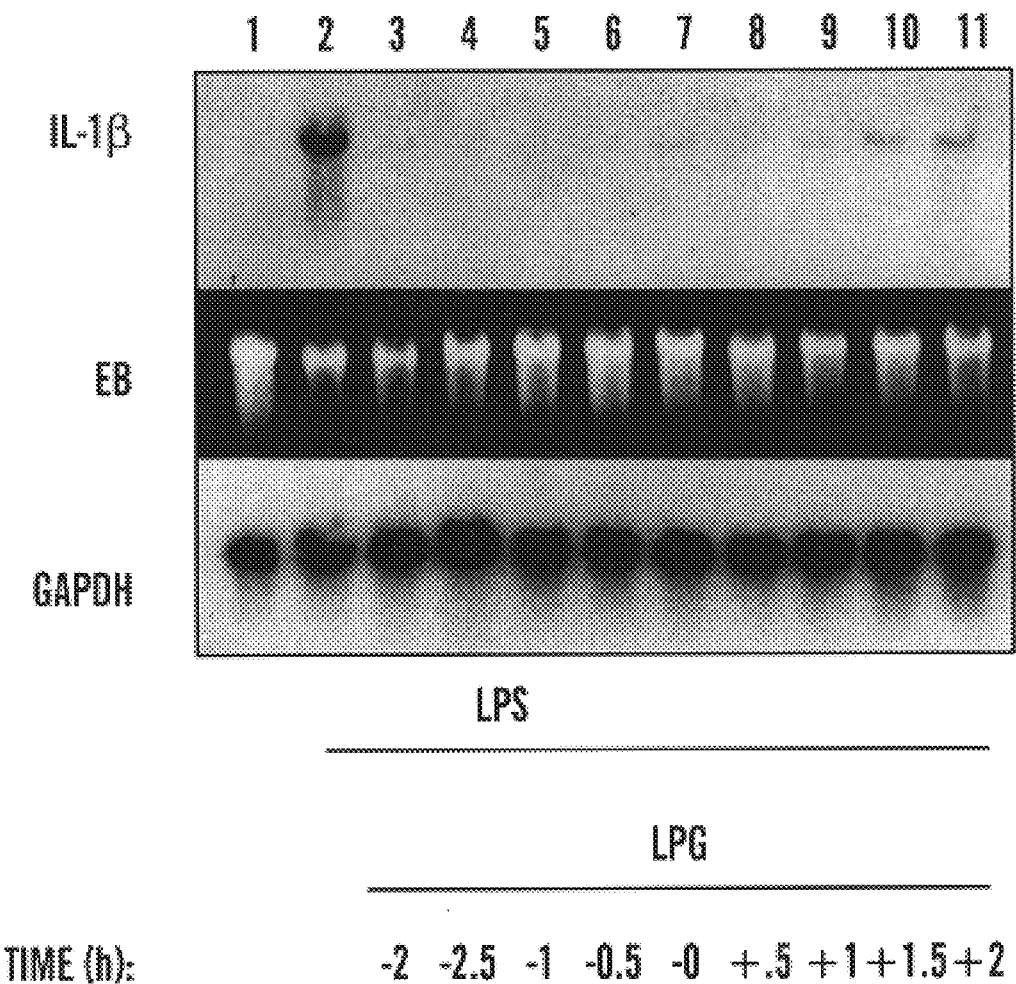
FIG. 5 is an illustration of one representative Northern analysis (autoradiogram) using $^{32}$P-labeled cDNAs of IL-1β and GAPDH demonstrating the respective 1.7 kb and 1.2 kb mRNA, and photograph of ethidium bromide (EB) stained total mRNA. Treatment conditions are as follows: lane 1, medium; lanes 2 through 11, LPS 2 μg/ml; lanes 3 through 11, LPG at designated times in relations to challenge with LPS. THP-1 cells ($10^7$ per condition) treated or not with LPG (1 or 2 μM) for various times before (−h), simultaneous (0 h) or after (+h) challenge with 2 μg/ml LPS. After cultured for 4 h, 37° C., 5% $CO_2$, total RNA from each treatment condition was extracted. Twenty μg from each condition was fractionated by electrophoresis on 1.2% agarose-formaldehyde gel and after capillary transfer on nylon membrane was hybridized with a $^{32}$P-labeled cDNA probe of either IL-1β or GAPDH. The amount of IL-1β and GAPDH mRNAs was detected by autoradiography and quantitated by Phosphor Imager. The percent suppression of LPS-induced IL-1β mRNA was calculated based on the values obtained from the Phosphor Imager Analyzer after normalization with the amount of GAPDH mRNA from each condition. The amount of GAPDH mRNA was similar and varied by less than 5% between conditions.

To characterize further the effect of LPG, the time of LPG treatment in relation to LPS stimulation was examined, as shown in FIG. 4, discussed further below. LPG was added from 4 h before to 2 h after stimulation with LPS. LPG suppressed the LPS induction of IL-1β mRNA by greater than 90% when LPG was added between 2 h before to 1 h after stimulation with LPS (FIGS. 4 and 5, below). Increasing the pre-treatment or delaying the time of LPG treatment after LPS stimulation resulted in reduction of the inhibitory effect of LPG. Treatment with LPG+2 h after LPS stimulation resulted in 70% suppression of IL-1β mRNA. When cells were pretreated with 1 μM or 2 μM LPG for 4 h and then stimulated with 2 μg/ml LPS, the inhibitory effect of LPG was lost resulting in an amount of IL-1β mRNA that was similar to LPS stimulation alone (data shown in FIG. 3). The time-dependent inhibitory effect of LPG on the induction of IL-1β but not GAPDH and mRNA suggests that the effect of LPG is transient and specific.

Example 11

Effect of Varying Concentration of LPG and LPS induction in IL-1β

Figure 6:
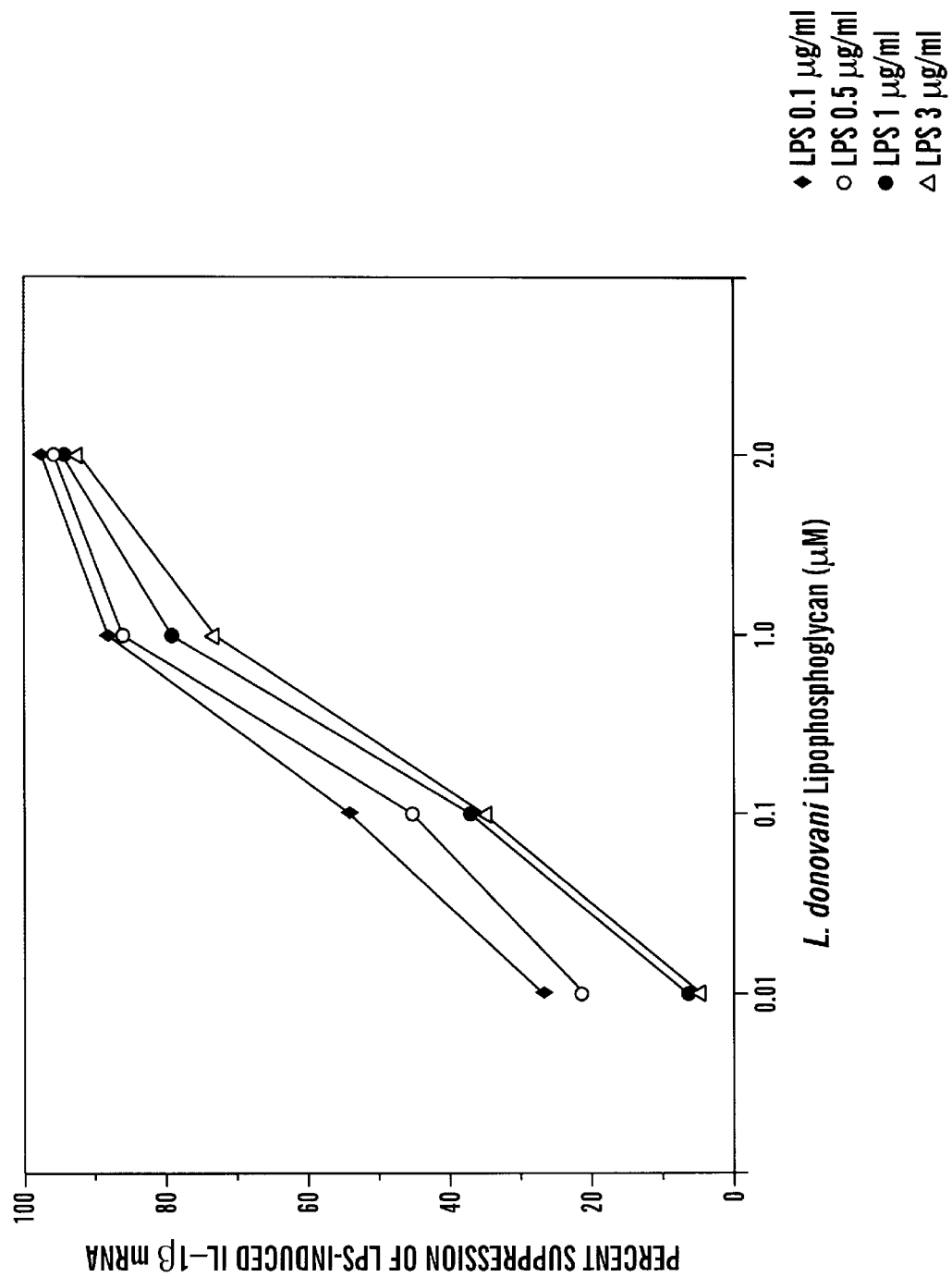
FIG. 6 demonstrates the effect of varying concentrations of LPG on LPS induction of IL-1β mRNA. LPG inhibited the induction of IL-1β mRNA in a dose-dependent manner but not GAPDH. THP-1 cells ($10^7$ per condition), were pretreated for 2 h with LPG from 0.01 μM to 2.0 μM and then stimulated with 0.1 to 3 μg/ml LPS for 4 h. After total TNA extraction, 20 μg of total RNA from each condition fractionated by electrophoresis on 1.2% agarose-formaldehyde gel was probed with $^{32}$P-labeled cDNAs of IL-1β or GAPDH. The amount of IL-1β and GAPDH mRNAs was detected by autoradiography and quantitated by Phosphor Imager. The percent suppression of LPS-induced IL-1β mRNA was calculated based on the Phosphor Imager Analyzer after normalization by the amount of GAPDH mRNA from each condition. The amount of GAPDH mRNA was generally similar and varied by less than 5% between conditions. Each point is the mean of 3 to 4 separate experiments with SD less than 10% of the mean.
Figure 7:
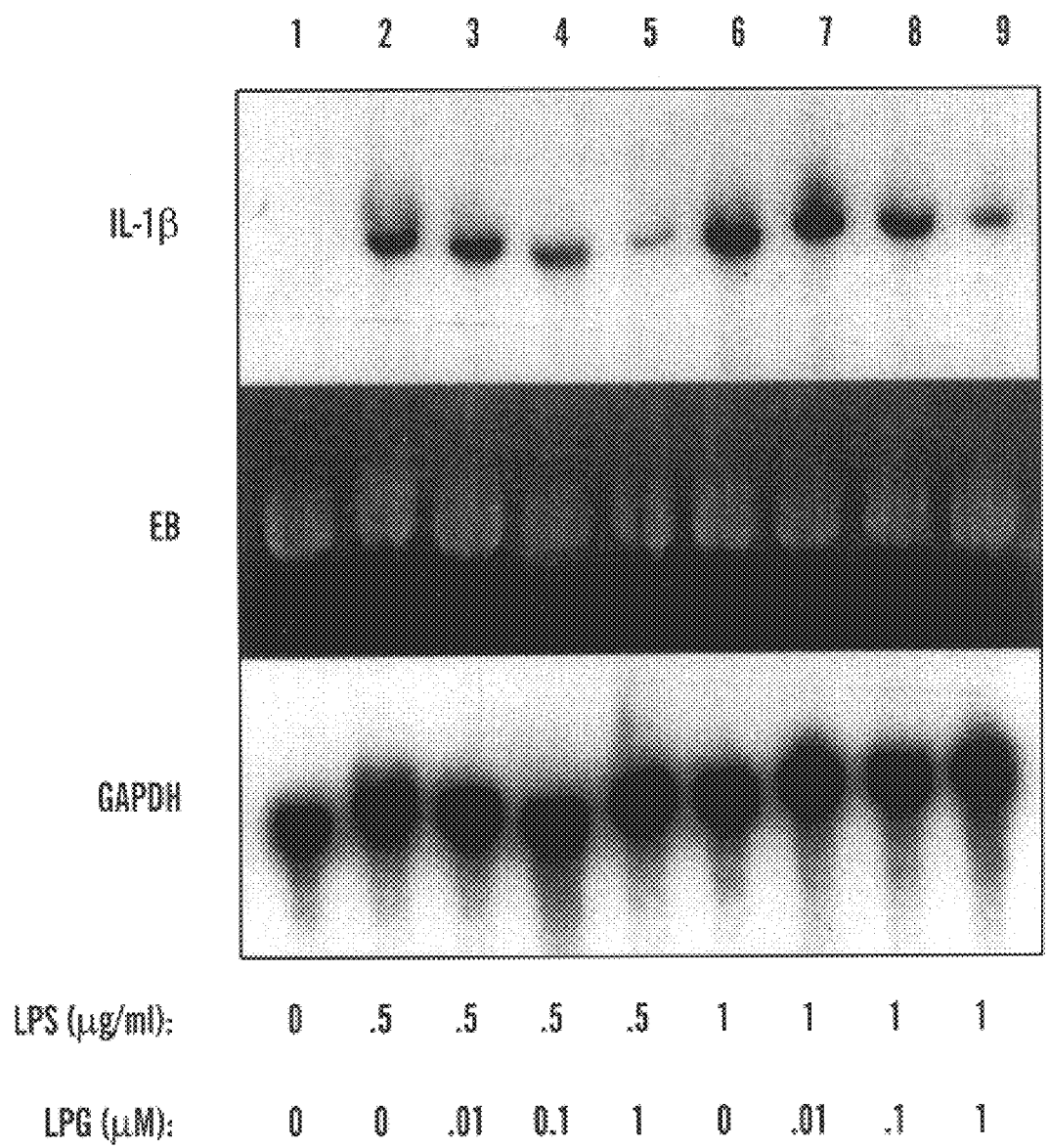
FIG. 7 is an illustration of one representative experiment's autoradiogram of Northern analysis using $^{32}$P-labeled cDNAs of IL-1β and GAPDH demonstrating the respective 1.7 kb and 1.2 kb mRNA, and photograph of ethidium bromide (EB) stained total mRNA after electrophoresis. Treatment conditions are as follows: lane 1, medium; lanes 2 through 5, LPS 0.5 μg/ml; lanes 6 through 9, LPS 1 μg/ml; lanes 3 and 7, LPG 0.01 μM; lanes 4 and 8, LPG 0.1 μM: lanes 5 and 9, LPG 1.0 μM.

To further define the inhibitory effects of LPG, IL-1β mRNA was measured in cells pretreated for 2 h with LPG concentrations ranging from 0.01 µM to 2 µM followed by stimulation with different doses of LPS (FIGS. 6 and 7). Increasing concentrations of LPG from 0.01 to 2.0 µM resulted in a dose-dependent suppression of the amount of IL-1β mRNA that reached a maximum inhibition of greater than 90% (FIG. 6). Increasing the dose of LPS from 0.1 to 3 µg/ml lifted the dose-response curve of the amount of IL-1β mRNA suppressed but did not overcome the inhibition by LPG (FIG. 6). The inhibition of IL-1β mRNA is specific since constitutive transcription of GAPDH mRNA and cell viability were not affected by LPG (FIG. 7 and data not shown).

Example 12

Effect of Removal of LPG or Stimulation with TNF-α, Phorbol 12-myristate 13-acetate (PMA) or S. epidermidis on LPG Inhibition of IL-1β mRNA Expression To further examine the specificity of the suppression of IL-1β mRNA induction, the effect of removal of LPG by washing was evaluated. THP-1 cells treated for 2 h with either medium or medium containing 1 or 2 µM LPG were then washed twice to remove LPG followed by LPS stimulation for an additional 4 h (FIG. 8). Washing to remove LPG had no effect of LPG's ability to supress LPS induction of IL-1β mRNA (FIG. 8, panel 1, lanes 3 and 4 compared with lanes 5 and 6).

To see whether LPG inhibition of IL-1β mRNA was restricted to LPS stimulation, the ability of LPG to suppress IL-1β mRNA induced by other ligands or stimuli was evaluated (FIG. 8, panels 2 and 3). Pretreatment with LPG for 2 h inhibited with induction of IL-1β mRNA by TNF-α but not only PMA (FIG. 8, panels 2A and 2B respectively). The inhibition of the TNF-α induced IL-1β mRNA was approximately 50%±10% (mean±SD,N=5). In contrast, LPG did not suppress PMA induction of IL-1β mRNA while remaining able to inhibit LPS stimulation in the same experiment (N=3).

To further evaluate the discordant effect of LPG on IL-1β mRNA induction by LPS and TNF-α compared to PMA, the effect of LPG on the induction of IL-1β mRNA by S. epidermidis opsonized with serum was examined (FIG. 8, panel 3). LPG treatment simultaneously with S. epidermidis suppressed the amount of IL-1β mRNA by greater than 80±19%, while LPG pretreatment for 2 h inhibited IL-1β mRNA by 30±10% (N=3). In contrast, treatment with LPG 2 h after S. epidermidis induction had minimal to no demonstrable effect on the amount of IL-1β mRNA. To determine whether LPG similarly affected peripheral blood monocytes, the effect of LPG was evaluated in response to LPS and S. epidermidis. Pretreatment for 2 h with 2 µM LPG similarly inhibited LPS (2 µg/ml) and S. epidermidis induction of IL-1β mRNA by greater than 90% and 80%, respectively (N=2). These results confirmed the findings using THP-1 cell line. Based on these observations, it is likely that LPG inhibits IL-1β mRNA by mechanisms not involving competition with binding of LPS to CD14 because: 1) LPG suppressed TNF-α and S. epidermidis induction of IL-1β mRNA, 2) LPG inhibited IL-1β when LPG was added simultaneously with or 2 h after LPS (in contrast, prepared with LPG for 4 h before stimulation with LPS had no effect on IL-1β mRNA expression), and 3) washing cells treated with LPG did not alter the ability of LPG to inhibit subsequent induction of IL-1β mRNA induced by LPS.

Example 13

Effect of LPG on IL-1β mRNA Stability and Transcription

Figure 9:
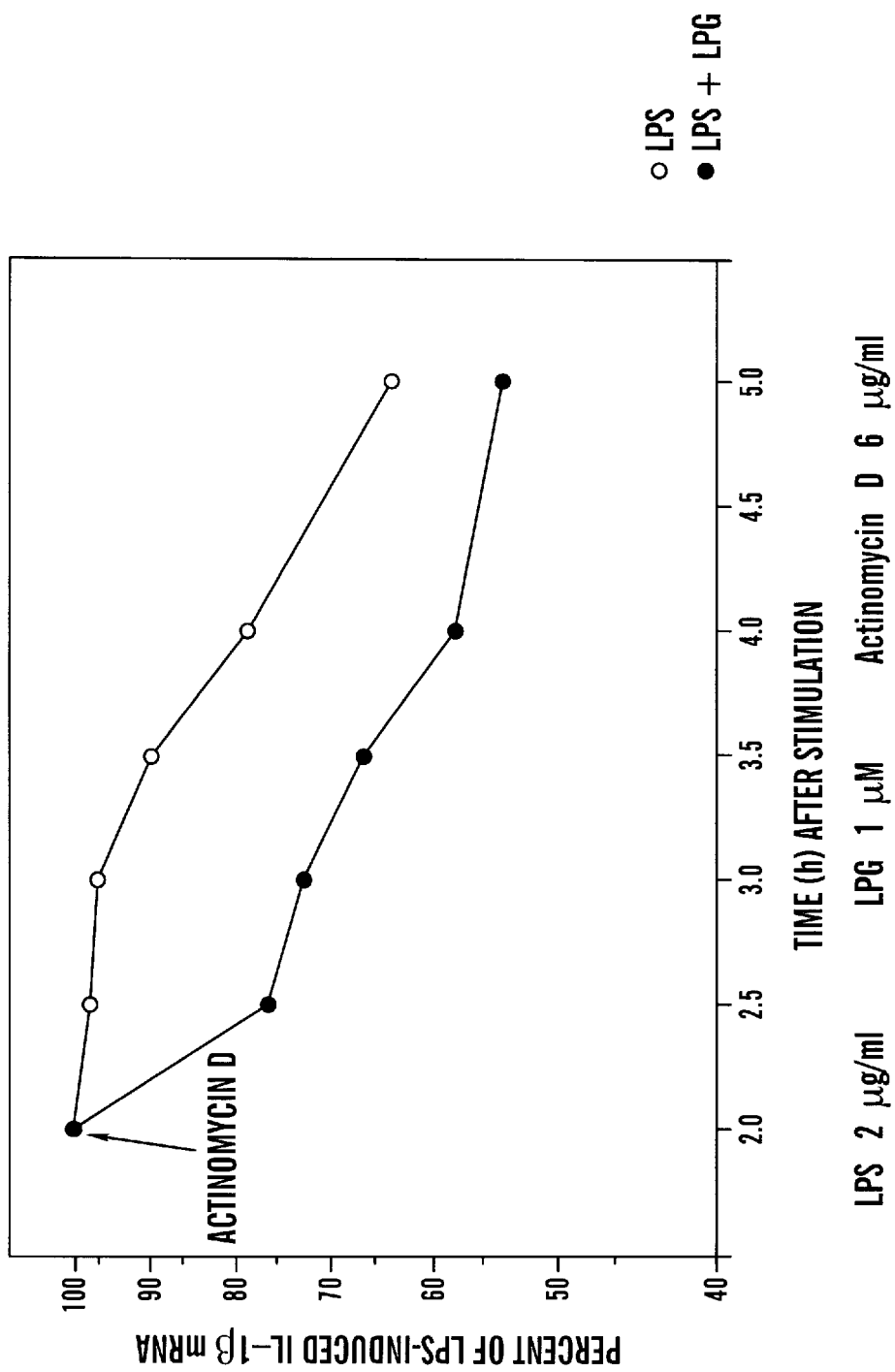
FIG. 9 shows the effect of LPG on IL-1β mRNA stability. LPG enhanced IL-1β mRNA degradation (n=4 separate experiments). THP-1 cells ($10^7$ cells/condition) were treated at time 0 h with 2 μg/ml LPS or 2 μg/ml LPS simultaneously with 2 μM LPG. Actinomycin D (6 μg/ml) was added to all conditions 2 h after treatment with LPS or LPS and LPG, and total RNA was extracted at the designated time (h). IL-1β mRNA stability after LPS or LPS and LPG treatment is illustrated. The amount of IL-1β mRNA present at the 2 hr time point after LPS or LPS plus LPG treatment was used as the reference for comparison with residual IL-1β mRNA at the later times. Each data is the mean of 3 to 4 separate experiments in which the SD was less than 10%.
Figure 10:
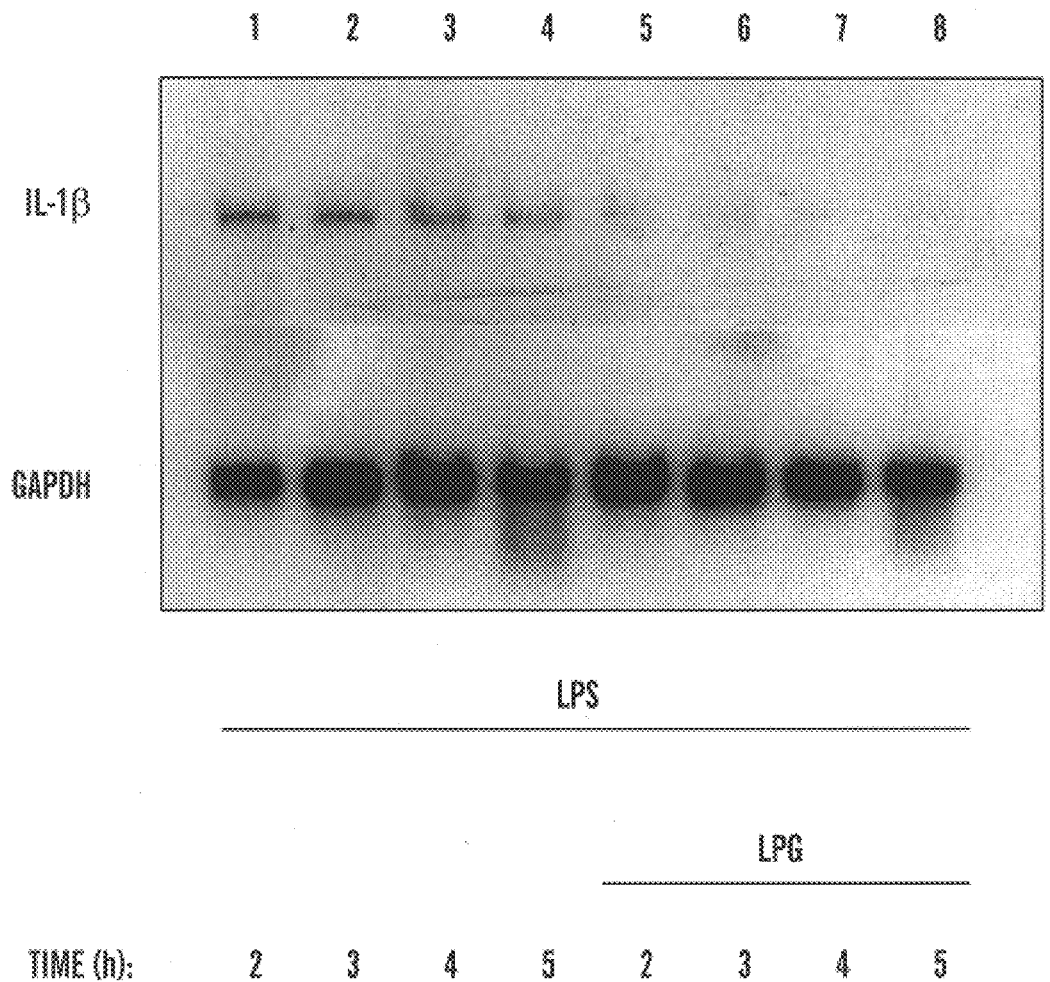
FIG. 10 illustrates a representative autoradiogram of Northern analysis detecting IL-1β and GAPDH mRNAs: lanes 1 to 8, 2 μg/ml LPS, and lanes 5 to 8, 2 μM LPG.

The previous experiments demonstrated that LPG inhibited the steady state level of IL-1β mRNA. To determine whether the reduction in IL-1β mRNA resulting from LPG treatment was due to IL-1β degradation, mRNA stability was examined in cells cultured with actinomycin D, an agent known to block the instigation of mRNA transcription. THP-1 cells treated for 2 h either µg/ml LPS or with 2 µg/ml LPS added simultaneously with 2 µg/ml LPS were cultured with actinomycin D. Treatment with LPG and LPS resulted in an increased rate of IL-1β mRNA degradation compared to LPS stimulation alone (FIGS. 9 and 10). LPG enhanced the rate of IL-1β mRNA degradation by approximately 30%. Since LPG suppressed LPS induction of IL-1β mRNA by over 90% while LPG increased IL-1β mRNA degradation by approximately 30%, the effect of LPG on IL-1β transcription was examined.

A nuclear run-off assay was used to examine the effect of LPG on IL-1β transcription (FIG. 11). LPG induced very high levels of IL-1β transcription. Nuclei of THP-1 cultured in medium had no detectable IL-1β transcripts. Treatment with LPG inhibited the LPS induced IL-1β mRNA transcription by approximately 65%. In contrast, in vitro transcription of GAPDH was similar in each of the treatment conditions, suggesting that the inhibition of LPS induced IL-1β transcription is specific because GAPDH mRNA was not affected by LPG.

Example 14

Effect of LPG on Promoter Regulation of IL-1β Transcription

To determine whether specific nucleotide sequences may regulate the LPG suppression of LPS-induced IL-1β transcription, a 5' IL-1β genomic DNA sequence (−110/+15) isolated from a human placenta genomic library and linked to chloramphenicol acetyl transferase was used. Y. Zhang, M. Doerflier, T. C. Lee, B. Guillemin, and W. N. Rom, "Mechanisms of Stimulation of Interleukin-1β and Tumor Necrosis Factor-α by *Mycobacterium tuberculosis* Components," *J. Clin. Investig.* 91: 2076–83 (1993), which is hereby incorporated by reference. In addition, plasmids containing deletions of this sequence previously constructed (−680/+15, −310/+15, 57//+15) were used to examine the region with the suppressive activity. Y. zhang and W. N. Rom, "Regulation of the Interleukin-1β gene by Mycobacterial Components and Lipopolysaccharide is Mediated by Two Nuclear Factor-IL-6 motifs," *Molec. & Cell. Biol.* 13: 3831–7 (1993), which is hereby incorporated by reference. See FIG. 12. CAT activity in cells transiently transfected with these plasmids are enhanced by a 4- to 19-folds above basal in response to LPS, TNF-α, IL-1β and *Mycobacterium*

*tuberculosis* products. Y. Zhang and W. N. Rom, "Regulation of the Interleukin-1β gene by Mycobacterial Components and Lipopolysaccharide is Mediated by Two Nuclear Factor-IL-6 motifs," *Molec. & Cell. Biol.* 13: 3831–7 (1993); Zhang, Y., M. Doerflier, T. C. Lee, B. Guillemin, and W. N. Rom., "Mechanisms of Stimulation of Interleukin-1β and Tumor Necrosis Factor-α by *Mycobacterium tuberculosis* Components," *J. Clin. Investig.* 91: 2076–83 (1993), which is hereby incorporated by reference.

In THP-1 cells transiently transfected with plasmids containing the 5' flanking regions of IL-1β gene linked to CAT gene, LPG suppressed LPS-induced CAT activity by approximately 40% in plasmids containing the –1110/+15, –680/+15, and –310/+15 promoter sequence (FIG. 12). The major DNA element required for LPG suppression of LPS induction of CAT activity linked to the IL-1 promoter appears to reside within the –310 to –57 region, because of deletion of nucleotides to –57 upstream to the transcriptional start site abrogated the ability of LPG to suppress the LPS-induced CAT activity.

The major DNA sequence required for LPG suppression of endotoxin-induced CAT activity appears to reside within the –310 to –57 region, because truncation of IL-1β promoter nucleotide sequences to –131 abolished most of the LPG's inhibitory activity (reduced to 7%+1% suppression of CAT activity) while deletion to –57 nucleotide sequence upstream to the transcriptional start site completely abrogated LPG's inhibitory activity. In previous reports, the –131 to +12 sequence of the IL-1β promoter was sufficient to direct gene transcription. Shirakawa, F., et al., "The Human proIL-1β Gene Requires Sequences Both Proximal and Distal to the Transcription Start Site For Tissue-Specific Induction," *Molec. Cell. Biol.* 13:1332–44 (1993); Buras, J. A., et al., "The NF-βA (PU.1)-binding Element, Not An Overlapping NF-IL-6-binding Element, Is Required For Maximal IL-1β Gene Expression," *J. Immunol.* 152:4444–54 (1994); Hunninghake, G. W., et al., "The Functional Importance of a Cap Site-Proximal Region of the Human proIL-1β Gene is Defined by Viral Protein Trans-Activation," *Molec. Cell. Biol.* 12:3439–48 (1992); and Kominato, Y., et al., "Monocyte Expression of the Human pro-IL-1β Gene is Dependent on Promoter Sequences Which Bind the Hematopoietic Transcription Factor Spi-1/PU.1," *Molec. Cell. Biol.* 15:58–68 (1995). Therefore, in the present studies the loss of LPG inhibitory activity by truncating the IL1β promoter to –131 region shows that upstream sequences from –310 to at least –131 contain LPG inhibitory response DNA sequence(s).

Previous reports have described a cell-type-independent endotoxin-responsive enhancer region upstream to the –1110/+15 region of the IL-1β promoter located between nucleotide sequences –3757 and –2729. Buras, J. A., et al., "The NF-βA (PU.1)-binding Element, Not An overlapping NF-IL-6-binding Element, Is Required For Maximal IL-1β Gene Expression," *J. Immunol.* 152:4444–54 (1994) and Luqman, M., et al., "Differential Effect of Interleukin 1 on Naive and Memory CD4+ T Cells," *Eur. J. Immunol.* 22:95–100 (1992). Within the –3757 to –2729 IL-1β promoter sequence, six subregions are essential for the maximal endotoxin-induced transcriptional activity in transfected monocytes. It was, therefore, examined whether LPG can inhibit endotoxin-induced transcription under the regulation of the endotoxin response elements contained in the –3757 to –2729 promoter region. Using the full-length IL-1β construct –3757 to +11 (named, XT-CAT, FIG. 13A), human THP-1 monocytes were transiently transfected to delineate the effect of LPG on endotoxin-induced CAT activity. Compared to basal CAT activity, endotoxin-induced CAT activity was increased by over 20-fold. Pretreatment with LPG 2 μM for 1 h suppressed endotoxin-induced CAT activity by 50%+5% (n=5) (FIG. 12B). The finding that LPG can inhibit IL-1β transcription in the presence of the major upstream cell-independent endotoxin-enhancer region lends support for a LPG-inhibitory DNA element(s) residing in the –310 to –57 nucleotide region.

To provide direct support that an LPG-inhibitory DNA element(s) resides in the –310 to –57 nucleotide sequence, the IL-1β promoter construct, namely X2-HT-CAT (–3757 to –2729 directly linked to –131 to +11), in which the –2729 to –131 nucleotide sequence has been deleted from the full-length IL-1β promoter, was used (FIG. 13A). THP-1 monocytes were transiently transfected with X2-HT-CAT or with the full-length promoter, XT-CAT. Monocytes transiently transfected with X2-HT-CAT responded to endotoxin (2 μg/ml) by increasing CAT activity by over 30-fold from basal. In cells transfected with the deletional mutant construct X2-HT-CAT, pretreatment with LPG (2 μM, 1 h) suppressed endotoxin-induced CAT activity by 8%+4%; while, in the same cells transfected with the full-length IL-1β promoter, LPG inhibited endotoxin-induced CAT activity by 50%+5%. In total, these findings suggest that an unique LPG-inhibitory response DNA sequence is located in the –310 to –57 region of the IL-1β promoter.

Example 15

Dose- and Time-dependent Effect of LPG on Promoter Regulation of IL-1β

To further characterize the effect of LPG on the promoter regulation of IL-1β gene, experiments were performed on the dose and time effect of LPG on the plasmid containing the –310/+15 IL-1β promoter sequence (FIGS. 14 and 15). Using this plasmid, the dose and time profiles of LPG suppression of LPS-induced CAT activity were similar to that of steady state mRNA. These data provided additional evidence that LPG suppression of IL-1β mRNA is transcriptionally regulated and by a specific promoter sequence.

LPG on the promastigote of Leishmania is essential for the initial survival within macrophages. T. B. McNeely and S. Turco, "Requirements of Lipophosphoglycan for Intracellular Survival of *Leishmania Donovani* Within Human Monocytes," *J. Immunol.* 144: 2745–50 (1990); S. Frankenburg, A. Gross, and V. Leibovici, "*Leishmania major* and *Leishmania donovani*: Effect of LPG-containing and LPG-deficient Strains on Monocyte Chemotaxis and Chemiluminescence," *Exp. Parsitol* 75: 442–8 (1992), each of which is hereby incorporated by reference. The exogenous addition of LPG to LPG-deficient Leishmania renders the susceptible parasite resistant to macrophage killing. E. Handman, L. F. Schnur, T. W. Spithill, and G. F. Mitchell, "Passive Transfer of Leishmania Lipopolysaccharide Confers Parasite Survival in Macrophages," *J. Immunol.* 137:3608–13 (1986), which is hereby incorporated by reference. LPG is likely shed during entry into the macrophage, because, within 5 to 10 min after Leishmania promastigote infection of macrophages, LPG epitopes are observed on the external membrane of the macrophage. D. L. Tolson, S. J. Turco, and T. W. Pearson, "Expression of a Repeating Phosphorylated Disaccharide Lipophosphoglycan Epitope on the Surface of Macrophages Infected with *Leishmania donovani*," *Infect. Immun.* 58: 3500–7 (1990), which is hereby incorporated by reference. LPG may mediate the modification of macrophage functions for parasite survival, because macrophages treated with LPG have diminished chemotaxis, generation of reactive oxygen radicals, and oxygen consumption, production of IL-1 and induction of TNF-α gene expression. T. B. McNeely and S. Turco, "Requirements of Lipophosphoglycan for Intracellular Survival of *Leishmania donovani* Within Human Monocytes," *J. Immunol.* 144: 2745–50 (1990); S. Frankenburg, V. Leibovici, N. Mansbach, S. J. Turco, and G. Rosen, "Effect of Glycolipids of Leishmania Parasites on Human Monocyte Activity," *J. Immunol.* 145: 4284–9 (1990); S. Frankenburg, A. Gross, and V. Leibovici, "*Leishmania major* and *Leishmania donovani*: Effect of LPG-containing and LPG-deficient Strains on Monocyte Chemotaxis and Chemiluminescence," *Exp. Parsitol* 75: 442–48 (1992); A. Descoteaux and G. Matlashewski, "C-fos and Tumor Necrosis Factor Gene Expression in *Leishmania donovani*-infected Macrophages," *Molecular Cell Biol.* 9: 5223–7 (1989), each of which is hereby incorporated by reference. However, the molecular mechanisms by which LPG alters human macrophage function resulting in survival of the parasite within macrophages have not previously been elucidated.

In this work, LPG from *L. donavani* down-modulated IL-1β gene expression in THP-1 human monocytic cells and peripheral blood monocytes. The suppression by LPG of LPS induced IL-1β mRNA was dose- and time-dependent. LPG suppression of IL-1β induction was not limited to LPS but also inhibited the induction by TNF-α and *S. epidermidis*. The effect of LPG appears to be specific, because GAPDH mRNA was not affected, the PMA-induction of IL-1β was not suppressed by LPG, and LPG did not inhibit LPS-induction of IL-1β mRNA when cells were pretreated with LPG 4 h before LPS.

The suppression of LPS-induction of IL-1β mRNA by LPG appears to be mediated in part by increasing mRNA degradation by approximately 30% and decreasing transcription by approximately 65%. The sum of these two effects of LPG accounts for the observed reduction in steady state IL-1β mRNA. Additional support for transcriptional alteration is provided by the finding that inhibition of LPS-induction of TNF-α mRNA was similarly suppressed in a nuclear run-off assay (FIG. 29, N=3). An IL-1β promoter gene sequence was believed to respond to LPG and thereby inhibit IL-1β gene transcription. Using two IL-1β promoter sequences, a full-length (−3757/+11) and a smaller segment (−1110/+15), it was found that both contained LPG inhibitory response sequence(s). The −310 to −57 DNA segment of the IL-1 promoter was also demonstrated to contain the LPG inhibitory response sequence because the truncated promoters, 131/+15 and −57/+15 possess respectively, minimal (7%) and no LPG inhibitory activity, and the X2-HT-CAT deletional mutant (in which the −2729 to −131 nucleotide sequence had been removed from the −3727/+11 full-length promoter) similarly possess minimal (8%) LPG inhibitory activity. This region mediates the suppression of LPS-induced IL-1β gene transcription, because the LPG inhibition of LPS-induced CAT activity in a plasmid containing −310/+15 has a time-and dose-dependent profile similar to the time-and dose-dependent suppression of LPS induction of IL-1β mRNA. Furthermore, in preliminary data, LPG treatment of THP-1 cells induced the presence of a nuclear protein(s) that bound a DNA sequence derived from this region in a gel shift assay. Therefore, LPG, a molecule that confers promastigote survival within macrophages, alters macrophage gene regulation by increasing IL-1β mRNA degradation by an undefined mechanism and by inhibiting gene transcription by possibly inducing a transcription repressor.

Applicants previously reported that several transcription enhancers are present within the −310/+15 nucleotide sequences of the 5' flanking region of the IL-1β gene. These enhancer sites included: two NF-IL6, binding sites for nuclear binding protein(s) to the IL-6 gene; OCTA, octamer binding site; AP-1, activating protein 1; and SRE, serum responsive element.

Furthermore, the two NF-IL6 motifs were required for IL-1β gene expression induced by LPS, TNF-α and *Mycobacterium tuberculosis* lipoarabinomannan. Y. Zhang, M. Doerflier, T. C. Lee, B. Guillemin, and W. N. Rom., "Mechanisms of Stimulation of Interleukin-1β and Tumor Necrosis Factor-α by *Mycobacterium tuberculosis* Components," *J. Clin. Investig.* 91: 2076–83 (1993), which is hereby incorporated by reference. Additional enhancer sites within the −200/+15 promoter region of the IL-1β gene found in the published promoter sequence in GeneBank included: NF-E1-CS1, NF-E1.4, NF-E1.6, and JCV-repeated-sequence. L. Wall, E. deBoer, and F. Grosveld, "The Human β-globulin Gene 3' Enhancer Contains Multiple Binding Sites for an Erythroid-specific Protein," *Genes & Develop.* 2: 1989–1100 (1988); P. Ghazal, H. Lubon, B. Fleckenstein, and L. Hennighausen, "Binding of Transcription Factors and Creation of a Large Nucleoprotein Complex on the Human Cytomegalovirus Enhancer," *Proc. Natl. Acad. Sci. USA*. 84: 3658–62 (1987), each of which is hereby incorporated by reference. LPG may diminish IL-1β transcription by altering the binding and/or activation of DNA binding protein to enhancer sequences. Alternatively, LPG may induce an unidentified nuclear binding protein(s) that acts as a transcription repressor. The finding that treatment with LPG alone, but not in medium-treated nuclei, induced the presence of DNA binding protein(s) to DNA sequences derived from this region suggests the latter as likely possibility. The potential that a parasite product modulates gene regulation in cells of another genus has precedence, because sodium salicylate, a product of plants, has been reported to activate human NFkB, root-knot nematode has been shown to direct expression of a plant root-specific gene necessary for root modification and nematode development, and *M. tuberculosis* lipoarabinomannan induced IL-1β gene expression in human monocytes via the two nuclear factor-IL6 motifs. E. Kopp and S. Ghosh, "Inhibition of NF-kB by Sodium Salicylate and Aspirin," *Science* 265: 956–9 (1994); C. H. Opperman, C. G. Taylor, and M. A. Conkling, "Root-knot Nematode-directed Expression of a Plant Root-specific gene," *Science* 263: 221–3 (1994); Y. Zhang and W. N. Rom, "Regulation of the Interleukin-1β Gene by Mycobacterial Components and Lipopolysaccharide is Mediated by Two Nuclear Factor-IL-6 Motifs," *Molec. & Cell. Biol.* 13: 3831–7 (1993), each of which is hereby incorporated by reference.

Human macrophages infected with Leishmania amastigotes or treated with LPG have suppressed production of bioactive IL-1 in response to LPS and Staphylococcus. G. D. Crawford, D. J. Wyler, and C. A. Dinarello, "Parasite-monocyte Interactions in Human Leishmaniasis: Production of Interleukin-1 in vitro," *J. Infect. Dis.* 152: 315–322 (1985); N. E. Reiner, W. Ng, C. B. Wilson, R. McMaster, and S. K. Burchett, "Modulation of in vitro Monocyte Cytokine Response to *Leishmania donovani*. Interferon-γ Prevents Parasite-induced Inhibition of Interleukin-1 Production and Primes Monocytes to Respond to Leishmania by Producing Both Tumor Necrosis Factor-α and Interleukin-1," *J. Clin. Invest.* 85: 1914–24 (1990); S. Frankenburg, V. Leibovici, N. Mansbach, S. J. Turco, and G. Rosen, "Effect of Glycolipids of Leishmania Parasites on Human Monocyte Activity," *J.*

*Immunol.* 145: 4284–9 (1990), which are hereby incorporated by reference. Based on these observations, it is likely that *L. donavani* possess both LPG dependent and independent mechanisms for macrophage deactivation because amastigotes of *L. donovani* apparently cannot synthesize LPG and have at most 100 molecules of residual LPG per cell (M. J. McConville and J. M. Blackwell, "Developmental Changes in the Glycosylated Phospatidylinositols of *Leishmania donovani,*" *J. Biol. Chem.* 266: 15170–9 (1990), which is hereby incorporated by reference and because the inhibitory activity of LPG is at the micromolar ranges, as observed above and by others. S. Frankenburg, V. Leibovici, N. Mansbach, S. J. Turco, and G. Rosen, "Effect of Glycolipids of Leishmania Parasites on Human Monocyte Activity," *J. Immunol.* 145: 4284–9 (1990), which is hereby incorporated by reference. The reduced production of bioactive IL-1β in response to LPS reported in macrophages infected with *L. donovani* amastigotes was presumed to be perturbed translation of IL-1β, because the amount of steady state IL-1β mRNA induced by LPS was similar in control and in amastigote-infected macrophages. N. E. Reiner, W. Ng, C. B. Wilson, R. McMaster, and S. K. Burchett, "Modulation of in vitro Monocyte Cytokine Response to *Leishmania donovani.* Interferon-γ Prevents Parasite-Induced Inhibition of Interleukin-1 Production and Primes Monocytes to Respond to Leishmania by Producing Both Tumor Necrosis Factor-α and Interleukin-1,"*J. Clin. Invest.* 85: 1914–24 (1990), which is hereby incorporated by reference. The difference between these findings is most likely attributed to treatment with LPG in the above experiments while Reiner et al. examined amastigote-infected monocytes. Other potential differences included time of induction and the use of THP-1 cell lines rather than monocytes. However, THP-1 cells are functionally very similar to monocytes. S. Tsuchiya, M. Yamabe, Y. Yamaguchi, Y. Kobayashi, T. Konno, T. Konno, and K. Tada, "Establishment and Characterization of a Human Acute Monocytic Leukemic Cell Line (THP-1)," *Int. J. Can.* 26: 171–6 (1980); S. Tsuchiya, Y. Kobayashi, Y. Goto, H. Okumura, S. Nakae, T. Konno, and K. Tada, "Induction of Maturation in Cultured Human Monocytic Leukemia Cells by a Phorbol Diester," *Can. Res.* 42: 1530–6 (19820; Y. Zhang and W. N. Rom, "Regulation of the Interleukin-1β Gene by Mycobacterial Components and Lipopolysaccharide is Mediated by Two Nuclear Factor-IL-6 Motifs," *Molec. & Cell. Biol.* 13: 3831–7, which are all hereby incorporated by reference.

This work did not directly address the potential signaling events whereby LPG modulates gene expression. The finding that LPG is present on macrophage cell membrane as early as 5 to 10 minutes post-infection with *L. donovani* suggests that it likely alters cell function via some membrane event. D. L. Tolson, S. J. Turco, and T. W. Pearson, "Expression of a Repeating Phosphorylated Disaccharide Lipophosphoglycan Epitope on the Surface of Macrophages Infected with *Leishmania donovani,*" *Infect. Immun.* 58: 3500–7 (1990), which is hereby incorporated by reference. One potential mechanism by which LPG interferes with LPS signaling may be by competing for LPS binding protein or by binding to CD14, because LPG and LPS are both glycolipids. M. M. Wurfel, S. T. Kunitake, H. Lichenstein, J. P. Kane, and S. D. Wright, "Lipopolysaccharide (LPS)-binding Protein is Carried on Lipoproteins and Acts as a Cofactor in the Neutralization of LPS," *J. Exp. Med.* 180: 1025–35 (1994), which is hereby incorporated by reference. However, this appears unlikely because: 1) LPG suppressed TNF-α and *S. epidermidis* induction of IL-1β mRNA, 2) LPG inhibited IL-1β when LPG was added simultaneously with or 2 h after LPS (in contrast, pretreatment with LPG for 4 h before stimulation with LPS had no effect on IL-1β expression), and 3) washing cells treated with LPG did not alter the ability of LPG to inhibit subsequent induction of IL-1β mRNA by LPS. To exclude this possibility conclusively, investigations are required to determine the effect of competition between LPG and LPS or to quantitate binding of LPS/LPS binding protein to CD14 in the presence of LPG.

One potential mechanism by which LPG alters IL-1β gene expression may be an LPG interaction with macrophages to trigger an undefined signaling pathway leading to suppression of LPS-induced gene expression. Supporting this interpretation are the findings that: 1) LPG inhibited by 70% the induction of IL1β by LPS even when LPG was added 2 h after LPS; 2) a DNA sequence in the −310 to −57 region of the IL-1β promoter mediated the suppressive effect of LPG; 3) in preliminary experiments, treatment of cells with LPG alone induced nuclear DNA protein(s) that binded to the same region, mediating the suppressive effect of LPG; and 4) LPG similarly inhibited LPS-induction of TNF-α mRNA and appeared, in part, to be mediated by inhibition of transcription. In addition to this work, it previously reported that treatment for 30 min with LPG alone induced the expression of c-fos and TNF-α. A. Descoteaux, S. Turco, D. L. Sacks, and G. Matlashewski "*Leishmania donovani* Selectively Inhibits Signal Transduction in Macrophages." *J. Immunol.* 146: 2747–53, which is hereby incorporated by reference.

Alternative explanations include: 1) the ability of LPG and glycosylphosphatidylinositol antigens of Leishmania to inhibit protein kinase C (PKC) activity directly when both are mixed in vitro. T. B. McNeeley and S. J. Turco, "Inhibition of PKC Activity by *Leishmania donovani* Lipophosphoglycan," *Biochem. Biophys. Res. Comm.* 148:653 (1987); McNeely, T. B. et al., "Inhibitory Effects on Protein Kinase C Activity by Lipophosphoglycan Fragments and Glycosylphosphatidylinositol Antigens of the Protozoan Leishmania," *Biochem. J.* 259:601–4 (1989); Ho, et al., "Cetaceans in the Treatment of Leishmaniasis: From Studies of Immunopathology to Patient Therapy," *Biotherapy* 7:223–35 (1994), which are hereby incorporated by reference) the altered activation and translocation of PKC in amastigote-infected macrophages may be a consequence of dephosphorylation of PKC by cellular phosphatases induced by amastigotes or by egress of Leishmania phosphatase from the phagosome (Olivier, M., et al., "Defective Stimulus-Response Coupling in Human Monocytes Infected With *Leishmania donovani* is Associated With Altered Activation and Translocation of Protein Kinase C," *Proc. Natl. Acad. Sci. USA* 89:7481–85 (1992) and Turco, et al., "The Lipophosphoglycan of Leishmania Parasites," *Annu. Rev. Microbiol.* 46:65–94 (1992), which are hereby incorporated by reference) the insertion of LPG into the lipid bilayer resulting in altered receptor signaling. L. Miao, A. Stafford, S. Nir, S. J. Turco, T. D. Flanagan, and R. M. Epand, "Potent Inhibition of Viral Fusion by Lipophosphoglycan of *Leishmania donovani,*" *Biochem.* 34:4676–83 (1995).

LPG from *L. donovani* down-modulates IL-1β gene expression by multiple stimuli and by two distinct mechanisms, providing an explanation for deactivation in Leishmania-parasitized macrophages and defective T-cell response in patients with leishmaniasis. IL-1β produced by macrophages and other antigen-presenting cells is a co-stimulus for memory T-cell activation and proliferation, and triggers T-cell production of IL-2. M. Luqman, L. Greenbaum, D. Lu, and K. Bottomly, "Differential Effect of Interleukin 1 on Naive and Memory CF4 T cells," *Eur. J. Immunol.*, 22:95–100 (1992); P. H. Stein and A. Singer, "Similar Co-stimulation Requirements of CD4+ and CD8+ Primary T Helper Cells: Role of IL-1 and IL-6 in Inducing IL-2 Secretion and Subsequent Proliferation," *Int. Immunol.*, 3:327–35 (1992), which are hereby incorported by reference. IL-1β also directly activates human macrophage anti-Leishmania activity in vitro. D. H. Hatzigeorgiou, S. H. He, J. Sobel, A. Hafner, K. Grabstein, and J. L. Ho, "Interleukin-6 Down-modulates Cytokine-enhanced Antileishmanial Killing," *J. Immunol.*, 151:3682–92 (1993), which is hereby incorporated by reference. In addition, IL-1β plays an obligate role in a native host for in vivo activation of macrophages against Listeria, another intracellular microbe, that is distinct from the generation of natural killer cell-derived IFN-γ or in induction of antigen specific CD4 and CD8+ T-cells. H. W. Rogers, K. C. F. Sheehan, L. M. Brunt, S. K. Dower, E. R. Unanue, and R. D. Schreiber, "Interleukin 1 Participates in the Development of Anti-Listeria-Response in Normal and SCID Mice," *Proc. Natl. Acad. Sci. USA.*, 89:1011–15 (1992), which is hereby incorporated by reference. Therefore, infection of macrophages, without triggering IL-1β production and inhibition of IL-1β induction by other stimuli, may be an important mechanism for evasion of macrophage activation necessary for containment of the promastigote intracellular infection and subsequent development of CMI. In addition, *L. donovani* infection of macrophages in vitro does not trigger the production of TNF-α (N. E. Reiner, et al., "Modulation of In Vitro Monocyte Cytokine Responses To *Leishmania donovani*—Interferon-γ Prevents Parasite-Induced Inhibition of Interleukin 1 Production and Primes Monocytes to Respond to Leishmania by Producing Both Tumor Necrosis Factor-α and Interleukin 1," *J. Clin. Invest.* 85:1914–24 (1990), which is hereby incorporated by reference), and LPG treatment of murine and human monocytic cells significantly suppressed TNF-α induction by LPS. A. Descoteaux and G. Matlashewski, "C-fos and Tumor Necrosis Factor Gene Expression in *Leishmania donovani*-infected Macrophages," *Molecular Cell Biol.*, 9:5223–7 (1989), which is hereby incorporated by reference. Since TNF-α induces natural killer-cell activation and production of IFN-γ, a cytokine that is required for macrophage activation and Th1 cell development, infection of macrophages without TNF-α and IL-1β generation, increases the probability for intracellular survival of Leishmania and the likelihood for the development of clinical disease. G. J. Bancroft, R. D. Scheiber, and E. R. Unanue, "Natural Immunity: A T-cell-independent Pathway of Macrophage Activation, Defined in the scid Mice," *Immunol. Rev.*, 124:5–24 (1991); K. Varkla, R. Chatelain, L. M. C. C. Leal, and R. L. Coffman, "Reconstitution of C.B-17 SCID Mice with BALB/c T Cells Initiates a T Helper Type-1 Response and Renders Them Capable of Healing Leishmania Major Infection," *Eur. J. Immunol.*, 23:262–268 (1992); L. Morris, A. B. Troutt, E. Handman, and A. Kelso, "Changes in the Precursor Frequencies of IL-4 and IFN-γ Secreting CD4 Cells Correlate with Resolution of Lesions in Murine Cutaneous Leishmaniasis," *J. Immunol.*, 149:2715–2721 (1992); T. M. Scharton and P. Scott, "Natural Killer Cells are a Source of IFN-γ that Drives Differentiation of CD4+ T Cell Subsets and Induces Early Resistance to *Leishmania major* in Mice," *J. Exp. Med.*, 178:567–77 (1993), which are hereby incorporated by reference.

LPG treatment of monocytes suppressed LPS induction of IL1β mRNA by greater than 90% while having no effect on the expression of glyceraldehyde-3-phosphate dehydrogenase mRNA. LPG also inhibited the induction of IL-1β by the cytokine TNF-α and *Staphylococcus epidermidis* but not by phorbol 12-myristate 13-acetate. The suppression by LPG of IL-1β induction was mediated by enhancing mRNA degradation and diminishing transcription that required the nucleotide sequences from the −310 to −57 region of the IL-1β promoter. These results suggest that LPG alters monocyte/macrophage gene regulation to depress cellular immunity and for intracellular survival.

Examples 16–30 relate to structural functional analysis of Leishmania lipophosphoglycan, particularly to distinct domains that mediate binding an inhibition of endothelial cell function.

Example 16

Materials

Reagents used and respective manufacturer were as follows: RPMI-1640, medium 199, and Limmulus amebocyte assay (BioWhittaker, Walkersville, Md.); Dulbecco's modified Eagle's medium, human albumin, fetal bovine serum, penicillin/streptomycin and L-glutamine (GIBCO, Grand Island, N.Y.); bacterial lipopolysaccharide ([endotoxin from *E. coli*, J5] Calbiochem, La Jolla, Calif.); 96-well plates (Falcon, Becton Dickson, Lincoln, N.J.); TNF-α (Genentech, Inc., San Francisco, Calif.); secondary FITC-labelled $F(a)'_2$ goat anti-mouse IgM antibody and isotypic murine IgM mAb (Jackson Immunoresearch Lab., West Grove, Pa.); collagenase (Worthington Biochemical Corp., Freehold, N.J.); paraformaldehyde (Electron Microscopy Sciences, Ft. Washington, Pa.); RNA STAT-60 solution (TEL-TEST "B" Inc., Friendswood, Tex.); nylon membrane (0.45 μm pore size, NYTRAN, S&S, Keene, N.H.); random-priming kit (Boehringer Mannheim GmbH, Mannheim, Germany); plasmid containing GAPDH cDNA ([cat. #57090], American Type Culture Collection [ATCC], Rockville, Md.), plasmid containing the IL-1β cDNA (from Dr. Steve Gillis, Immunex Corp., Seattle, Wash.); and KODAK X-OMAT AR films (Kodak Corporation, Rochester, N.Y.). All reagents and media used for cell culture were checked for presence of endotoxin and found to contain <10 pg/ml as determined by Limmulus amebocyte lysate assay.

Example 17

Leishmania and Lipophosphoglycan (LPG) and LPG Fragments

*Leishmania donovani* (strain Ld3) were cultured in supplemented medium 199 at 25° C. Orlandi, et al., "Structure of the Lipid Moiety of the *Leishmania donovani* Lipophosphoglycan," *J. Biol. Chem.* 262:10384–91 (1987); Hatzigeorgiou, et al., "Interleukin-6 Down-Modulates Cytokine-Enhanced Antileishmanial Killing," *J. Immunol.* 151:3682–92 (1993), which are hereby incorporated by reference. To evaluate binding of Leishmania to human umbilical vein endothelial cells or monocytic cells, stationary or late-log phase metacyclic promatigotes washed 2× in RPMI 1640 medium-10% FBS were co-incubated at a ratio of 20 to 40 promastigotes to vascular cells for varying times (15 min to 2 h). Unattached promastigotes were removed by 3×washing. Vascular cells were directly applied onto glass slides and allowed to air-dry. Immunostaining for LPG using mAb on parasites associated with vascular cells is detailed below (Indirect Immunofluorescence). To evaluate intracellular infection, promastigotes as described above were co-incubated with endothelial cells for 2 h. After washing to remove unassociated promastigotes endothelial cells with associated parasites were further cultured in growth medium at 37° C. for 2 to 3 days. Intracellular parasites were visualized under microscopy after staining with acridine orange. Hatzigeorgiou, et al., "Interleukin-6 Down-Modulates Cytokine-Enhanced Antileishmanial Killing," *J. Immunol.* 151:3682–92 (1993), which is hereby incorporated by reference.

Intact LPG was isolated and purified from *Leishmania donovani* promastigotes as detailed previously. Orlandi, et al., "Structure of the Lipid Moiety of the *Leishmania donovani* Lipophosphoglycan," *J. Biol. Chem.* 262:10384–91 (1987), which is hereby incorporated by reference. The LPG from *L. donovani* used in these experiments were free of protein, and the endotoxin level was lower than 10 pg/ml. Orlandi, et al., "Structure of the Lipid Moiety of the *Leishmania donovani* Lipophosphoglycan," *J. Biol. Chem.* 262:10384–91 (1987), which is hereby incorporated by reference. The molecular weight of LPG is $9.5 \times 10^6$ and a concentration of 10 µg/ml is equivalent to 1 µM.

Figure 1:
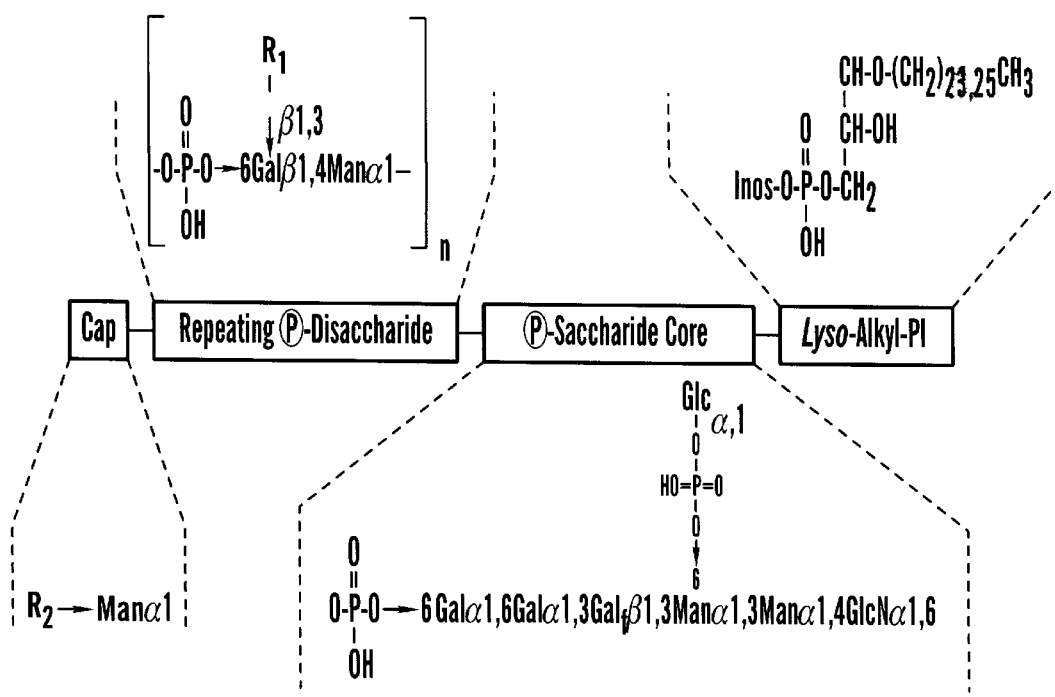
FIG. 1 illustrates the lipophosphoglycan structures from three promastigote species of Leishmania, grown in late-log phase of growth.

The distinct structural domains of LPG are illustrated in FIG. 1. The four LPG structures used (ie., PGM, core-PI, PG, and lyso-PI) were prepared as follows. Turco, et al., "Structure of the Major Carbohydrate Fragment of the *Leishmania donovani* Lipophosphoglycan," *Biochem.* 26:6233–38 (1987) and Carver, et al., "Cell-Free Biosynthesis of Lipophosphoglycan From *Leishmania donovani*: Characterization of Microsomal Galatosyltransferase and Mannosyltransferase Activities," *Biochem.* 266:10974–81 (1991), which are hereby incorporated by reference. PGM and core-PI were obtained by treating LPG with mild acid (0.02 N HCl, 5 min, 100° C.). Turco, et al., "Structure of the Major Carbohydrate Fragment of the *Leishmania donovani* Lipophosphoglycan," *Biochem.* 26:6233–38 (1987), which is hereby incorporated by reference. Following the acid cleavage, the PGM and core-PI fragments were separated by the phenyl-coupled Sepharose column chromatography. Turco, et al., "Structure of the Major Carbohydrate Fragment of the *Leishmania donovani* Lipophosphoglycan," *Biochem.* 26:6233–38 (1987), which is hereby incorporated by reference. The PG and lyso-PI were prepared by another approach. Carver, et al., "Cell-Free Biosynthesis of Lipophosphoglycan From Leishmania donovani: Characterization of Microsomal Galatosyltransferase and Mannosyltransferase Activities," *Biochem.* 266:10974–81 (1991), which is hereby incorporated by reference. LPG was subjected to a nitrous acid deamination reaction (sample suspended in 0.2 ml of 0.125 M sodium acetate, pH 4.0, and 0.25 M $NaNo_2$, 40 h at 25° C.). Following deamination and neutralization (0.4 ml of 1 N acetic acid and 0.1 N NaCl), the PG and lyso-PI were separated similarly using a phenyl-coupled Sepharose column. Carver, et al., "Cell-Free Biosynthesis of Lipophosphoglycan From *Leishmania donovani*: Characterization of Microsomal Galatosyltransferase and Mannosyltransferase Activities," *Biochem.* 266:10974–81 (1991), which are hereby incorporated by reference. The purified structural domains of LPG are >95% in purity and had a minimal cross contamination. Turco, et al., "Structure of the Major Carbohydrate Fragment of the *Leishmania donovani* Lipophosphoglycan," *Biochem.* 26:6233–38 (1987) and Carver, et al., "Cell-Free Biosynthesis of Lipophosphoglycan From *Leishmania donovani*: Characterization of Microsomal Galatosyltransferase and Mannosyltransferase Activities," *Biochem.* 266:10974–81 (1991), which are hereby incorporated by reference.

$^3$H-Lyso-alkyl-PI (3H-Lyso-PI) was obtained by metabolical labelling of *L. donovani* promastigote. Briefly, promastigotes ($\sim 10^{10}$) were cultured with [$^3$H]-inositol (0.1 mCi/ml, 16 h) in 1 ml of Dulbecco's modified Eagle's medium. Parasites were washed and glycosylphospholipids were extracted with chloroform/methanol/water (1:2:0.8) and purified by a phenyl-Sepharose column as previously described. Proudfoot, et al. "Biosynthesis of the Glycolipid Anchor of Lipophosphoglycan and the Structural Related Glycoinositol-Phospholipids From *Leishmania major,*" *Biochem. J.* 308:45–55 (1995), which is hereby incorporated by reference. Purified glycosylphospholipds were further delipidated by nitrous acid deamination to yield $^3$H-phosphatidylinositols as products followed by further purification using a phenyl-Sepharose column. $^3$H-lyso-PI was derived from $^3$H-phosphatidylinositols in methanol/toluene (1:1) with 0.2 N KOH in methanol, 25° C., 30 min). The reaction was terminated by acid neutralization and $^3$H-lyso-PI was purified using a phenyl-Sepharose column. The $^3$H-lyso-PI preparation had a specific activity of ~10,000 cpm/nmole.

Example 18

Endothelial Cells

Endothelial cell were isolated from human umbilical veins by an established method as described. Jaffe, et al., "Culture of Human Endothelial Cells Derived From Umbilical Cord Veins: Identification By Morphologic and Immunologic Criteria," *J. Clin. Investig.* 52:2745–56 (1973), which is hereby incorporated by reference. In all experiments, 2–4 passages of subcultured endothelial cells were used and were grown on fibronectin-precoated 96-well plates for 2–3 days prior to use.

Example 19

Monocytic Cells

Two human monocyte-like cell lines (THP-1 and Mono Mac 6) were used. THP-1 was obtained from ATCC (cat. #TIB-202, Rockville, Md.). Mono Mac 6 (MM6) cells were kindly provided by Dr. Ziegler-Heitbrock. Tsuchiya, et al., "Induction of Maturation in Cultured Human Monocytic Leukemia Cells By a Phorbol Diester," *Can. Res.* 42:1530–6 (1982), which is hereby incorporated by reference. These cells have been extensively characterized and exhibited morphological, biochemical, and physiological phenotypes of mature monocytes. Jaffe, et al., "Culture of Human Endothelial Cells Derived From Umbilical Cord Veins: Identification By Morphologic and Immunologic Criteria," *J. Clin. Investig.* 52:2745–56 (1973); Ziegler-Heitbrock, et al., "Establishment of a Human Cell Line (MonoMac 6) With Characteristics of Mature Monocytes," *Int. J. Cancer* 41:456–64 (1988); Tsuchiya, et al., "Induction of Maturation in Cultured Human Monocytic Leukemia Cells By a Phorbol Diester," *Can. Res.* 42:1530–6 (1982); Buras, et al., "The NF-βA (PU.1)-Binding Element, Not An Overlapping NF-IL-6 Binding Element, Is Required For Maximal IL-1β Gene Expression," *J. Immunol.* 152:4444–54 (1993); Lo, et al., "Induction of Tissue Factor on Monocytes By Adhesion To Endothelial Cells," *J. Immunol.* 154:4768–77 (1995), which are hereby incorporated by reference. Both THP-1 and MM6 behaved similarly in the monocyte adhesion assay.

Example 20

Assay of Endotoxin-Mediated Endothelial Adhesion to Monocytes

On the day of the experiment, endothelial cells were treated with endotoxin (*E. coli*, J5, 10 ng/ml) for 4 h. MM6

($1\times10^5$ cells) were subsequently added to the endotoxin-stimulated endothelial cells. Monocyte adhesion was performed for 20 min at 37° C. Unbound MM6 cells were removed by washing (3×). Adhesion of MM6 onto endothelium was quantitated by counting the bound MM6 cells under a microscope. Tolson, et al., "Expression of a Repeating Phosphorylated Disaccharide Lipophosphoglycan Epitope on the Surface of Macrophages Infected With *Leishmania donovani*," *Infect. Immun.* 58:3500–7 (1990), which is hereby incorporated by reference. The values of triplicates were averaged, and variations between triplicates were <5%. Normally, endotoxin treatment consistently promoted ~20 fold increase in monocyte adhesion. For experiments to examine if LPG could inhibit endotoxin-mediated monocyte adhesion, the endothelial cells were first preincubated with LPG (2 μM) for 1–2 h at 37° C. prior to the addition of endotoxin.

Example 21

Indirect Immunofluorescence Staining of LPG Binding to Endothelial Cells and THP-1

LPG binding to vascular cells (endothelial cells or THP-1) by indirect immunofluorescence microscopy was examined. Briefly, vascular cells were first incubated with LPG (1 μM) for a specific time period (i.e., 15 min or 1 h) at 37° C. Unbound LPG was removed by gentle washing with RPMI medium. Endothelial cells were harvested by addition of collagenase (0.05%) in PBS containing 0.02% EDTA followed by centrifugation (100 g, 5 min) and THP-1 by centrifugation (100 g, 5 min). Vascular cells were smeared onto glass slides and air-dried followed by fixation with paraformaldehyde (1%) for 20 min in the presence of human albumin (1%). An anti-LPG mAb (CA7AE, 1:2,000 dilution) was added and incubated for 30 min at room temperature followed by addition of FITC-F(ab)'$_2$ goat anti-mouse IgM (10 μg/ml). Slides were mounted and observed under a fluorescence microscope (Nikon Labophot, with episcopic fluorescence).

Example 22

Flow Cytometry Analysis of LPG Binding to Vascular Cells

FACS analysis was used to confirm LPG binding using the anti-LPG-mAb CA7AE (which recognizes the PGM portion of LPG and exhibits no cross-reactivity to other LPG domains). Elhay, et al., "Lipophosphoglycan Expression and Virulence in Ricin-Resistant Variants of *Leishmania major*," *Molec. Biochem. Paristol.* 40:255–68 (1990) and Chomczynski, et al., "Single-Step Method of RNA Isolation by Acid Guanidinium Thiocyanate-Phenol-Chloroform Extraction," *Anal. Biochem.* 162:156–9 (1987), which are hereby incorporated by reference. Endothelial cells or THP-1 cells were first incubated with LPG (1 μM) for various times (i.e., 15 min, 30 min, 1 h, and 2 h) at 27° C. Subsequently, endothelial cells were harvested by brief treatment with collagenase (0.05%) followed by centrifugation (150 g, 10 min), while THP-1 cell were directly pelleted by centrifugation (150 g, 5 min). LPG treated cells ($5\times10^5$) were suspended in RPMI medium containing 1:2,000 dilution of ascites of an anti-LPG mAb (CA7AE). MAb incubation with cells was performed at 4° C. for 20 min. Cells were subsequently washed and FITC-F(ab)'$_2$ goat anti-mouse antibody was added to a final concentration of 10 μg/ml. After 20 min incubation at 4° C., cells were washed twice with RPMI to remove unbound mAb and subjected to FACS analysis (EPICS XL flow cytometer, Coulter Corporation, Hialiah, Fla.). Where an evaluation was made regarding whether LPG fragments would block the LPG binding to cells, cells were pre-incubated with LPG fragments (1–10 μM) for 15 min prior to the incubation with intact LPG.

Example 23

Competition for LPG Binding by LPG Fragments and Binding by $^3$H-Lyso-PI

To address whether the lyso-PI and core-PI fragments may mediate cell binding, an indirect approach was used. Endothelial cells ($10^6$/ml) obtained by mild collagenase treatment were first incubated with either lyso-PI or core-PI (10 μM, 15 min 37° C.) prior to the addition of intact LPG (1 μM, 15 min 37° C.); PGM and PG (10 μM, 15 min 37° C.) were used as controls. Cells were washed, after incubation with anti-LPG mAb as described above (Indirect Immunofluorescence) and subjected to FACS analysis by binding of the intact LPG.

To evaluate whether lyso-PI may directly bind to endothelial cells, endothelial cells ($10^6$ per ml) were incubated with $^3$H-lyso-PI (1 μM [specific activity, ~10,000 cpm/nmole], 45 min, 25° C.). As a control, endothelial cells were pretreated with LPG (20 μM, 15 min, 25° C.) before the incubation with $^3$H-lyso-PI. Following incubation, the cell suspension was layed onto silicone oil (Silicones FC-50, General Electric, Waterford, N.Y.) and cell-bound $^3$H-lyso-PI was separated from free-$^3$H-lyso-PI by centrifugation (10,000 g, 10 min, room temperature). The amount of $^3$H-lyso-PI in the cell pellet and in the supernatant were solubilized in Ecoscint (National Diagnostics, Highland Park, N.J.) and quantitated by a β-emission counter (Beckman Instruments, Palo Alto, Calif.).

Example 24

Northern Blot Analysis of IL1β mRNA in Monocytes

Effects of LPG on steady-state IL-1β mRNA in monocytes was examined with Northern blot analysis. Briefly, monocytic THP-1 cells were pretreated with LPG (2 μM, from 0 min to 2 h) prior to the endotoxin (2 μg/ml) stimulation. Total RNAs were extracted using the standard protocol. March, et al., "Cloning, Sequencing and Expression of Two Distinct Human Interleukin-1 Complementary DNAS," *Nature* 315:641–7 (1985), which is hereby incorporated by reference. An equal amount of total RNA (10 to 15 μg per sample) were loaded and analyzed using 1.2% agarose-formaldehyde gel and RNA was transferred onto nylon membranes. Membranes were prehybridization at 42° C. for 4 h in hybridization buffer (50% formamide, 6×SSPE and 0.5% SDS) and hybridized in hybridization buffer (20 ml) containing $10^6$ cpm per ml with ~1.5 ng of IL-1β cDNA, [March, et al., "Cloning, Sequencing and Expression of Two Distinct Human Interleukin-1 Complementary DNAs," *Nature* 315:641–7 (1985), which is hereby incorporated by reference] previously $^{32}$P-labelled by random-priming. GAPDH cDNAs ($^{32}$P-labelled as IL-1β cDNA) was used as a control. Following hybridization, the washed and dried membranes were exposed to KODAK X-OMAT AR films. Quantitative analysis of the specific bands was performed using Phosphor Imager Analyzer (Molecular Dynamics, Sunnyvale, Calif.).

Example 25

Binding of *Leishmania donovani* to Endothelial Cells

An evaluation was made to determine if *L. donovani* would bind to endothelial cells. FIG. 16A depicts the avid binding of *L. donovani* promastigotes to endothelial cells. The binding occurred as early as 15 min and reached a maximal level at 2 h (FIG. 16A). The binding of *L. donovani* was comparable in terms of kinetics and magnitude between endothelial cells and macrophages (FIGS. 16B and 16C). A significant level of fluorescence on the cell surface of endothelial cells was consistently observed, suggesting that LPG was shed from the promastigotes and transferred to the endothelial cells during the incubation time (FIG. 16A). Moreover, *L. donovani* amastigotes were found intracellularly in endothelial cells after 2–3 days.

Example 26

Binding of Intact LPG and LPG Fragments to Endothelial Cells and Monocytes

An examination was made of whether intact LPG and LPG fragments bind to endothelial cells and monocytes. The LPG binding to human endothelial cells and monocytic THP-1 cells was obvious at 16 min, and significant LPG was bound at 1 h (FIG. 17). The cell-associated LPG was resistant to washing (FIG. 16). To confirm and better define the binding kinetics for LPG to vascular cells, flow cytometry was employed. FACS analysis confirmed the rapidity of LPG binding (FIG. 18). The level of LPG binding between endothelial cells and monocytes were comparable (FIG. 18).

Next, an examination was made to determine if LPG fragments bind to endothelial cells and monocytic THP-1 cells. Since the mAb CA7AE only recognizes the PGM domain on LPG molecule and does not cross react with other domains on LPG [Elhay, et al., "Lipophosphoglycan Expression and Virulence in Ricin-Resistant Variants of *Leishmania major*," *Molec. Biochem. Paristol.* 40:255–68 (1990) and Chomczynski, et al., "Single-Step Method of RNA Isolation by Acid Guanidinium Thiocyanate-Phenol-Chloroform Extraction," *Anal. Biochem.* 162:156–9 (1987), which are hereby incorporated by reference], it permits the examination of cell binding of only two LPG fragments containing the PGM domain (i.e., PG and PGM but not core-PI and lyso-PI fragments). In contrast to the intact LPG, neither the PGM fragment (1 μM) nor the PG fragment (1 μM) had any appreciable cell binding activity (FIG. 19); even when these LPG fragments were used at a higher concentration (10 μM).

Example 27

LPG Inhibits Endotoxin-Mediated Endothelial Adhesion to Monocytes

An evaluation was made to determine if LPG exerts inhibitory effects on endothelial cell functions. In these experiments, endothelial cells were pretreated with LPG (2 μM) for various times (i.e., 15 min, 30 min., 1 h, and 2 h) followed by the challenge with endotoxin (10 ng/ml, 4 h) prior to the monocyte adhesion assay. Endotoxin treatment consistently increased monocyte adhesion (~20 fold, 108±12 cells/mm² for control endothelial cells vs 2,050±35 cells/mm² for endotoxin-treated endothelial cells, n=25). LPG pretreatment inhibited endotoxin-mediated adhesion to monocytes in a time-dependent manner, with 2 h pretreatment of LPG completely abrogating the monocyte adhesion (FIG. 20). The effect of LPG was also dose-dependent (0.01 μM to 2 μM), with 2 μM LPG pretreatment completely inhibiting endotoxin-mediated monocyte adhesion (FIG. 20). The half-maximal inhibitory concentration of LPG was ~0.6 μM. By contrast, LPG treatment did not affect TNF-α-mediated endothelial adhesion to monocytes, indicating specificity (1,750±100 cell/mm² in TNF-α vs 1,650±130 in LPG plus TNF-α; 100±50 cell/mm² in basal, n=6). The lack of LPG inhibitory activity was similarly observed for IL-1β (100 U/ml)-mediated endothelial cell adhesion (n=4).

The inhibitory effect of LPG on monocyte functions was also confirmed. Pretreatment with LPG (2 μM) completely inhibited the endotoxin-mediated IL-1β mRNA production. The optimal time for LPG's cell inhibitory effect differs slightly between endothelial cells and monocytes. In endothelial cells, LPG inhibition of endotoxin-mediated monocyte adhesion required a minimal pretreatment time of 15 to 30 min (FIG. 20A). By contrast, LPG exerted an inhibitory effect on IL-1β mRNA expression in monocytes even when LPG was added simultaneously with the endotoxin (FIG. 20C).

Example 28

LPG Fragments Lack the Cell Inhibitory Activity

The four LPG fragments (i.e., PG, PGM, lyso-PI, and core-PI) were evaluated to determine if they possessed any cell inhibitory activity. In contrast to the intact parent LPG molecule, all four LPG fragments, at equivalent concentrations (1–10 μM), did not inhibit endotoxin-mediated endothelial adhesion to monocytes (FIG. 21). No additive inhibitory effect was observed by the co-addition of PG (2 μM) and core-PI (2 μM) fragments; this combination of fragments constitutes the full-length of the LPG molecule (FIG. 21).

Example 29

LPG Fragments Reversed the Intact LPG's Cell Inhibitory Activity

While all four LPG fragments lack the independent inhibitory effects, it was determined whether they were capable of reversing the intact LPG's cell inhibitory activity using the endothelial adhesion assay. In these experiments, endothelial cells were first incubated with the LPG fragments (10 μM, 15 min) prior to the addition of intact LPG (1 μM, 1 h) followed by the endotoxin challenge (10 ng/ml, 4 h). Interestingly, all four LPG fragments were capable of reversing LPG's inhibitory effect (FIG. 22A). Furthermore, LPG fragments' ability to reverse LPG's inhibitory effect was time-dependent. Pretreatment of endothelial cells with LPG fragments 15 min prior to the LPG significantly reversed (>80%) the LPG's effect (FIG. 22A). Simultaneous addition to LPG fragments with intact LPG resulted in ~45% blockade of LPG's inhibitory activity (FIG. 22B). No significant blocking effect of LPG fragments was observed when LPG fragments were added 15 min after the addition of intact LPG (FIG. 22C).

Example 30

Lyso-PI and Core-PI Fragments Competed LPG Binding and an Anti-LPG mAb Blocked LPG's Activity The ability of lyso-PI directly to bind to endothelial cells was examined. Endothelial cells incubated with $^3$H-lyso-PI bonded to 32.2±3.1% of the total input $^3$H-lyso-PI. The specificity of lyso-PI binding was revealed by cold-LPG competition at 20×molar excess (29±3% inhibition of $^3$H-lyso-PI binding, n=2)

Using a different approach, it was further addressed if the lyso-PI and core-PI fragments may mediate cell binding. In these experiments, cells were first incubated with either lyso-PI or core-PI (10 µM) prior to the addition of intact LPG (1 µM). Both lyso-PI and core-PI pretreatment competed (~30%) with intact LPG for binding to endothelial cells (FIG. 23A), Table 1. The effect is specific because neither PG nor PGM fragments affect the LPG's binding to cells (Table 1). FACS analysis revealed PG and PGM fragments did not bind to endothelial cells and monocytes (FIGS. 19A, B).

TABLE 1

Lyso-PI and Core-PI Fragments Competed With LPG for the Binding of Human Umbilical Vein Endothelial Cells.

| Pretreatment Condition | Percent Inhibition |
|---|---|
| Core-PI | 32.0 ± 5.0 |
| Lyso-PI | 29.9 ± 6.0 |
| PGM | 2.0 ± 5.0 |
| PG | 4.0 ± 3.0 |

Endothelial cells obtained by mild collagenase detachment were first pretreated with core-PI (10 µM) for 15 min before the addition of intact LPG (1 µM, 15 min, 37° C.). Binding was measured by flow cytometry using the anti-LPG mAb CA7AE (1:2,000 dilution). For each treatment condition, a mean index (MI) is provided by the EPICS XL software of the flow cytometer (Coulter Corp.), where MI = Σ (channel number × counts in the channel)/area. The percent inhibition was calculated as 100% × 1 − [(MI for cells pretreated with LPG fragments prior to LPG) ÷ (MI for cells treated with LPG alone)]. The percent inhibition are the means ± SE of 3 separate experiments.

The critical role of the PGM domain in cell signaling was examined by the use of an anti-LPG mAb (CA7AE). FIG. 23B depicts that the anti-LPG mAb (CA7AE, which recognizes the PGM domain), when incubated with intact LPG for 15 min, reversed LPG's inhibitory effect on endothelial adhesion to monocytes (~70% of endotoxin-induced adhesion) whereas a control murine isotypic IgM mAb had no effect on endothelial cell adhesion (1,945±180 adherent monocyte/mm$^2$ for endotoxin plus isotypic IgM mAb treatment vs 2,248±113 for endotoxin alone).

The present study confirms the cell deactivating role of LPG in the IL1β gene expression in monocytes. Russel, et al., "Leishmania and the Macrophage: A Marriage of Inconvenience," *Immunol. Today* 10:328–33 (1989); Ho, et al., "Cytokines in the Treatment of Leishmaniasis: From Studies of Immunopathology to Patient Therapy," *Biotherapy* 7:223–35 (1994); Turco, et al., "The Lipophosphoglycan of Leishmania Parasites," *Annu. Rev. Microbiol.* 46:65–94 (1992); McNeely, et al., "Requirements of Lipophosphoglycan For Intracellular Survival of *Leishmania Donovani* Within Human Monocytes," *J. Immunol.* 144:2745–50 (1990); Elhay, et al., "Lipophosphoglycan Expression and Virulence in Ricin-Resistant Variants of *Leishmania major,*" *Molec. Biochem. Parasitol.* 40:255–68 (1990); Frankenburg, et al., Effect of Glycolipids of Leishmania Parasites on Human Monocyte Activity," *J. Immunol.* 145:4284–9 (1990); Brandonisio, et al., "Impairment of the Human Phagocyte Oxidative Responses Caused by Leishmania Lipophosphoglycan (LPG): In Vitro Studies," *FEMS Immunol. Med. Microbiol.* 8(1):57–62 (1994); and Pearson, et al., "Leishmania Species: Visceral (Kala-azar), Cutaneous, and Mucosal Leishmaniasis," Mandell G. L., J. E. Bennett, and R. Dolin (eds)., Mandell, Douglas and Bennett's Principles and Practice of Infectious Diseases 4th Edition, Churchill Livingstone, New York, pages 2428–42, which are hereby incorporated by reference. Herein, a novel mechanism by which LPG affects endothelial cell function is reported. Endothelial cells, when treated with LPG, exhibited a reduction in its adhesive properties toward monocytes. FACS analysis reveals that LPG strongly suppressed the endotoxin-mediated endothelial cell expression of cell adhesion molecules (i.e., E-selectin, ICAM-1, and VCAM-1). Thus, these cellular effects of LPG on endothelium are likely to provide the basis for a reduction in monocyte adhesion. As the leishmania promastigotes must first interact with the vascular endothelium, prior to their traverse and invasion into tissue macrophages [Pearson, et al., "Leishmania Species: Visceral (Kala-azar), Cutaneous, and Mucosal Leishmaniasis," Mandell G. L., J. E. Bennett, and R. Dolin (eds)., Mandell, Douglas and Bennett's Principles and Practice of Infectious Diseases 4th Edition, Churchill Livingstone, New York, pages 2428–42, which is hereby incorporated by reference], the above data support the emerging theme that shed LPG from Leishmania can inhibit endothelial cell function. Turco, et al., "The Lipophosphoglycan of Leishmania Parasites," *Annu. Rev. Microbiol.* 46:65–94 (1992); Frankenburg, et al., Effect of Glycolipids of Leishmania Parasites on Human Monocyte Activity," *J. Immunol.* 145:4284–9 (1990); Brandonisio, et al., "Impairment of the Human Phagocyte Oxidative Responses Caused by Leishmania Lipophosphoglycan (LPG): In Vitro Studies," *FEMS Immunol. Med. Microbiol.* 8(1):57–62 (1994); Descoteaux, et al., "*Leishmania donovani* Selectively Inhibits Signal Transduction in Macrophages," *J. Immunol.* 146:2747–53 (1991); Elhay, et al., "Lipophosphoglycan Expression and Virulence in Ricin-Resistant Variants of *Leishmania major,*" *Molec. Biochem. Paristol.* 40:255–68 (1990), which are hereby incorporated by reference. This effect of LPG thus provide an explanation for the clinical observation of an absence in vascular inflammation at the initial site of leishmanial infection. Pearson, et al., "Leishmania Species: isceral (Kala-azar), Cutaneous, and Mucosal Leishmaniasis," Mandell G. L., J. E. Bennett, and R. Dolin (eds)., Mandell, Douglas and Bennett's Principles and Practice of Infectious Diseases 4th Edition, Churchill Livingstone, New York, pages 2428–42, which is hereby incorporated by reference. The LPG's effect on endothelial cells does not lead to a global suppression of endothelial function, because TNF-α-and IL-1β-mediated adhesion are unaffected. A molecular understanding of how LPG deactivates endothelial cell function may allow probing for a common pathway leading to the deactivation of vascular cells.

Similar to that in monocytes [Tolson, et al., "Expression of a Repeating Phosphorylated Disaccharide Lipophosphoglycan Epitope on the Surface of Macrophages Infected With *Leishmania donovani,*" *Infect. Immun.* 58:3500–7 (1990), which is hereby incorporated by reference], a rapid binding of LPG to endothelial cells was observed. The specific region on LPG molecules that mediate the endothelial cell binding can be inferred from the present data. Lyso-PI represents a minimal structure on LPG that mediates the cell binding. This stems from two observations. First, $^3$H-labelled lyso-PI is shown to exhibit a direct and specific binding to endothelial cells. Second, lyso-PI fragment can compete the binding of the intact LPG (~30%) to endothelial cells. These data, therefore, suggest the existence of a common site or receptor through which LPG binds. The identity of the specific receptor on the endothelial cells for LPG is unknown. However, it is unlikely that LPG merely intercalate into the lipid bilayer of vascular cells, as had been proposed previously. Miao, et al., "Potent Inhibition of Viral Fusion by Lipophosphoglycan of *Leishmania donovani,*" *Biochem.* 34:4676–83 (1995), which is hereby incorporated by reference. Although lyso-PI and core-PI can bind to endothelial cells, they lack the cell inhibitory activity, indicating that the cell signaling domain resides outside of these regions. The observation that core-PI shares the common feature with lyso-PI in competing with intact LPG binding as well as reversing the LPG functional activity strongly indicate that lyso-PI represents the minimal structure for cell binding and that saccharide-core play a minor, if any essential role.

In contrast to lyso-PI and core-PI, both PG and PGM fragments did not bind to endothelial cells.

Interestingly, these two fragments also have no cell inhibitory activity, indicating that cell binding via the lyso-PI domain is required for LPG's effect. This finding is in contrast with previous reports showing that PG fragment may bind to monocytes. Frankenburg, et al., Effect of Glycolipids of Leishmania Parasites on Human Monocyte Activity," *J. Immunol.* 145:4284–9 (1990); Descoteaux, et al., "*Leishmania donovani* Selectively Inhibits Signal Transduction in Macrophages," *J. Immunol.* 146:2747–53 (1991); and Elhay, et al., "Lipophosphoglycan Expression and Virulence in Ricin-Resistant Variants of *Leishmania major*," *Molec. Biochem. Paristol.* 40:255–68 (1990), which are hereby incorporated by reference. This discrepancy may relate to the fact that the binding characteristics of PG fragment differs between monocytes and endothelial cells. More importantly, in these studies, PG molecule were prepared by cleavage of intact LPG with phosphatidylinositol-specific phospholipase C, which generates a PG molecule terminating with a phosphoinositol group (PG-I) [Frankenburg, et al., Effect of Glycolipids of Leishmania Parasites on Human Monocyte Activity," *J. Immunol.* 145:4284–9 (1990); Orlandi, et al., "Structure of the Lipid Moiety of the *Leishmania donovani* Lipophosphoglycan," *J. Biol. Chem.* 262:10384–91 (1987); Descoteaux, et al., "*Leishmania donovani* Selectively Inhibits Signal Transduction in Macrophages," *J. Immunol.* 146:2747–53 (1991); and Elhay, et al., "Lipophosphoglycan Expression and Virulence in Ricin-Resistant Variants of Leishmania major," *Molec. Biochem. Paristol.* 40:255–68 (1990), which are hereby incorporated by reference]; whereas, in this study, a deamination method was used to deaminate LPG at the glycosamine site to yield lyso-alkyl-phosphatidylinositol and a PG molecule terminating with 2,5-anhydromannose (PG-aM). Carver, et al., "Cell-Free Biosynthesis of Lipophosphoglycan From *Leishmania donovani*: Characterization of Microsomal Galatosyltransferase and Mannosyltransferase Activities," *Biochem.* 266:10974–81 (1991), which is hereby incorporated by reference. The difference of the charges on these two forms of the PG molecule may account for the observed difference. An interesting note in support of this hypothesis comes from the observation that PI-specific-PLC generated soluble CD14 molecules have been shown to potentiate endotoxin-mediated endothelial functions. Pugin, et al., "Lipopolysaccharide (LPS) Activation of Human Endothelial and Epithelial Cells Is Mediated By LPS Binding Protein and Soluble CD14," *Proc. Natl. Acad.* 90:2744–48 (1993), which is hereby incorporated by reference. Interestingly, a combination of core-PI and PG does not constitute in the sum of the total effect of the LPG molecule. In thrombin, co-addition of γ-thrombin and β-thrombin has been shown to constitute the full functional effect of α-thrombin. Thus, the structural integrity and/or the spatial arrangement of these LPG domains in critical for the full functional activity.

The evidence suggesting that PGM domain mediates the cell inhibitory activity are: 1) a monoclonal antibody against LPG (specific for the PGM domain) can neutralize the LPG's inhibitory effect, 2) both PG and PGM fragments (both contain the PGM domain) when added prior to or concomitantly with LPG, can reverse the LPG's effect, and 3) when PG or PGM fragments are added after the LPG, there was no effect. Thus, PGM and PG, although not capable of cell binding, can reverse the LPG's inhibitory activity. It is likely that the stearic hinderance of these LPG-fragments act to compete with the LPG's signaling. Of note is that the number of repeating disaccharides increases with the transformation of non-infectious to infectious metacyclic forms of Leishmania promastigotes, again hinting to the critical role of PGM as the minimal critical structure for cell signaling. McConville, et al., "Developmental Changes in the Glycolated Phosphatidylinositols of *Leishmania donovani*," *J. Biol. Chem.* 266:15170–9 (1991); and McConville, et al., "Developmental Modification of Lipophosphoglycan During the Differentiation of *Leishmania major* Promastigotes to an Infectious Stage," *EMBO J.* 11:3593–3600 (1992), which are hereby incorporated by reference. In the prior studies, PG fragments has been shown to suppress IL-1β production, oxidative burst, and c-fos gene expression in monocytes. Frankenburg, et al., Effect of Glycolipids of Leishmania Parasites on Human Monocyte Activity," *J. Immunol.* 145:4284–9 (1990) and Descoteaux, et al., "*Leishmania donovani* Selectively Inhibits Signal Transduction in Macrophages," *J. Immunol.* 146:2747–53 (1991), which are hereby incorporated by reference. The above data similarly suggests that endothelial cells' inhibitory activity resides within the PG fragment. However, this data distinctly shows that the cell binding of LPG molecule is critical for the PGM domain to exert any cell inhibitory effect on endothelial cells.

In sum, this data suggests that the lyso-PI domain and the PGM domain on LPG mediate the cell binding and cell signaling domain, respectively. The integral spacial structure of the LPG molecule, though not required for cell binding, is absolutely essential for cell-signaling. Future efforts to create biomolecules containing the signaling domains of LPG (i.e., PGM with specific targeting means may allow the delivery of LPG-related drugs to the specific vascular sites in the treatment of various inflammatory diseases including sepsis and adult respiratory distress syndrome.

Example 31

Expression of Nitric Oxide Synthase in Murine Macrophages

To determine whether LPG can alter NOS expression, a well characterized murine macrophage cell line, RAW 264.7 cells, were used to measure NOS activity. As illustrated in FIG. 24, simultaneous addition of LPG with endotoxin and IFN-γ inhibited the enhancement of nitrite production (a product of NOS). Because macrophages encounter LPG usually in the context of entry of the parasite, it was examined whether Leishmania promastigotes, upon entry into macrophages, transfer LPG onto the macrophage cell surfaces and inhibit nitrite production. *L. donovani* promastigotes ("Ld3") within 15 minutes of attachment to human monocytes, THP-1 cells, or murine peritoneal macrcophages transferred LPG onto the surface of the macrophages, as determined by a monoclonal antibody against LPG and indirect fluorescent microscopy. Two hours after entering murine peritoneal macrophages, Ld3 promastigoes suppressed endotoxin- and IFN-γ induction of NOS activity; the inhibition was parasite dose dependent. Furthermore, higher amounts of agonists (i.e. endotoxin and IFN-γ) could not reverse the inhibition by LPG.

Example 32

Expression of Nitric Oxide Synthase in Human Macrophages

In studies to delineate macrophage effector mechanisms for in vitro control of *M. tuberculosis*, the following data shows expression of NOS in human peripheral blood derived macrophages infected with *M. tuberculosis* and alveolar macrophages from patients with active turberculosis. This evidence is provided by histochemical methods, draphorase activity, and mRNA reverse transcription coupled to polymerase chain reaction ("RT/PCR") with Southern blot (primers constructed from human hepatic NOS consensus sequences). Evidence that LPG pretreatment suppressed *M. tuberculosis*-induction of NOS mRNA in IFN-γ-primed macrophages as determined by RT/PCR is shown in FIG. 25.

RT/PCR was also used to delineate the kinetics of NOS mRNA induction. Results demonstrated the induction of NOS mRNA at 48 hours after infection with *M. tuberculosis* H37Ra in *M. tuberculosis*-infected macrophages activated with IFN-γ. In contrast, NOS mRNA is not detected in uninfected macrophages. Co-culture with autologous primed T cells further enhanced the expression of inducible NOS. Confirmatory data that the detected NOS was inducible NOS is the time dependent induction of NOS (little or no NOS mRNA is found at 24 hours despite IFN-γ treatment and co-culture with T cells.

Example 33

Thrombosis: Tissue Factor Generation

To further examine if LPG can inhibit other endothelial cell functions, it was determined whether LPG inhibits thrombosis. Since thrombosis is mediated by the release of tissue factor ("TF") by endothelial cells, the ability of LPG to inhibit TF production was evaluated. Cultured endothelial cells when stimulated by endotoxin express TF as determined by a one-stage clotting assay. Helin et. al., "Allogeneic Induction of the Human T-cell-instructed Monocyte Procoagulant Response is Rapid and is Elicited by HLA-DR," *J. Exp. Med.* 158: 962–75 (1983), which is hereby incorporated by reference. As illustrated in FIG. 26, pretreatment with LPG caused a dose-dependent inhibition of endotoxin induction of TF production; LPG (2 $\mu$M) completely abrogated endotoxin-induction of TF. To explore whether this effect was agonist specific, another agonist, TNF-α which is known to up-regulate TF generation, was used. It was found that LPG had no effect on TNF-α induction of endothelial cell production of TF. Overall, the data strongly suggest that LPG can effect three vascular cell functions: cytokine release, adhesion properties, and TF generation.

Example 34

Figure 27A:
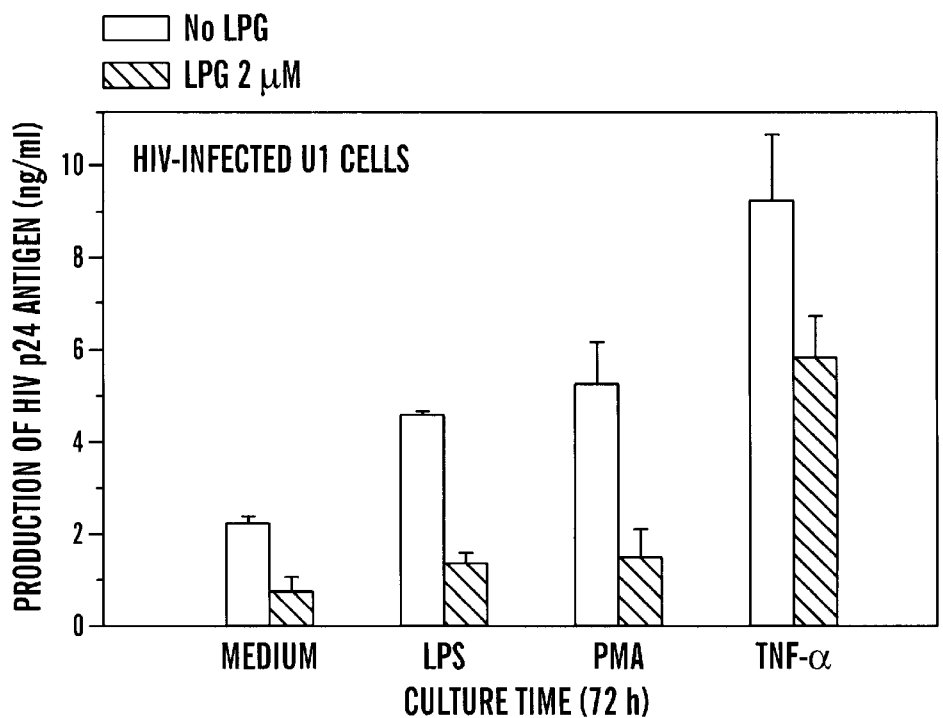
Figure 27B:
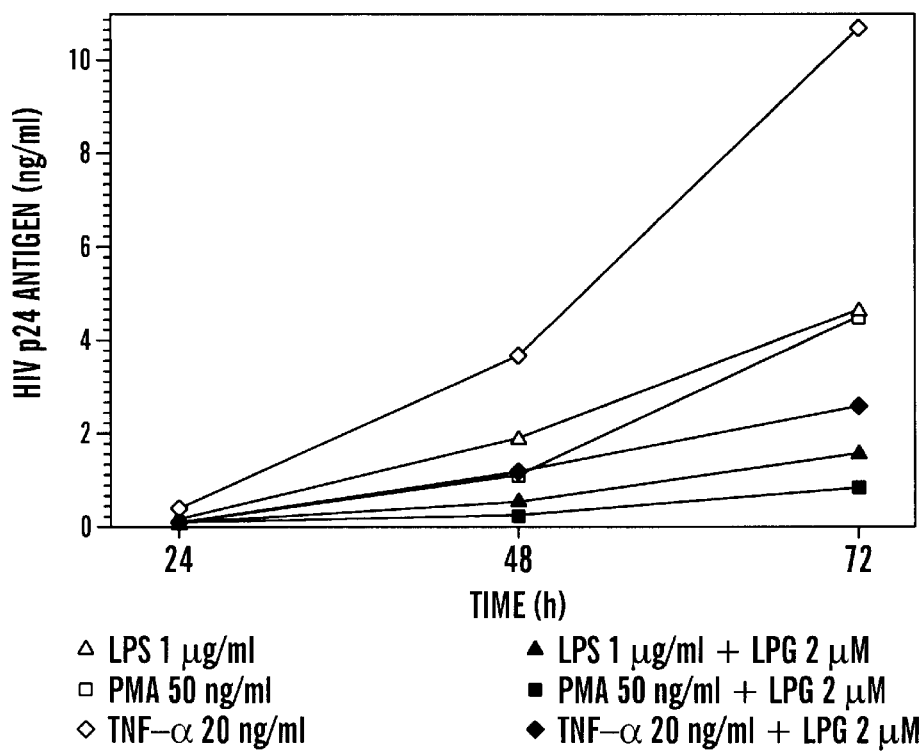
Figure 27C:
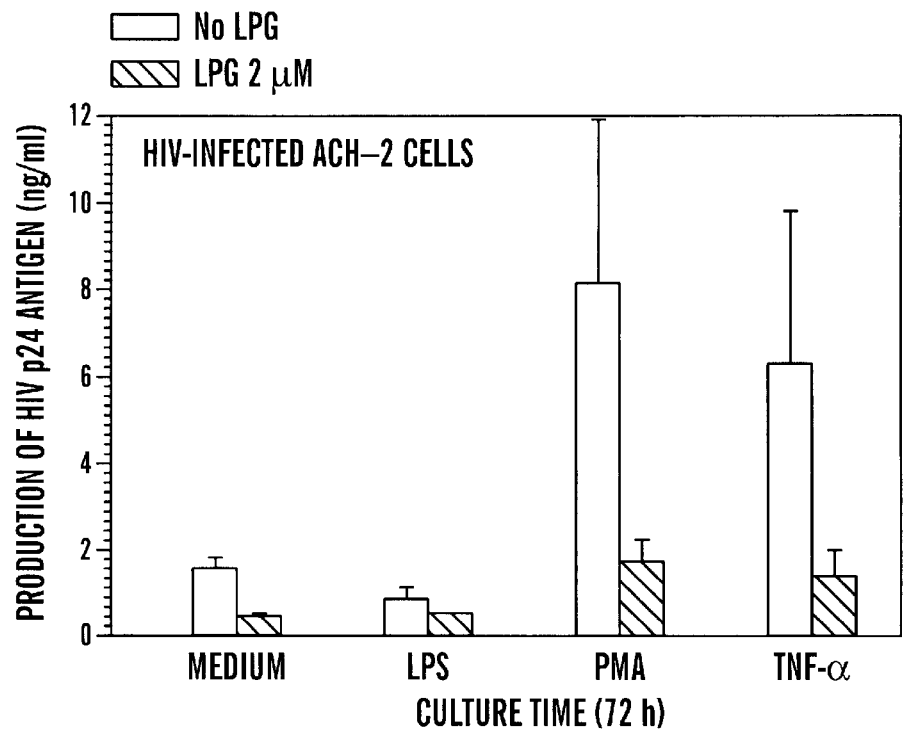
Figure 27D:
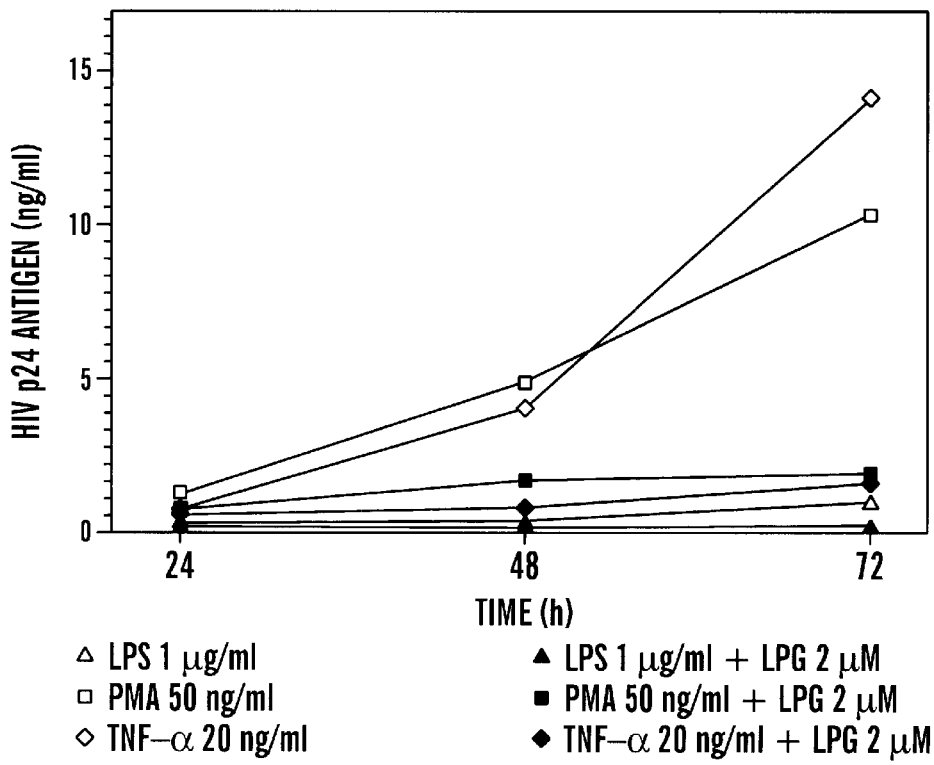
Figure 27C:
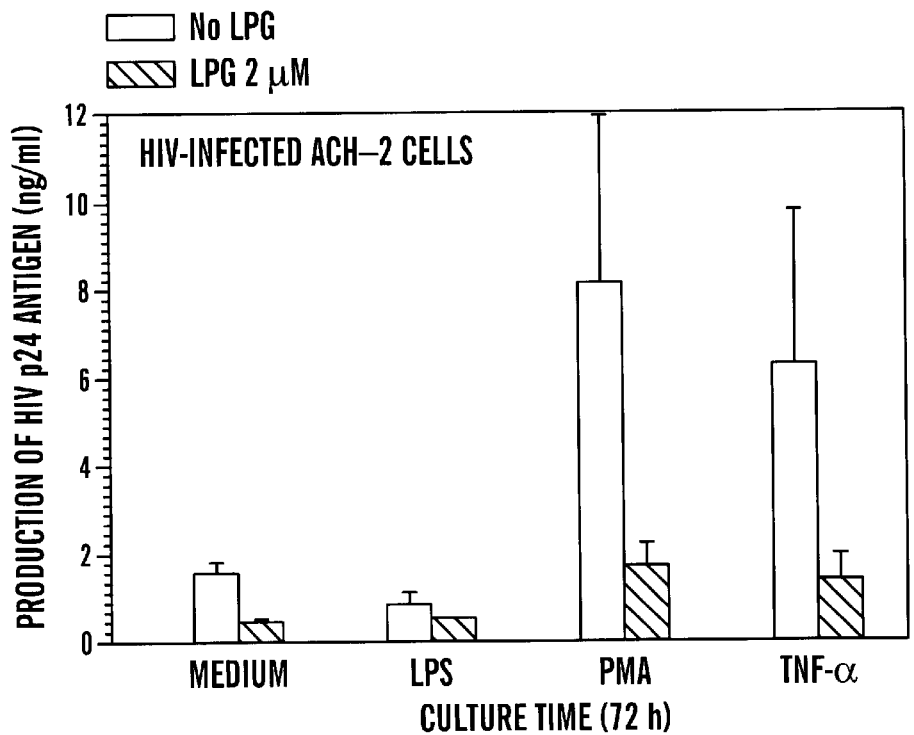
Figure 27D:
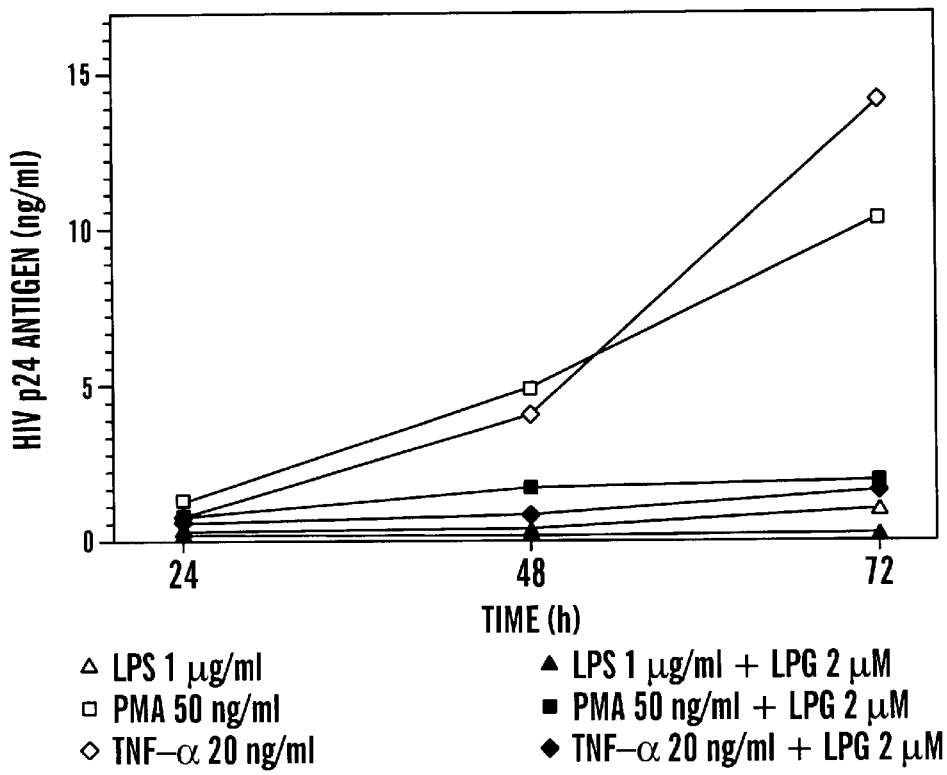

LPG of Leishmania Inhibits HIV Production in Chronically HIV-Infected Mononuclear Cells LPG, the major surface molecule of Leishmania, has macrophage deactivating functions. Based on the ability of LPG to suppress the generation of ROI and cytokine gene expression, we evaluated the potential that LPG may similarly suppress HIV production. FIGS. 27A–D illustrate the effect of 2 $\mu$M LPG pretreatment for 2 h on the induction HIV from chronically HIV-infected monocytic and T cell lines respectively, U1 and ACH-2 cells. LPG treatment of U1 cells for 72 h inhibited basal production of HIV p24 antigen at basal and induction in response to PMA, TNF-α and LPS by 90%, 82%, 60% and 66%, respectively (FIGS. 27A, B). The suppression of HIV p24 antigen production was time-dependent (FIG. 27B). LPG treatment of ACH-2 cells for 72 h similarly inhibited basal production of HIV p24 antigen and production in response to PMA, TNF-α and LPS by 62%, 81%, 88% and 69%, respectively (FIGS. 27C, D). The inhibition was also time-dependent. The results are the mean of 2 separate experiments and the SD was less than 10%. The suppression of HIV p24 antigen production was specific because cells treated or not treated with LPG had similar percentages of viable cells (98%) and LPG treatment did not alter cell proliferation as measured by bromo-deoxy-uridine incorporation assay in each of the stimulation conditions.

Example 35

IL-1β and TNF-α Transcription

First, it was examined whether LPG's suppression of IL-1β and TNF-α steady state mRNA was mediated by inhibiting gene transcription. The nuclear run-on assay was used to determine the effect of LPG on transcriptional regulation IL-1β and TNF-α . Nuclei were isolated from cells pretreated with LPG and challenged with endotoxin, cells cultured in medium, or treated with endotoxin. The in vivo transcribed mRNA was captured by membrane bound plasmid containing the IL-1β TNF-α, or GAPDH cDNA. Pretreatment with LPG suppressed endotoxin-mediated IL-1β and TNF-α transcription by −60% and −70%, respectively (FIG. 28). In contrast, LPG had no effect on GAPDH transcription. In additional studies using actinomycin D to terminate transcription, we observed that LPG increased IL-1β mRNA instability by −30% while having minimal effect on TNF-α mRNA stability (data not shown). Therefore, LPG inhibition of TNF-α gene expression is predominantly by suppressing gene transcription. To delineate the transcriptional regulation by LPG, we examined whether a specific IL-1β promoter gene sequence(s) may mediate LPG's inhibitory effects.

It was next examined if LPG is capable of suppressing endotoxin-induced TNF-α expression. LPG significantly suppressed endotoxin induction of TNF-α expression when added 4 h prior to addition of endotoxin and was effective when added 2 h after endotoxin (FIG. 29).

Example 36

Binding of LPG to Serum Factor(s) or Protein(s)

In functional studies on the effect of LPG on IL-1β gene expression, it was demonstrated that in the presence of 2.5% or 5% serum, LPG suppresses endotoxin-activation of IL-1β promoter activity. THP-1 cells were transfected with IL-1β promoters linked to chloramphenicol acetyl transferase and cultured in medium containing 2.5% or 5% fetal bovine serum ("FBS"). After 48 h, cells were pretreated with LPG (2 $\mu$M) for 2 h and challenged with endotoxin ("LPS") (2 $\mu$g/ml). As a control, cells were treated with medium or medium-containing endotoxin for 24 h. Cells were harvested and cell lysates were assayed for chloramphenicol acetyl transferase activity. It was found that LPG's inhibition of IL-1β gene expression was similar in cells treated with 2.5% or 5% of FBS.

It was next examined whether LPG may bind to serum factor(s) or protein(s), because many drugs bind to serum protein(s) and LPS activation of vascular cells is facilitated by LPS binding proteins (e.g., the LPS binding protein and spectrin). It was reasoned that compared to no serum the presence of serum that can bind to LPG will decrease the amount of LPG detected on the cell surface. Using human vascular endothelial cells, the effect of FBS or human AB serum ("ABS") on LPG binding to endothelial cells was studied. Endothelial cells were cultured in medium or medium-containing varying amounts (percentages) of FBS, ABS, or a mixture of FBS/ABS (16%/4%). LPG were added or not to endothelial cells for 2 h. Following washing to remove unbound LPG, cells were incubated with monoclonal antibody to LPG (CA7AE) and the amount of cell associated LPG was determined by FACS analysis.

As shown in FIG. 30, endothelial cells exposed to LPG (2 μM) in the presence of 10% or higher amounts of serum resulted in a dose-dependent decrease in LPG binding to cells. These findings suggest that serum factor(s), such as serum albumin, bind to LPG.

Example 37

Ability of LPG to Suppress Expression of Adhesion Molecules E-selectin and ICAM-1, Induced by Endotoxin Endothelial cells pretreated with LPG at indicated amounts for 1 h were subsequently challenged with endotoxin. Washed cells incubated with monoclonal antibody specific for E-selectin or ICAM-1 were counter stained with fluorescein labeled anti-murine antibody, fixed and analyzed by FACS.

In these functional studies of the effect of LPG on endotoxin-mediated endothelial cell adhesion properties, it demonstrated that treatment with LPG suppresses endotoxin activation of endothelial cell adhesion to monocytes. The adhesion properties of endothelial cells are provided by the expression of specific adhesion molecules (e.g., E-selectin and ICAM-1). These adhesion molecules are not expressed or are minimally expressed at a resting state. In response to endotoxin, endothelial cells express high amounts of these adhesion molecules. This allows attachment of leukocytes, such as monocytes to the endothelial cells. FIG. 31 shows such LPG blockage or suppression of endotoxin-mediated expression of E-selectin and ICAM-1, which is dose dependent.

Although the invention has been described in detail for the purpose of illustration, it is understood that such detail is solely for that purpose, and variations can be made therein by those skilled in the art without departing from the spirit and scope of the invention, which is defined by the following claims.

What is claimed:

1. A method for reducing inflammation in a mammal which has an inflammatory disease comprising:
   administering an isolated lipophosphoglycan or an isolated lipophosphoglycan analog to said mammal in an amount effective to reduce vascular inflammation, wherein the lipophosphoglycan analog is selected from the group consisting of phosphatidylinositol lipid anchor of lipophosphoglycan, polyphosphosaccharide core of lipophosphoglycan, small oligosaccharide cap structure of lipophosphoglycan, repeating phosphorylated saccharide region lipophosphoglycan and extracellular lipophosphoglycan glycoconjugates.

2. A method according to claim 1, wherein said administering is carried out orally, intravenously, intramuscularly, intraperitoneally, subcutaneously, by intranasal instillation, by application to mucous membranes, or by instillation into hollow organ walls or newly vascularized blood vessels.

3. A method according to claim 1, wherein the inflammatory disease is selected from the group consisting of transplantation rejection, nephritis, asthma, respiratory distress syndrome, gastritis, rheumatoid diseases, sepsis, thrombosis, autoimmune diseases, and coronary disease.

4. A method according to claim 3, wherein the inflammatory disease is transplantation rejection selected from the group consisting of renal allograft rejection, cardiac allograft rejection, and transplantation-associated vasculopathy.

5. A method according to claim 3, wherein the inflammatory disease is nephritis selected from the group consisting of acute glomerulonephritis, lupus nephritis, and tubulointerstitial nephritis.

6. A method according to claim 3, wherein the inflammatory disease is asthma in the form of allergic asthma.

7. A method according to claim 3, wherein the inflammatory disease is respiratory distress syndrome.

8. A method according to claim 3, wherein the inflammatory disease is gastritis in the form of indomethacin-induced gastritis.

9. A method according to claim 3, wherein the inflammatory disease is a rheumatoid disease selected from the group consisting of lupus and arthritis.

10. A method according to claim 3, wherein the inflammatory disease is an autoimmune disease selected from the group consisting of vasculitis and diabetes.

11. A method according to claim 3, wherein the inflammatory disease is sepsis.

12. A method according to claim 3, wherein the inflammatory disease is thrombosis.

13. A method according to claim 3, wherein the inflammatory disease is a coronary artery disease selected from the group consisting of restenosis after angioplasty, restenosis after by-pass surgery, and ischemia.

14. A method according to claim 3, wherein the inflammatory disease is HIV.

\* \* \* \* \*